United States Patent
DeKorver et al.

(10) Patent No.: US 9,974,304 B2
(45) Date of Patent: *May 22, 2018

(54) USE OF MACROCYCLIC PICOLINAMIDES AS FUNGICIDES

(71) Applicant: DOW AGROSCIENCES LLC, Indianapolis, IN (US)

(72) Inventors: Kyle A. DeKorver, Lafayette, IN (US); Johnathan E. DeLorbe, Pearland, TX (US); Kevin G. Meyer, Zionsville, IN (US); Chenglin Yao, Westfield, IN (US); Ronald J. Heemstra, Fishers, IN (US); William H. Dent, III, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/577,949

(22) Filed: Dec. 19, 2014

(65) Prior Publication Data

US 2015/0181868 A1 Jul. 2, 2015

Related U.S. Application Data

(60) Provisional application No. 61/920,942, filed on Dec. 26, 2013, provisional application No. 61/920,946, filed on Dec. 26, 2013.

(51) Int. Cl.
| | |
|---|---|
| *A01N 43/24* | (2006.01) |
| *A01N 43/40* | (2006.01) |
| *A01N 47/18* | (2006.01) |
| *A01N 53/00* | (2006.01) |
| *C07D 321/00* | (2006.01) |
| *C07D 405/12* | (2006.01) |

(52) U.S. Cl.
CPC ............ *A01N 43/24* (2013.01); *A01N 43/40* (2013.01); *A01N 47/18* (2013.01); *A01N 53/00* (2013.01); *C07D 321/00* (2013.01); *C07D 405/12* (2013.01)

(58) Field of Classification Search
CPC ........ A01N 43/24; A01N 47/18; A01N 43/40; A01N 53/00; C07D 321/00; C07D 405/12
See application file for complete search history.

(56) References Cited

U.S. PATENT DOCUMENTS

| | | | |
|---|---|---|---|
| 4,051,173 | A | 9/1977 | Schact et al. |
| 5,401,871 | A | 3/1995 | Feldmann-Krane et al. |
| 6,355,660 | B1 | 3/2002 | Ricks |
| 6,436,421 | B1 | 4/2002 | Schindler et al. |
| 6,410,572 | B1 | 6/2002 | Schelberger et al. |
| 6,521,622 | B1 | 2/2003 | Ricks |
| 6,706,740 | B2 | 3/2004 | Ricks |
| 6,861,390 | B2 | 3/2005 | Meyer |
| 6,916,932 | B2 | 7/2005 | Meyer et al. |
| 6,927,225 | B2 | 8/2005 | Ricks |
| 7,034,035 | B2 | 4/2006 | Ricks |
| 7,183,278 | B1 | 2/2007 | Imamura |
| 7,250,389 | B1 | 7/2007 | Sakanaka |
| RE39,991 | E | 1/2008 | Ricks et al. |
| 7,442,672 | B2 | 10/2008 | Muller et al. |
| 8,008,231 | B2 | 8/2011 | Leatherman |
| 8,470,840 | B2 | 6/2013 | Klittich et al. |
| 8,476,193 | B2 | 7/2013 | Kenney et al. |
| 8,604,215 | B2 | 12/2013 | Phiasivongsa et al. |
| 8,785,479 | B2 | 7/2014 | Meyer |
| 8,835,462 | B2 | 9/2014 | Meyer |
| 8,883,811 | B2 | 11/2014 | Owen |
| 8,916,579 | B2 | 12/2014 | Boebel et al. |
| 9,006,259 | B2 | 4/2015 | Boebel et al. |
| 9,084,418 | B2 | 7/2015 | Ehr et al. |
| 9,131,690 | B2 | 9/2015 | Meyer et al. |
| 9,144,239 | B2 | 9/2015 | Meyer et al. |
| 9,156,816 | B2 | 10/2015 | Ito et al. |
| 9,179,674 | B2 | 11/2015 | Martin et al. |
| 9,185,911 | B2 | 11/2015 | Inami et al. |
| 9,198,419 | B2 | 12/2015 | Owen et al. |
| 9,265,253 | B2 | 2/2016 | Li et al. |

(Continued)

FOREIGN PATENT DOCUMENTS

| | | |
|---|---|---|
| CN | 102638989 | 8/2012 |
| EP | 1054011 | 11/2000 |

(Continued)

OTHER PUBLICATIONS

Webster's New World Dictionary, $2^{nd}$ college edition,the World Publishing Co., New York, p. 1127 (1972).*

Koyanagi, T. et al., "Biososterism in Agrochemicals," in: Synthesis and Chemistry of Agrochemials, Baker D. et al., ACS Symposium Series, American Chemical Society, Washington, DC, pp. 15-24 (1995).*

Anonymous, Synergistic Fungicidal Composition of Heterocyclic Aromatic Amides and Trizaoles, IP.com, Electronic Publication, 2004, 11 pages.

Anonymous, Synergistic Fungicidal Composition of Heterocyclic Aromatic Amides and Triazoles, IP.com Journal, IP.com Inc., West Henrietta, NY, US, Dates Jul. 2004, 10 pages.

(Continued)

*Primary Examiner* — John Pak
(74) *Attorney, Agent, or Firm* — Charles W. Amett; Faegre Baker Daniels LLP

(57) ABSTRACT

The invention relates to macrocyclic picolinamides of Formula I and their use as fungicides.

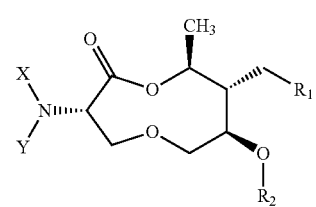

23 Claims, No Drawings

(56) References Cited

U.S. PATENT DOCUMENTS

| | | | |
|---|---|---|---|
| 9,439,422 B2 | 9/2016 | Martin et al. | |
| 9,549,555 B2 | 1/2017 | DeLorbe et al. | |
| 9,629,365 B2 | 4/2017 | Li et al. | |
| 9,681,664 B2 | 6/2017 | LaLonde et al. | |
| 9,700,047 B2 | 7/2017 | Lu | |
| 9,750,248 B2 | 9/2017 | Ouimette et al. | |
| 2002/0119979 A1 | 8/2002 | Degenhardt et al. | |
| 2002/0177578 A1 | 11/2002 | Ricks | |
| 2003/0018012 A1 | 1/2003 | Ricks | |
| 2003/0018052 A1 | 1/2003 | Ricks | |
| 2003/0022902 A1 | 1/2003 | Ricks | |
| 2003/0022903 A1 | 1/2003 | Ricks et al. | |
| 2004/0034025 A1 | 2/2004 | Ricks | |
| 2004/0048864 A1 | 3/2004 | Ricks | |
| 2004/0171838 A1 | 9/2004 | Owen | |
| 2004/0186296 A1 | 9/2004 | Nyaz | |
| 2004/0192924 A1 | 9/2004 | Meyer | |
| 2005/0239873 A1 | 10/2005 | Hockenbery | |
| 2006/0040995 A1 | 2/2006 | Bacque et al. | |
| 2007/0010401 A1 | 1/2007 | Noon | |
| 2007/0060579 A1 | 3/2007 | Wachendorff-Neumann | |
| 2007/0066629 A1 | 3/2007 | Tormo I Blasco | |
| 2008/0070985 A1 | 3/2008 | Derrer et al. | |
| 2008/0293798 A1 | 11/2008 | Dietz | |
| 2008/0318785 A1 | 12/2008 | Koltzenburg | |
| 2009/0203770 A1 | 8/2009 | Hockenberry et al. | |
| 2009/0306142 A1 | 12/2009 | Carson | |
| 2010/0016163 A1 | 1/2010 | Keiper et al. | |
| 2011/0034493 A1 | 2/2011 | Boebel et al. | |
| 2011/0053891 A1 | 3/2011 | Boebel et al. | |
| 2011/0053966 A1 | 3/2011 | Klittich et al. | |
| 2011/0070278 A1 | 3/2011 | Lopez | |
| 2011/0082039 A1 | 4/2011 | Keeney et al. | |
| 2011/0082160 A1 | 4/2011 | Owen | |
| 2011/0082162 A1 | 4/2011 | Lorsbach et al. | |
| 2011/0306644 A1 | 12/2011 | Hoekstra et al. | |
| 2012/0035054 A1 | 2/2012 | Ehr et al. | |
| 2012/0245031 A1 | 9/2012 | Gewehr et al. | |
| 2013/0090298 A1 | 4/2013 | Lee et al. | |
| 2013/0296371 A1 | 11/2013 | Meyer | |
| 2013/0296372 A1 | 11/2013 | Owen et al. | |
| 2013/0296373 A1* | 11/2013 | Meyer | A01N 43/40 514/336 |
| 2013/0296374 A1 | 11/2013 | Owen et al. | |
| 2013/0296375 A1 | 11/2013 | Meyer et al. | |
| 2014/0128411 A1 | 5/2014 | Ogawa et al. | |
| 2014/0187587 A1 | 7/2014 | Ouimette et al. | |
| 2014/0187588 A1 | 7/2014 | Lalonde | |
| 2014/0187590 A1 | 7/2014 | Ouimette et al. | |
| 2014/0275171 A1 | 9/2014 | Meyer | |
| 2014/0357713 A1 | 12/2014 | Damaj et al. | |
| 2015/0065529 A1 | 3/2015 | Owen | |
| 2015/0183759 A1 | 7/2015 | DeLorbe et al. | |
| 2015/0289508 A1 | 10/2015 | Meyer et al. | |
| 2015/0322051 A1 | 11/2015 | Lu | |
| 2016/0007601 A1 | 1/2016 | Boebel et al. | |
| 2017/0183324 A1 | 6/2017 | Li et al. | |
| 2017/0273306 A1 | 9/2017 | LaLonde et al. | |

FOREIGN PATENT DOCUMENTS

| | | |
|---|---|---|
| EP | 1516874 | 3/2005 |
| WO | 1999011127 | 11/1999 |
| WO | 2001/14339 | 3/2001 |
| WO | WO 2001/014365 | 3/2001 |
| WO | WO 03/011857 | 2/2003 |
| WO | WO 03/035617 | 5/2003 |
| WO | WO 2007017416 | 2/2007 |
| WO | 2009040397 | 9/2008 |
| WO | WO 2011028657 | 3/2011 |
| WO | WO 2011044213 | 4/2011 |
| WO | WO 2011069893 | 6/2011 |
| WO | 2012020777 | 2/2012 |
| WO | WO 2012/016972 | 2/2012 |
| WO | WO 2012016989 | 2/2012 |
| WO | 2012/070015 | 5/2012 |
| WO | WO 2013/110002 | 7/2013 |
| WO | WO 2013/116251 | 8/2013 |
| WO | 2015100181 | 7/2015 |
| WO | 2015100182 | 7/2015 |
| WO | WO 2015/103161 | 7/2015 |
| WO | 2016007525 | 1/2016 |

OTHER PUBLICATIONS

K. Tani, et al, Journal of Antibiotics, vol. 55, No. 3, Mar. 2002, pp. 315-321.
Z. Hu, et al, Synthesis of Novel Analogues of Antimycin A3, Tetrahedron Letters 49 (2008) pp. 5192-5195.
Y. Usuki, et al, Journal of Antibiotics, vol. 55, No. 6, Jun. 2002, pp. 607-610.
Huang, et al., Synergistic Interactions between Chitinase ChiCW and Fungicides Against Plant Fungal Pathogens, J. Microbiol. Biotechnol., 2008, 18(4) 784-787.
Backman, P., Fungicide Formulation: Relationship to Biological Activity, 1978, 16, 211-237.
Latin, et al, Re-Examining Fungicide Synergism for Dollar Spot Control, GCM, 2008, 84-87.
O'Sullivan, et al., Fungicide Resistance—an Increasing Problem, Proceedings of National Tillage Conference 2007, Published by Crop Research Centre Oak Park Carlow, date Jan. 31, 2007, 14 pages.
Masashi Ueki et al., "UK-2A, B, C, and D, Novel Antifungal Antibiotics from *streptomyces* sp. 517-02 I. Fermentation, Isolation, and Biological Properties," the Journal of Antibiotics, vol. 49, No. 7, Jul. 1996, pp. 639-634.
Usuki, et al., "Semi-synthesis and biological evaluation of analogues of UK-2A, a novel antifungal antibiotic from *steptomyces* sp. 517-02," Bioorganic & Medicinal Chemistry Letters, Pergamon, Amsterdam, KL, vol. 15, No. 8, Apr. 15, 2005, pp. 2011-2014, XP027801790.
PUBCHEM, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>.
Gisi, U., The American Phytopathological Society, vol. 86, No. 11, 1996, p. 1273.
International Searching Authority, International Search Report, Written Opinion, and International Preliminary Report on Patentability for PCT/US2014/071699, dated Apr. 20, 2015, 10 pages.
International Searching Authority, International Search Report, Written Opinion, and International Preliminary Report on Patentability for PCT/US2014/071700, dated Apr. 17, 2015, 13 pages.
Anonymous, "Fungicidal Mixtures," an IP.com Prior Art Database Technical Disclosure, IPCOM000126160D, Jul. 5, 2005, 12 pages.
BASF New Fungicide Xemium Got Full Approval in EU. Agronews. Jul. 18, 2012 [retrieved on Feb. 4, 2014]. Retrieved from the Internet: ,URL:http://news.agropages.com/News/NewsDetail---7386.htm.
Bolton, MD et al., Wheat leaf rust caused by Puccinia triticina. Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.
Davari, M. et al. ""Quantum Chemical Investigation of Intramolecular Thione-Thiol Tautomerism of 1, 2, 4-triazole-3-thione and its disubstituted derivatives,"" Journal of Molecular Modeling, Sep. 2009, 16(5), pp. 841-855.
FRAC Code List: Fungicides Sorted by Mode of Action (including FRAC Code numbering), Dec. 2008, pp. 1-10.
Kissling, Crop Protection Pipeline Value Jumps to Euro 2.4 Billion. BASF Mar. 11, 2010 [retrieved on Feb. 4, 2014], Retrieved from the internet: ,URL:http://agro.basf.com/agri/AP-Internet/en/content/news_room/news/basf-crop-protection-pipeline-value.

(56) References Cited

OTHER PUBLICATIONS

Parker, J.E., et al., ""Mechanism of Binding of Prothioconazole to Mycosphaerella graminicola CYP51 Differes from That of Other Azole Antifungals,"" Applied and Environmental Microbiology, Feb. 2011, pp. 1460-1465.
Science for a Better Life, Bayer Cropscience, Jun. 2008, p. 22.
Sulfonate (http://www.hichem.com/product/showproduct.php?id=334639) Mar. 28, 2013, p. 1-4.
The Merck Index, Twelfth Edition, S. Budavari, Ed. Merck and Co., Whitehouse Station, NJ, 1996 pp. 2220, 3666, 7937 and 7946.
Webster's New World Dictionary, 2nd college edition, The World Publishing Co., New York, p. 1127 (1972).
Wilson, C.L. et al. "Fruit Volatiles Inhibitory to Monilinia Fruiticola and Botrytis cinerea," 1987, Plant Disease 71: 316-319.

\* cited by examiner

USE OF MACROCYCLIC PICOLINAMIDES AS FUNGICIDES

CROSS REFERENCE TO RELATED APPLICATIONS

This application claims the benefit of U.S. Provisional Patent Application Ser. Nos. 61/920,942 and 61/920,946, each filed Dec. 26, 2013, the disclosures of which are hereby incorporated by reference in their entireties.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

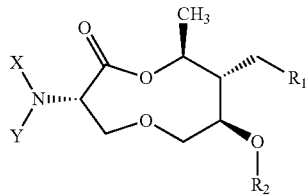

wherein X is hydrogen or $C(O)R_3$;
Y is hydrogen, $C(O)R_3$, or Q;
Q is

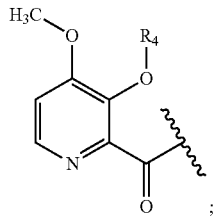

$R_1$ is hydrogen, alkyl, alkenyl, aryl, alkoxy, or acyl, each optionally substituted with 0, 1 or multiple $R_6$;

$R_2$ is hydrogen, alkyl, aryl, $—Si(R_5)_3$, alkenyl, or acyl, each optionally substituted with 0, 1 or multiple $R_6$;

$R_3$ is alkoxy or benzyloxy, each optionally substituted with 0, 1, or multiple $R_6$;

$R_4$ is hydrogen, $—C(O)R_5$, or $—CH_2OC(O)R_5$;

$R_5$ is alkyl, alkoxy, or aryl, each optionally substituted with 0, 1, or multiple $R_6$;

$R_6$ is hydrogen, alkyl, aryl, acyl, halo, alkenyl, alkoxy, heteroaryl, heterocyclyl, or thioalkyl, each optionally substituted with 0, 1, or multiple $R_7$; and $R_7$ is hydrogen, alkyl, aryl, or halo.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by the those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like. In some exemplary embodiments, the term "alkyl" refers to a branched, unbranched, or saturated cyclic carbon chain, including containing from 1 to 12 carbon atoms, from 1 to 6 carbons, or from 1 to 4 carbons.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like. In some exemplary embodiments, the term "alkenyl" refers to a branched, unbranched, or saturated cyclic carbon chain, including containing from 1 to 12 carbon atoms, from 1 to 6 carbons, or from 1 to 4 carbons.

The term "alkynyl" refers to a branched or unbranched carbon chain containing one or more triple bonds including, but not limited to, propynyl, butynyl and the like. In some exemplary embodiments, the term "alkynyl" refers to a branched, unbranched, or saturated cyclic carbon chain, including containing from 1 to 12 carbon atoms, from 1 to 6 carbons, or from 1 to 4 carbons.

The term "aryl" refers to any aromatic, mono- or bi-cyclic, containing 0 heteroatoms.

The term "heterocycle" refers to any aromatic or non-aromatic ring, mono- or bi-cyclic, containing one or more heteroatoms. In some exemplary embodiments, the one or more heteroatoms are independently selected from nitrogen, oxygen, phosphorous, and sulfur.

The term "alkoxy" refers to an —OR substituent.
The term "cyano" refers to a —C≡N substituent.
The term "hydroxyl" refers to an —OH substituent.
The term "amino" refers to a $—NR_2$ substituent.
The term "arylalkoxy" refers to $—O(CH_2)_n—Ar$ where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a $—NO_2$ substituent.
The term thioalkyl refers to an —SR substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

In one exemplary embodiment, a composition for the control of a fungal pathogen is provided. The composition includes at least one compound of Formula I.

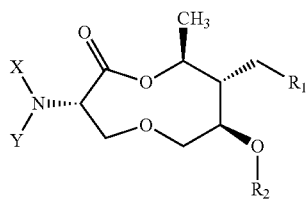

I wherein
X is hydrogen or C(O)R$_3$;
Y is hydrogen, C(O)R$_3$, or Q;
Q is

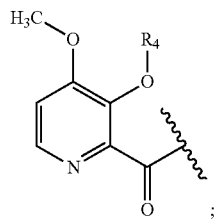

;

R$_1$ is hydrogen, alkyl, alkenyl, aryl, alkoxy, or acyl, each optionally substituted with 0, 1 or multiple R$_6$;
R$_2$ is hydrogen, alkyl, aryl, —Si(R$_5$)$_3$, alkenyl, or acyl, each optionally substituted with 0, 1 or multiple R$_6$;
R$_3$ is alkoxy or benzyloxy, each optionally substituted with 0, 1, or multiple R$_6$;
R$_4$ is hydrogen, —C(O)R$_5$, or —CH$_2$OC(O)R$_5$;
R$_5$ is alkyl, alkoxy, or aryl, each optionally substituted with 0, 1, or multiple R$_6$;
R$_6$ is hydrogen, alkyl, aryl, acyl, halo, alkenyl, alkoxy, heteroaryl, heterocyclyl, or thioalkyl, each optionally substituted with 0, 1, or multiple R$_7$; and
R$_7$ is hydrogen, alkyl, aryl, or halo.

In a more particular embodiment, X is hydrogen and Y is Q. In a more particular embodiment of any of the above embodiments, R$_4$ is hydrogen. In a more particular embodiment of any of the above embodiments, R$_1$ is chosen from alkyl and aryl, each optionally substituted with 0, 1 or multiple R$_6$. In a more particular embodiment of any of the above embodiments, R$_2$ is chosen from hydrogen, alkyl, aryl, and acyl, each optionally substituted with 0, 1 or multiple R$_6$. In a more particular embodiment of any of the above embodiments, R$_1$ is chosen from alkyl and aryl, each optionally substituted with 0, 1 or multiple R$_6$, and R$_2$ is chosen from hydrogen, alkyl, aryl, and acyl, each optionally substituted with 0, 1 or multiple R$_6$. In a more particular embodiment of any of the above embodiments, R$_4$ is —C(O)R$_5$ or —CH$_2$OC(O)R$_5$. In a more particular embodiment of any of the above embodiments, R$_5$ is chosen from alkyl and alkoxy, each optionally substituted with 0, 1, or multiple R$_6$. In a more particular embodiment of any of the above embodiments, R$_1$ is chosen from alkyl and aryl, each optionally substituted with 0, 1 or multiple R$_6$. In a more particular embodiment of any of the above embodiments, R$_2$ is chosen from hydrogen, alkyl, aryl, and acyl, each optionally substituted with 0, 1 or multiple R$_6$. In a more particular embodiment of any of the above embodiments, R$_1$ is chosen from alkyl and aryl, each optionally substituted with 0, 1 or multiple R$_6$, and R$_2$ is chosen from hydrogen, alkyl, aryl, and acyl, each optionally substituted with 0, 1 or multiple R$_6$. In a more particular embodiment of any of the above embodiments, R$_5$ is chosen from —CH$_3$, —CH$_2$OCH$_2$CH$_3$, and —CH$_2$CH$_2$OCH$_3$.

In another exemplary embodiment, the composition according to any of the above embodiments further includes a phytologically acceptable carrier material.

In another exemplary embodiment, the composition according to any of the above embodiments further includes another pesticide. Exemplary pesticides include fungicides, insecticides, nematocides, miticides, arthropodicides, bactericides and combinations thereof.

In a more particular embodiment of any of the above embodiments, the fungal pathogen is one of Leaf Blotch of Wheat (*Mycosphaerella graminicola*; anamorph: *Septoria tritici*), Wheat Brown Rust (*Puccinia triticina*), Stripe Rust (*Puccinia striiformis*), Scab of Apple (*Venturia inaequalis*), Blister Smut of Maize (*Ustilago maydis*), Powdery Mildew of Grapevine (*Uncinula necator*), Barley scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f sp. *tritici*), Powdery Mildew of Barley (*Blumeria graminis* f sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*). In an even more particular embodiment, the fungal pathogen is one of Leaf Blotch of Wheat (*Septoria tritici*), Wheat Brown Rust (*Puccinia triticina*), and Rust of Soybean (*Phakopsora pachyrhizi*).

In another exemplary embodiment, a method for the control and prevention of fungal attack on a plant is provided. The method includes applying a fungicidally effective amount of at least one of any of the above compositions to at least one of the plant, an area adjacent to the plant, soil adapted to support growth of the plant, a root of the plant, and foliage of the plant.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyraflu-prole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; impect stage: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f sp. *tritici*), powdery mildew of barley (*Blumeria graminis* f sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Compounds of Formula 1.5, where $R_1$ is as originally defined, can be prepared according to the methods outlined in Scheme 1, steps a-g. Compounds of Formula 1.1, where $R_1$ is as originally defined, can be obtained by reaction of the dianion of an ester of Formula 1.0 formed by treatment with lithium diisopropyl amide (LDA) at −50° C., with an alkyl halide or allyl halide in a solvent such as tetrahydrofuran (THF) at cryogenic temperatures such as −78° C., as shown in a. Compounds of Formula 1.2, where $R_1$ is as originally defined, can be obtained by treating compounds of Formula 1.1, where $R_1$ is an alkenyl functionality, with hydrogen gas in the presence of a catalyst such as palladium on carbon (Pd/C) in a solvent such as ethyl acetate (EtOAc), as shown in b. Compounds of Formula 1.3, where $R_1$ is as originally defined, can be prepared from compounds of Formula 1.1, where $R_1$ is as defined above, and Formula 1.2, where $R_1$ is as defined above, by treating with an alkylating agent such as 4-methoxybenzyl 2,2,2-trichloroacetimidate in the presence of an acid such as camphor sulfonic acid (CSA) in a solvent such as dichloromethane (DCM), as depicted in c. Aldehydes of Formula 1.4, where $R_1$ is as originally defined, can be obtained by the reduction of esters of Formula 1.3, where $R_1$ is as defined above, using a catalyst such as chlorobis(cyclooctene)iridium(I) dimer in the presence of a reducing agent such as diethylsilane ($Et_2SiH$) in a solvent such as DCM, as shown in d. Aldehydes of Formula 1.4, where $R_1$ is as originally defined, can also be obtained by reduction of esters of Formula 1.3, where $R_1$ is as defined above, using hydride reducing agents, such as lithium aluminum hydride ($LiAlH_4$, LAH) in ethereal solvents, giving alcohols of Formula 1.6, where $R_1$ is as defined above, as depicted in e. Oxidation of alcohols of Formula 1.6, where $R_1$ is as defined above, using oxidation reagents such as sulfur trioxide-pyridine complex ($SO_3$-pyridine/dimethyl sulfoxide (DMSO)) in solvents such as DCM, furnish the aldehydes of Formula 1.4, where $R_1$ is as originally defined, as depicted in f. The addition of metallated alkenes such as vinyl magnesium bromide to aldehydes of Formula 1.4, where $R_1$ is as defined above, in a solvent such as THF at −78° C., affords allylic alcohols of Formula 1.5, where $R_1$ is as originally defined, as depicted in g.

Scheme 1

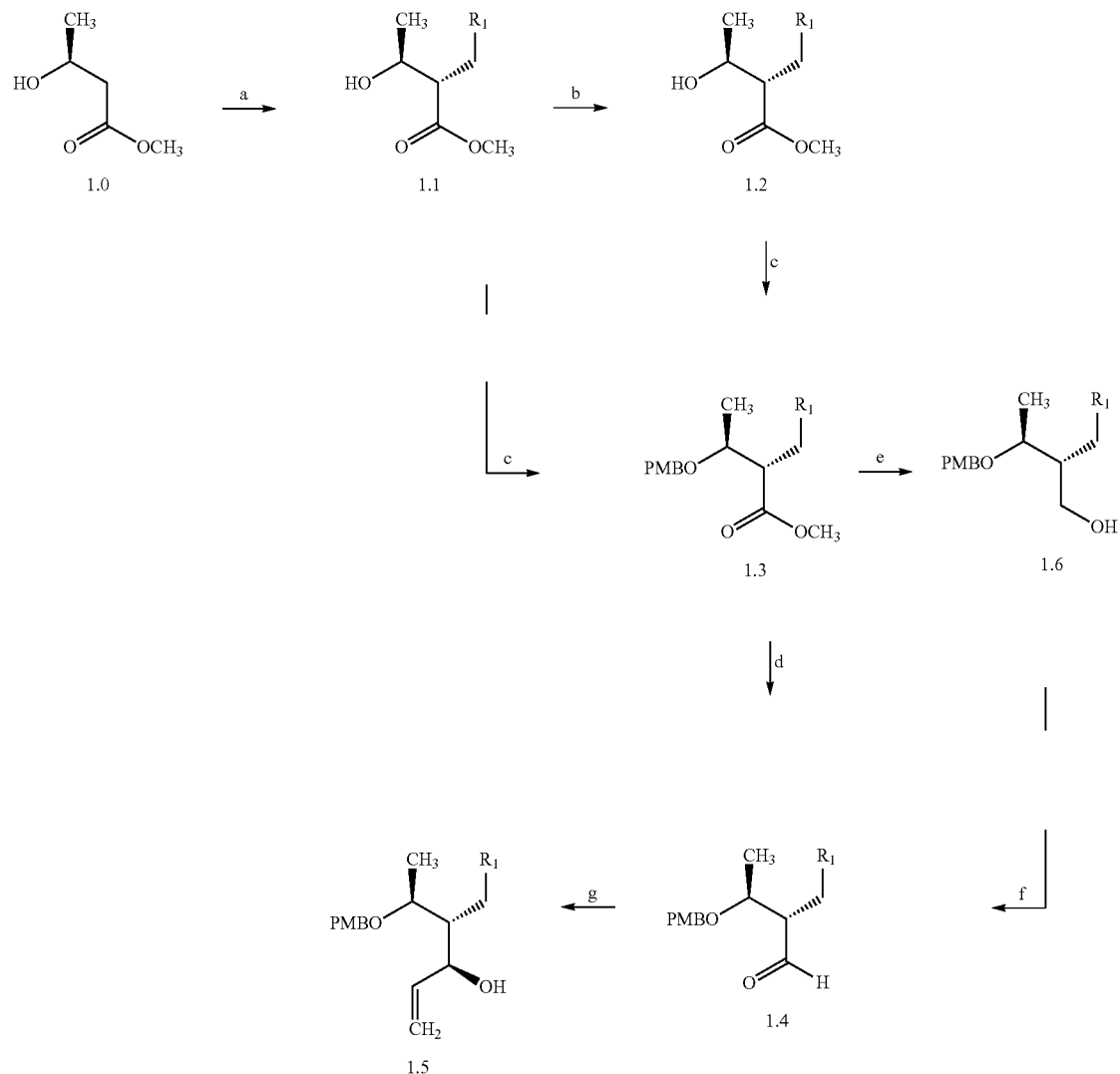

Compounds of Formulas 2.0 and 2.1, where $R_1$ and $R_2$ are as originally defined, but $R_2$ is not acyl or hydrogen, can be prepared as shown in Scheme 2, steps a-b. Alcohols of Formula 1.5, where $R_1$ is as originally defined, can be alkylated to give compounds of Formula 2.0, where $R_1$ and $R_2$ are as defined above, by deprotonation with a base such as sodium hydride (NaH) in an aprotic solvent such as N,N-dimethylformamide (DMF), followed by treatment with an alkylating agent, such as cyclopropylmethyl bromide, at an elevated temperature such as 50° C., as shown in a. Alternatively, alcohols of Formula 1.5, where $R_1$ is as defined above, can be arylated by treating with an arylating agent such as triphenylbismuth(V)diacetate in the presence of a copper catalyst such as diacetoxycopper and a base such as N,N-dicyclohexyl-N-methylamine in a solvent such as toluene at an elevated temperature such as 60° C. to give compounds of Formula 2.1, where $R_1$ and $R_2$ are as defined above, as depicted in b.

Scheme 2

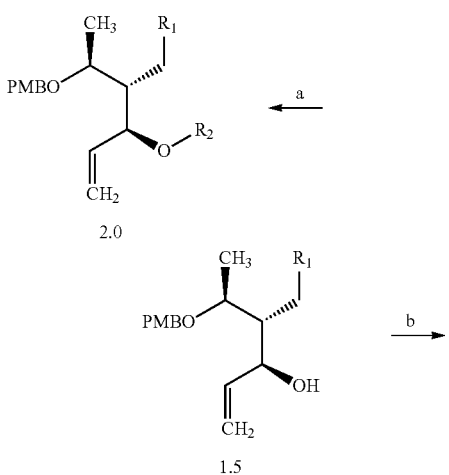

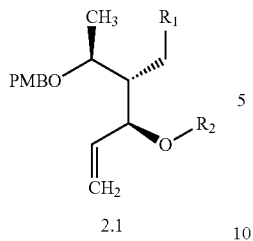

2.1

Compounds of Formula 3.5, where $R_1$ and $R_2$ are as originally defined, but $R_2$ is not acyl or hydrogen, can be prepared according to the methods outlined in Scheme 3, steps a-d. Alcohols of Formula 3.1, where $R_1$ and $R_2$ are as originally defined, but $R_2$ is not acyl or hydrogen, can be obtained from compounds of Formula 3.0, where $R_1$ and $R_2$ are as originally defined, but $R_2$ is not acyl or hydrogen, by ozonolysis at a cryogenic temperature such as −78° C. in a solvent mixture such as DCM and methanol (MeOH), followed by treating with a reducing agent such as sodium borohydride (NaBH$_4$), as shown in a. Alcohols of Formula 3.1, where $R_1$ and $R_2$ are as defined above, can be treated with protected aziridines of Formula 3.2 in the presence of a Lewis acid such as boron trifluoride-diethyl etherate (BF$_3$-Et$_2$O) at 0° C., in a halogenated solvent such as DCM, as shown in b, to afford compounds of Formula 3.3, where $R_1$ and $R_2$ are as originally defined, but $R_2$ is not acyl or hydrogen. Compounds of Formula 3.4, where $R_1$ and $R_2$ are as originally defined, but $R_2$ is not acyl or hydrogen, can be obtained from compounds of Formula 3.3, where $R_1$ and $R_2$ are as defined above, by treating with an oxidant such as 2,3-dichloro-5,6-dicyano-p-benzoquinone (DDQ) in a solvent mixture such as DCM and water, as shown in c. Treating compounds of Formula 3.4, where $R_1$ and $R_2$ are as defined above, with a hydroxide base such as lithium hydroxide (LiOH) in a solvent mixture such as THF and water, as depicted in d, provides compounds of Formula 3.5, where $R_1$ and $R_2$ are as defined above.

Scheme 3

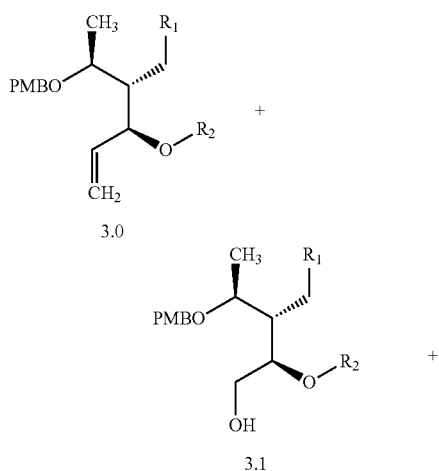

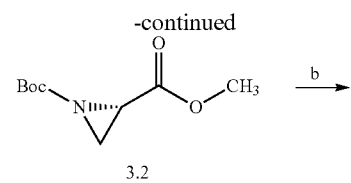

3.2

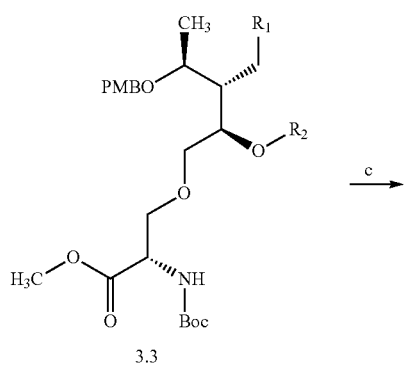

3.3

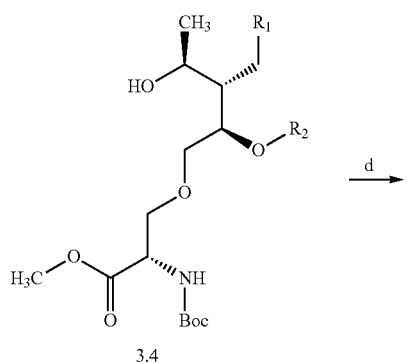

3.4

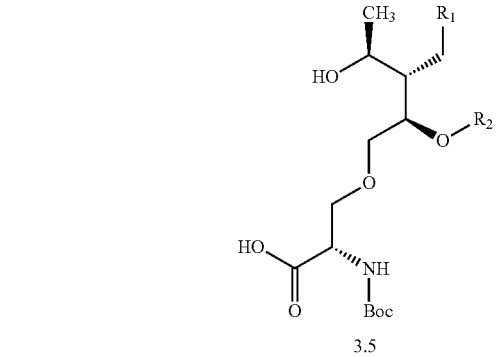

3.5

Compounds of Formula 4.0, where $R_1$ and $R_2$ are as originally defined, but $R_2$ is not acyl or hydrogen, can be prepared according to the methods outlined in Scheme 4. Compounds of Formula 4.0, where $R_1$ and $R_2$ are as defined above, can be obtained by the addition of a solution of compounds of Formula 3.5, where $R_1$ and $R_2$ are as originally defined, but $R_2$ is not acyl or hydrogen, in a halogenated solvent such as DCM to a mixture of a base, such as 4-dimethylaminopyridine (DMAP), and a mixed anhydride, such as 2-methyl-6-nitrobenzoic anhydride (MNBA), in an aprotic solvent such as DCM over a period of 4-12 hours, as shown in a.

Scheme 4

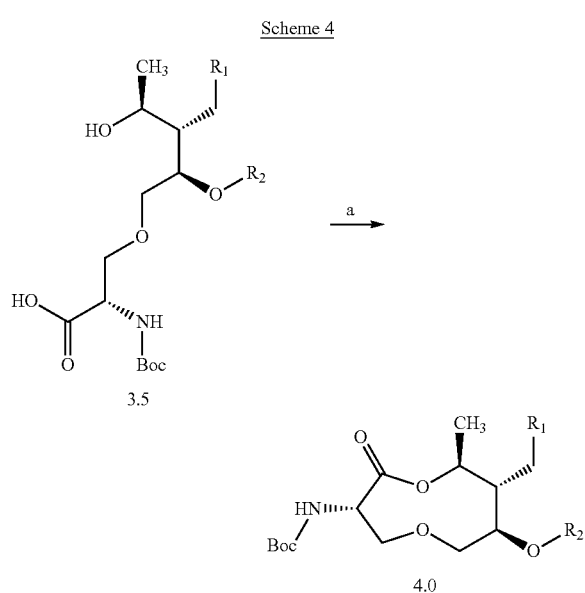

Compounds of Formula 5.2, where $R_1$ is as originally defined and $R_2$ is acyl, can be prepared according to the methods outlined in Scheme 5, steps a-b. Compounds of the Formula 5.1, where $R_1$ is as originally defined, can be prepared from compounds of Formula 5.0, where $R_1$ is as originally defined and $R_2$ is benzyl, by hydrogenolysis using a metal catalyst such as palladium on carbon (Pd/C) in the presence of hydrogen gas. Compounds of Formula 5.2, where $R_1$ and $R_2$ are as defined above, can be prepared from compounds of Formula 5.1, where $R_1$ and $R_2$ are as defined above, by reacting with an acylating agent such as cyclopropanecarbonyl chloride in the presence of base such as triethylamine (TEA) and DMAP in a halogenated solvent such as DCM.

Compounds of Formula 6.3, where $R_1$ and $R_2$ are as originally defined, but $R_2$ is not hydrogen, can be prepared through the methods shown in Scheme 6, steps a-c. Compounds of Formula 6.1, where $R_1$ and $R_2$ are as originally defined, but $R_2$ is not hydrogen, can be prepared by treating compounds of Formula 6.0, where $R_1$ and $R_2$ are as defined above, but $R_2$ is not hydrogen or an alkoxy moiety, with an acid, such as a 4.0 Molar (M) hydrogen chloride (HCl) solution in dioxane, in a solvent such as DCM, as shown in a. The resulting hydrochloride salt may be neutralized prior to use to give the free amine or neutralized in situ in step c. Compounds of Formula 6.2. where $R_1$ is as defined above and $R_2$ is an alkyl substituted with an alkoxy moiety, can be prepared from compounds of Formula 6.1, where $R_1$ and $R_2$ are as defined above, by treating with trimethylsilyl trifluoromethanesulfonate and a base such as 2,6-lutidine in a halogenated solvent DCM, followed by quenching with MeOH as shown in b. The resulting triflate salt may be neutralized prior to use to give the free amine or neutralized in situ in step c. Compounds of Formula 6.3, where $R_1$ and $R_2$ are as defined above, can be prepared from compounds of Formula 6.1, where $R_1$ and $R_2$ are as defined above, or from compounds of Formula 6.2, where $R_1$ and $R_2$ are as defined above, by treatment with 3-hydroxy-4-methoxypicolinic acid in the presence of a base, such as diisopropylethylamine, and a peptide coupling reagent, such as benzotriazol-1-yl-oxytripyrrolidinophosphonium hexafluorophosphate (PyBOP) or O-(7-azabenzotriazol-1-yl)-N,N,N',N'-tetramethyluronium hexafluorophosphate (HATU), in an halogenated solvent such as DCM, as shown in c.

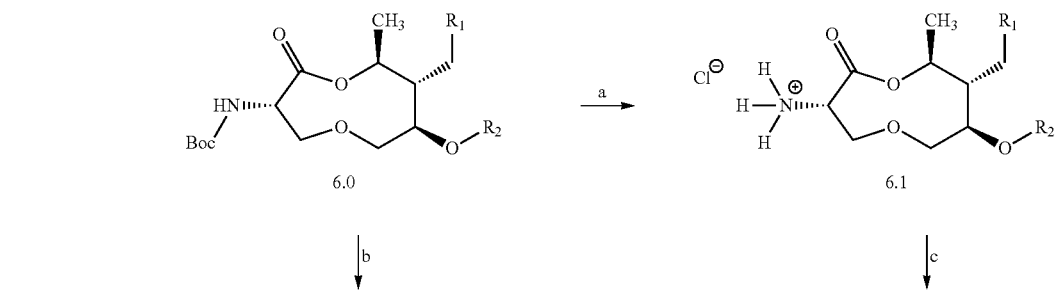

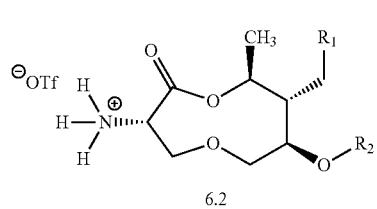
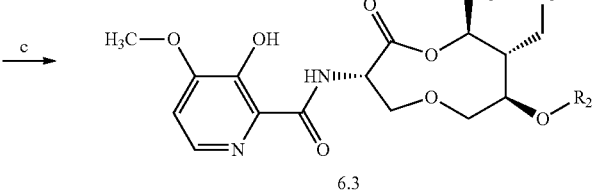

-continued

Compounds of Formula 7.0, where $R_1$, $R_2$ and $R_4$ are as originally defined, but $R_2$ is not hydrogen, can be prepared by the method shown in Scheme 7. Compounds of Formula 7.0, where $R_1$, $R_2$, and $R_4$ are as defined above, can be prepared from compounds of Formula 6.3, where $R_1$ and $R_2$ are as originally defined, but $R_2$ is not hydrogen, by treatment with the appropriate alkyl halide with or without a reagent such as sodium iodide (NaI) and an alkali carbonate base such as sodium carbonate ($Na_2CO_3$) or potassium carbonate ($K_2CO_3$) in a solvent such as acetone or by treatment with an acyl halide in the presence of an amine base, such as pyridine, TEA, DMAP, or mixtures thereof in an aprotic solvent such as DCM, as shown in a.

Scheme 7

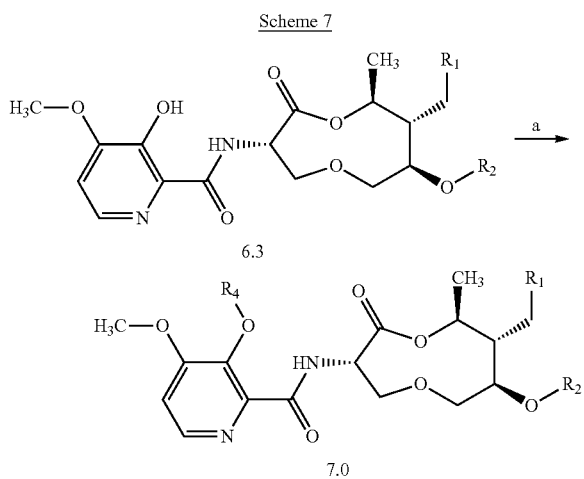

EXAMPLES

Example 1, Step 1: Preparation of (S)-methyl 2-((S)-1-hydroxyethyl)-5-methylhex-4-enoate

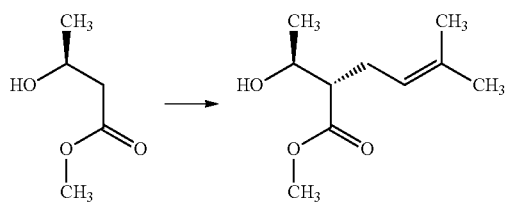

To a solution of diisopropylamine (19.93 milliliters (mL), 142 millimoles (mmol)) in anhydrous THF (99 mL) at −50° C. (deficient dry ice/acetone bath) was added n-butyllithium (n-BuLi; 54.3 mL, 130 mmol, 2.5 M in hexanes). This solution was removed from the cold bath for 15 minutes (min), then re-cooled to −50° C. To the lithium diisopropylamide (LDA) was added a solution of (S)-methyl 3-hydroxybutanoate (6.64 ml, 59.3 mmol) in THF (20.0 mL) dropwise over 15 min using a cannula. This solution was allowed to warm to −30° C. over 30 min, stirred at −30° C. for 1 h, and recooled to −78° C. To the enolate was added a solution of 1-bromo-3-methylbut-2-ene (13.7 mL, 119 mmol) in anhydrous 1,2-dimethoxyethane (20.0 mL, 193 mmol) dropwise over 15 min. The cold bath was at −60° C. after 1 h at which time the reaction flask was removed from the bath and stirred without cooling for 1.5 h. The reaction was quenched by the addition of sat. aq. ammonium chloride ($NH_4Cl$; 50 mL), diluted with EtOAc (50 mL), and the phases were separated. The aqueous phase was further extracted with EtOAc (2×50 mL) and the combined organic extracts were washed with sat. aq. sodium chloride (NaCl, brine; 50 mL), dried over sodium sulfate $Na_2SO_4$, filtered, and concentrated to dryness. The crude residue was purified by flash column chromatography (120 grams (g) silica gel ($SiO_2$), 0→40% EtOAc/hexanes) to afford the title compound (9.5 g, 51.0 mmol, 86%) as a slightly yellow oil: IR (thin film) 3452, 2971, 2929, 1730, 1437, 1198, 1160 cm$^{-1}$; $^1$H NMR (400 MHz, CDCl$_3$) δ 5.11-5.01 (m, 1H), 3.92 (p, J=6.3 Hz, 1H), 3.70 (s, 3H), 2.78 (s, 1H), 2.46-2.28 (m, 3H), 1.69 (d, J=1.4 Hz, 3H), 1.62 (s, 3H), 1.23 (d, J=6.4 Hz, 3H); $^{13}$C NMR (101 MHz, CDCl$_3$) δ 175.54, 134.14, 120.30, 67.78, 52.72, 51.52, 27.90, 25.73, 21.46, 17.64.

Example 1, Step 2: Preparation of (S)-methyl 2-((S)-1-hydroxyethyl)-5-methylhexanoate

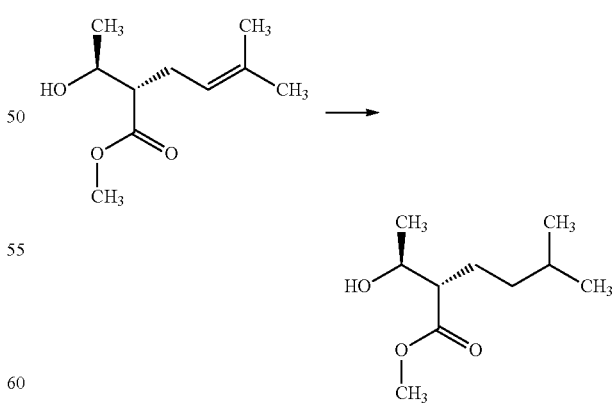

To a well stirred solution of (S)-methyl 2-((S)-1-hydroxyethyl)-5-methylhex-4-enoate (9.5 g, 51.0 mmol) in MeOH (51 mL) was added 10% Pd/C (0.543 g, 5.10 mmol). The reaction was put under a hydrogen atmosphere (balloon) and stirred at room temperature for 20 h. The mixture was filtered through a plug of Celite® and the plug was washed with MeOH (20 mL). The filtrate and washes were combined, the solvent was removed under reduced pressure, and the residue was dissolved in DCM (50 mL). The solution was passed through a phase separator to remove residual water ($H_2O$), and the solvent was removed under reduced pressure to afford the title compound (9.45 g, 50.2 mmol, 98%) as a slightly yellow oil: IR (thin film) 3451, 2954, 2871, 1736, 1719, 1169 $cm^{-1}$; $^1H$ NMR (400 MHz, $CDCl_3$) δ 3.91 (p, J=6.4 Hz, 1H), 3.72 (s, 3H), 2.77 (s, 1H), 2.36 (ddd, J=9.2, 6.3, 5.0 Hz, 1H), 1.72-1.45 (m, 3H), 1.28-1.05 (m, 5H), 0.88 (dd, J=6.6, 3.2 Hz, 6H); $^{13}C$ NMR (75 MHz, $CDCl_3$) δ 176.13, 68.55, 53.29, 51.67, 36.55, 28.16, 27.37, 22.74, 22.44, 21.68.

Example 1, Step 3: Preparation of (S)-methyl 2-((S)-1-((4-methoxybenzyl)oxy)ethyl)-5-methylhexanoate

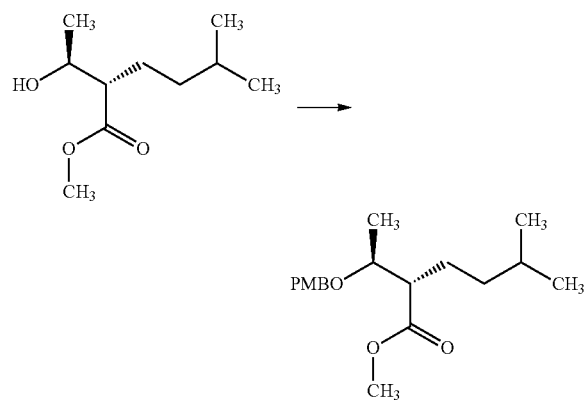

To a solution of (S)-methyl 2-((S)-1-hydroxyethyl)-5-methylhexanoate (5.00 g, 26.6 mmol) and ((1S,4R)-7,7-dimethyl-2-oxobicyclo[2.2.1]heptan-1-yl)methanesulfonic acid (camphorsulfonic acid, CSA; 0.617 g, 2.66 mmol) in DCM (53.1 mL) was added 4-methoxybenzyl 2,2,2-trichloroacetimidate (8.27 mL, 39.8 mmol) at 0° C. The reaction mixture was removed from the cold bath and stirred at room temperature for 17 h. Hexane (50 mL) was added to the reaction and the precipitate was removed by filtration. The solids were washed with hexanes (2×10 mL), Celite® (2 scoopula tip-fulls) was added to the combined filtrate and washes, and the solvent was removed under reduced pressure. The resulting adsorbed material was directly loaded onto a column and purified using flash column chromatography (80 g $SiO_2$, 0→35% EtOAc/hexanes) to afford the title compound (6.3 g, 20.4 mmol, 77%) as a colorless oil; $^1H$ NMR (400 MHz, $CDCl_3$) δ 7.24-7.16 (m, 2H), 6.89-6.79 (m, 2H), 4.49 (d, J=11.2 Hz, 1H), 4.33 (d, J=11.1 Hz, 1H), 3.75 (s, 3H), 3.74-3.62 (m, 4H), 2.49 (ddd, J=10.7, 8.2, 4.0 Hz, 1H), 1.62-1.40 (m, 3H), 1.23-1.16 (m, 3H), 1.16-1.03 (m, 2H), 0.87 (d, J=3.9 Hz, 3H), 0.85 (d, J=3.9 Hz, 3H); $^{13}C$ NMR (101 MHz, $CDCl_3$) δ 175.03, 159.10, 130.63, 129.14, 113.62, 76.16, 70.71, 55.11, 52.64, 51.25, 36.58, 27.97, 26.00, 22.69, 22.17, 17.08; ESIMS m/z 331 ($[M+Na]^+$).

Example 1, Steps 4 and 5: Preparation of (3S,4R)-4-((S)-1-((4-methoxy-benzyl)oxy)ethyl)-7-methyl-oct-1-en-3-ol and (3R,4R)-4-((S)-1-((4-methoxybenzyl)oxy)ethyl)-7-methyloct-1-en-3-ol

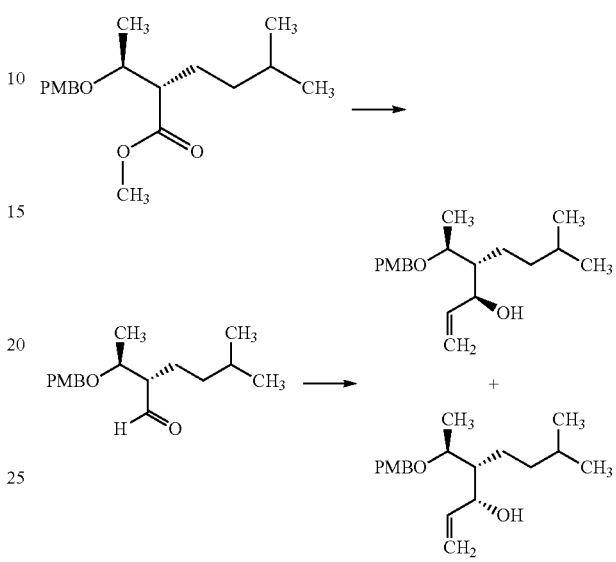

Step 4

To a solution of (S)-methyl 2-((S)-1-((4-methoxybenzyl)oxy)ethyl)-5-methylhexanoate (6.00 g, 19.5 mmol) and chlorobis(cyclooctene)-iridium(I) dimer (0.349 g, 0.389 mmol) in dry DCM (19.5 mL) was slowly added $Et_2SiH$ (3.76 mL, 29.2 mmol) at 0° C. The flask was removed from the cold bath and the reaction was stirred at room temperature for 20 h under nitrogen ($N_2$). The reaction mixture was transferred via cannula to an ice-cooled mixture of diethyl ether ($Et_2O$; 60 mL) and 2 Normal (N) HCl (20 mL) over 15 min. The mixture was removed from the cold bath and stirred at room temperature for 30 min. The phases were separated and the aq. phase was further extracted with $Et_2O$ (2×50 mL). The organics were combined, washed with sat. aq. sodium bicarbonate ($NaHCO_3$; 25 mL) and brine (25 mL), dried over $Na_2SO_4$, filtered, and the filtrate treated with Celite® (5 scoopula tip-fulls). The solvent was removed under reduced pressure and the resulting adsorbed material was directly loaded onto a column and purified using flash column chromatography (120 g $SiO_2$, 07→5% EtOAc/hexanes) to afford the intermediate aldehyde, (S)-2-((S)-1-((4-methoxybenzyl)oxy)ethyl)-5-methylhexanal.

Step 5

The intermediate aldehyde was dissolved in THF (30 mL), the mixture was cooled to −78° C., vinylmagnesium bromide (29.2 mL, 29.2 mmol, 1M in THF) was slowly added, and the resulting solution was stirred for 30 min. The reaction was removed from the cold bath, stirred at room temperature for 30 min, and quenched by the addition of sat. aq. $NH_4Cl$ (30 mL). The phases were separated, and the aq. phase was further extracted with $Et_2O$ (3×50 mL). The combined organics were dried over $Na_2SO_4$, filtered, and concentrated to dryness. The residue was dissolved in DCM (20 mL) and the resulting solution was treated with Celite® (5 scoopula tip-fulls). The solvent was removed under reduced pressure and the resulting adsorbed material was directly loaded onto a column and purified using flash column chromatography (220 g SiO$_2$, 0→15% acetone/hexanes) to afford the individual diastereomers as colorless oils:

(3S,4R)-4-((S)-1-((4-methoxybenzyl)oxy)ethyl)-7-methyloct-1-en-3-ol (2.35 g, 7.67 mmol, 39%): $^1$H NMR (400 MHz, CDCl$_3$) δ 7.27-7.19 (m, 2H), 6.91-6.82 (m, 2H), 5.84 (ddd, J=17.2, 10.6, 4.7 Hz, 1H), 5.29 (app dt, J=17.2, 1.9 Hz, 1H), 5.16 (app dt, J=10.6, 1.9 Hz, 1H), 4.58 (d, J=11.0 Hz, 1H), 4.53-4.45 (m, 1H), 4.27 (d, J=10.9 Hz, 1H), 3.83 (d, J=4.3 Hz, 1H), 3.79 (s, 3H), 3.76-3.65 (m, 1H), 1.52-1.26 (m, 7H), 1.20-1.06 (m, 2H), 0.85 (app dd, J=6.6, 2.2 Hz, 6H); $^{13}$C NMR (101 MHz, CDCl$_3$) δ 159.33, 139.16, 130.02, 129.54, 114.61, 113.88, 76.55, 72.08, 70.65, 55.26, 49.31, 37.35, 28.25, 23.51, 22.63, 22.52, 17.71; ESIMS m/z 329 ([M+Na]$^+$).

(3R,4R)-4-((S)-1-((4-methoxybenzyl)oxy)ethyl)-7-methyloct-1-en-3-ol (1.48 g, 4.83 mmol, 25%): $^1$H NMR (400 MHz, CDCl$_3$) δ 7.30-7.22 (m, 2H), 6.91-6.83 (m, 2H), 5.89 (ddd, J=17.1, 10.3, 6.7 Hz, 1H), 5.24 (ddd, J=17.2, 1.8, 1.2 Hz, 1H), 5.12 (ddd, J=10.4, 1.8, 1.1 Hz, 1H), 4.58 (d, J=11.1 Hz, 1H), 4.35 (d, J=11.1 Hz, 1H), 4.22-4.13 (m, 1H), 3.80 (s, 3H), 3.70 (p, J=6.3 Hz, 1H), 3.66 (d, J=3.2 Hz, 1H), 1.56 (tt, J=6.8, 5.2 Hz, 1H), 1.49-1.24 (m, 6H), 1.19-1.08 (m, 2H), 0.84 (dd, J=6.7, 2.0 Hz, 6H); $^{13}$C NMR (101 MHz, CDCl$_3$) δ 159.24, 140.20, 130.22, 129.41, 115.17, 113.87, 78.10, 75.83, 70.43, 55.28, 48.98, 36.07, 28.53, 26.08, 22.52, 17.93; ESIMS m/z 329 ([M+Na]$^+$).

Example 1, Step 6: Preparation of (2R,3S)-2-benzyl-3-((4-methoxybenzyl)-oxy)butan-1-ol

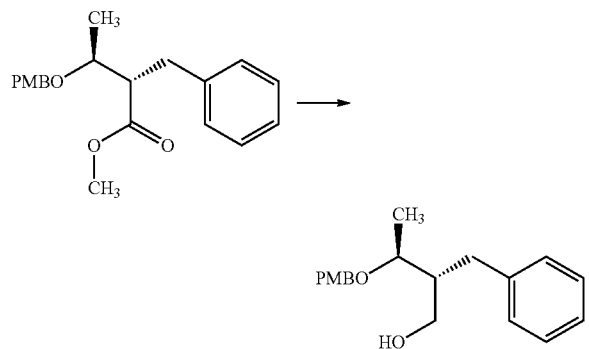

To a stirred suspension of LAH in anhydrous Et$_2$O (140 mL) was added (2S,3S)-methyl 2-benzyl-3-((4-methoxybenzyl)oxy)butanoate dissolved in Et$_2$O (104 mL) dropwise at 0° C. The reaction was stirred at 0° C. for 15 min, followed by warming to room temperature and stirring for 1 h. The reaction was recooled to 0° C. and carefully quenched by the simultaneous dropwise addition of H$_2$O (2.8 mL) and 1N sodium hydroxide (NaOH; 2.8 mL). The mixture was filtered and the aluminum salts were washed with Et$_2$O (50 mL). The filtrate was treated with Celite® (20 g) and concentrated to give a solid. The adsorbed material was purified using flash column chromatography (120 g SiO$_2$ column, 0→60% EtOAc/hexane) to afford the title compound (5.38 g, 74%) as a clear oil: $^1$H NMR (400 MHz, CDCl$_3$) δ 7.30-7.10 (m, 7H), 6.93-6.84 (m, 2H), 4.59 (d, J=11.2 Hz, 1H), 4.30 (d, J=11.2 Hz, 1H), 3.89 (app dt, J=11.4, 2.9 Hz, 1H), 3.80 (s, 3H), 3.66 (app qd, J=6.2, 4.3 Hz, 1H), 3.50 (ddd, J=11.5, 6.9, 4.7 Hz, 1H), 2.93-2.85 (m, 1H), 2.75 (app qd, J=13.7, 7.5 Hz, 2H), 1.76 (dddt, J=10.9, 6.6, 4.3, 2.3 Hz, 1H), 1.29 (d, J=6.3 Hz, 3H); $^{13}$C NMR (101 MHz, CDCl$_3$) δ 159.32, 140.61, 130.35, 129.39, 129.20, 128.36, 125.97, 113.93, 70.70, 62.36, 55.31, 47.81, 35.11, 17.67; ESIMS m/z 323 ([M+Na]$^+$).

Example 1, Step 7: (2S,3S)-2-benzyl-3-((4-methoxybenzyl)oxy)butanal

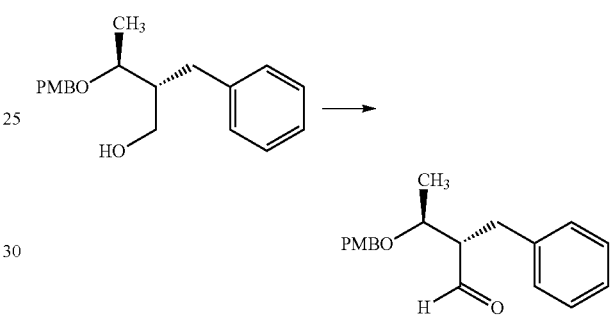

To a solution of (2R,3S)-2-benzyl-3-((4-methoxybenzyl)oxy)butan-1-ol (5.38 g, 17.91 mmol) in CH$_2$Cl$_2$ (90 mL) in a nitrogen flushed 250 mL round bottomed flask was added DMSO (17.9 mL, 25.24 mmol) and TEA (12.5 mL, 90 mmol) via syringe followed by sulfur trioxode-pyridine complex (8.55 g, 53.7 mmol) in three equal portions at 0° C. under N$_2$. The reaction was removed from the cold bath and allowed to warm to room temperature, and stirred for 2 h. The reaction was diluted with ice cold 0.5 N HCl (100 mL) and EtOAc (150 mL). The phases were separated and the organic phase was washed with sat. aq. NaHCO$_3$ (50 mL) and brine (50 mL). The solution was dried over magnesium sulfate (MgSO$_4$), filtered, and concentrated to afford the title compound (5.3 g, 96%) as a yellow oil: $^1$H NMR (400 MHz, CDCl$_3$) δ 9.78 (d, J=2.8 Hz, 1H), 7.29-7.09 (m, 7H), 6.89 (d, J=8.7 Hz, 2H), 4.56 (d, J=11.3 Hz, 1H), 4.34 (d, J=11.3 Hz, 1H), 3.82 (s, 3H), 3.03 (dd, J=14.0, 8.2 Hz, 1H), 2.87 (dd, J=14.0, 6.4 Hz, 2H), 2.78-2.55 (m, 1H), 1.29 (d, J=6.4 Hz, 3H); ESIMS m/z 321.3 ([M+Na]$^+$).

Example 1, Step 8: Preparation of (3S,4R,5S)-4-benzyl-5-(4-methoxybenzyl)oxy)-hex-1-en-3-ol

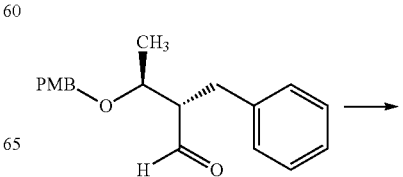

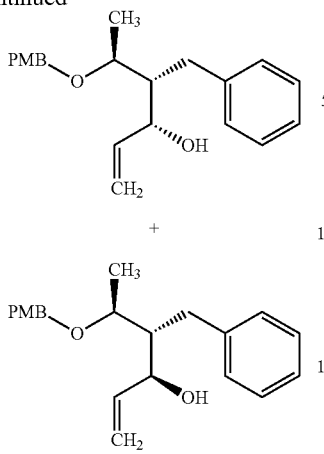

To a 200 mL round-bottomed flask equipped with a magnetic stir bar were added (2S,3S)-2-benzyl-3-((4-methoxybenzyl)oxy)butanal (5.34 g, 17.90 mmol) and THF (36 mL). The flask was cooled to −78° C. and vinylmagnesium bromide (1.0 M in THF, 36 mL, 36 mmol) was added via a syringe. The reaction was maintained at −78° C. for 1.5 h, quenched with sat. aq. NH$_4$Cl (25 mL) at −78° C., and then removed from the cold bath. After warming to room temperature, the biphasic mixture was diluted with EtOAc (100 mL), and the phases were separated. The organic phase was washed with brine (30 mL), dried over MgSO$_4$, filtered, and concentrated. The oil was purified by flash column chromatography (120 g SiO$_2$ column, 0→100% EtOAc/hexanes) to afford the pure desired isomer (1.18 g), and a mixture of the isomers (2.53 g). The mixture was re-purified by flash column chromatography (80 g SiO$_2$ column, 0→15% acetone/hexanes) to afford clean separation of the isomers in a 2.23:1 ratio of diastereomers.

(3S,4R,5S)-4-Benzyl-5-((4-methoxybenzyl)oxy)hex-1-en-3-ol (2.88 g, 49%): $^1$H NMR (400 MHz, CDCl$_3$) δ 7.28-7.17 (m, 5H), 7.05-6.98 (m, 2H), 6.92-6.84 (m, 2H), 5.91 (ddd, J=17.1, 10.6, 4.4 Hz, 1H), 5.36 (dt, J=17.2, 1.9 Hz, 1H), 5.23 (dt, J=10.6, 1.8 Hz, 1H), 4.65-4.59 (m, 1H), 4.56 (d, J=10.9 Hz, 1H), 4.21 (d, J=11.0 Hz, 1H), 3.89 (d, J=2.7 Hz, 1H), 3.78 (s, 3H), 3.65 (qd, J=6.3, 3.7 Hz, 1H), 2.72 (d, J=7.3 Hz, 2H), 1.78-1.70 (m, 1H), 1.25 (d, J=6.2 Hz, 3H); $^{13}$C NMR (101 MHz, CDCl$_3$) δ 159.46, 141.10, 139.22, 130.09, 129.57, 129.23, 128.39, 125.91, 115.02, 114.01, 75.38, 70.99, 70.74, 55.33, 50.95, 31.46, 17.72; ESIMS m/z 349 ([M+Na]$^+$).

(3R,4R,5S)-4-Benzyl-5-((4-methoxybenzyl)oxy)hex-1-en-3-ol (1.3 g, 22%): $^1$H NMR (300 MHz, CDCl$_3$) δ 7.33-7.04 (m, 7H), 6.96-6.78 (m, 2H), 5.96 (ddd, J=17.2, 10.4, 5.5 Hz, 1H), 5.25 (dt, J=17.2, 1.7 Hz, 1H), 5.11 (dt, J=10.5, 1.6 Hz, 1H), 4.56 (d, J=11.4 Hz, 1H), 4.31 (d, J=11.4 Hz, 1H), 4.28-4.22 (m, 1H), 3.82 (s, 3H), 3.72-3.65 (m, 1H), 2.86-2.87 (m, 3H), 2.06-1.96 (m, 1H), 1.27 (d, J=6.4 Hz, 3H): ESIMS m/z 349.3 ([M+Na]$^+$).

Example 2, Step 1: Preparation of 1-methoxy-4-(((((2S,3S)-6-methyl-3-((S)-1-phenoxyallyl)heptan-2-yl)oxy)methyl)benzene

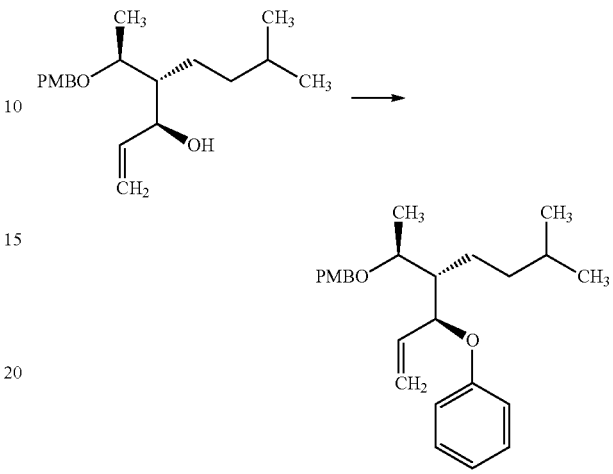

A toluene (12.0 mL) solution of (3S,4R)-4-((S)-1-((4-methoxybenzyl)oxy)ethyl)-7-methyloct-1-en-3-ol (1.10 g, 3.59 mmol), N-cyclohexyl-N-methylcyclohexanamine (1.14 mL, 5.38 mmol), triphenylbismuth diacetate (3.01 g, 5.38 mmol), and copper(II) acetate (0.130 g, 0.718 mmol) was heated to 50° C. and stirred at this temperature for 16 h. Additional triphenylbismuth diacetate (1.00 g) was added to push the reaction to completion, and after a total reaction time of 38 h, the reaction mixture was cooled to room temperature, loaded onto a Celite® plug and purified by flash column chromatography (40 g SiO$_2$, 0→15% EtOAc/hexanes) to afford the title compound (1.10 g, 2.30 mmol, 64%): $^1$H NMR (400 MHz, CDCl$_3$) δ 7.29-7.20 (m, 3H), 6.99-6.86 (m, 4H), 6.76-6.68 (m, 2H), 5.85 (ddd, J=17.4, 10.8, 4.8 Hz, 1H), 5.27-5.16 (m, 2H), 5.09 (ddt, J=4.8, 3.2, 1.7 Hz, 1H), 4.39 (d, J=10.6 Hz, 1H), 4.09 (d, J=10.6 Hz, 1H), 3.76 (s, 3H), 3.64 (dq, J=8.0, 6.2 Hz, 1H), 1.68-1.56 (m, 2H), 1.55-1.42 (m, 1H), 1.41-1.17 (m, 6H), 0.88 (app dd, J=6.6, 1.4 Hz, 6H); ESIMS m/z 405 ([M+Na]$^+$).

Example 2, Step 2: Preparation of 1-methoxy-4-(((((2S,3S)-6-methyl-3-((S)-1-propoxyallyl)heptan-2-yl)oxy)methyl)benzene

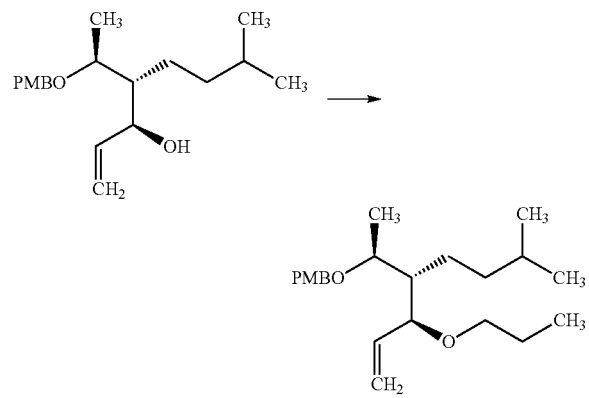

To a solution of (3S,4R)-4-((S)-1-((4-methoxybenzyl)oxy)ethyl)-7-methyloct-1-en-3-ol (1.40 g, 4.57 mmol) and potassium 2-methylpropan-2-olate (0.564 g, 5.03 mmol) in THF (30.5 mL) was added propyl 4-methylbenzenesulfonate (2.15 mL, 11.4 mmol). The reaction was stirred at room temperature for 72 h, diluted with H$_2$O (15 mL), and the phases were separated. The aq. phase was further extracted with Et$_2$O (3×25 mL), and the combined organics were washed with brine (15 mL), dried over Na$_2$SO$_4$, filtered, and the filtrate was treated with Celite® (4 scoopula tip-fulls). The solvent was removed under reduced pressure and the resulting adsorbed material was directly loaded onto a column and purified using flash column chromatography (80 g SiO$_2$, 0→15% EtOAc/hexanes) to afford the title compound (1.30 g, 3.36 mmol, 74%) as a colorless oil: $^1$H NMR (400 MHz, CDCl$_3$) δ 7.30-7.22 (m, 2H), 6.91-6.83 (m, 2H), 5.77-5.63 (m, 1H), 5.20-5.14 (m, 1H), 5.13 (d, J=1.1 Hz, 1H), 4.50-4.35 (m, 2H), 3.85-3.77 (m, 4H), 3.61 (p, J=6.3 Hz, 1H), 3.43 (app tt, J=9.8, 6.6 Hz, 1H), 3.12 (app dt, J=9.1, 6.6 Hz, 1H), 1.69-1.20 (m, 8H), 1.15 (d, J=6.3 Hz, 3H), 0.91 (t, J=7.4 Hz, 3H), 0.87 (app dd, J=6.6, 1.1 Hz, 6H); $^{13}$C NMR (101 MHz, CDCl$_3$) δ 158.98, 138.54, 131.33, 129.16, 116.04, 113.69, 81.66, 75.17, 70.57, 70.12, 55.26, 47.97, 38.70, 28.65, 23.69, 23.24, 22.63, 16.76, 10.90; ESIMS m/z 371 ([M+Na]$^+$).

Example 2, Step 3: Preparation of 1-((((2S,3S)-3-((S)-1-(benzyloxy)allyl)-6-methylheptan-2-yl)oxy)methyl)-4-methoxybenzene

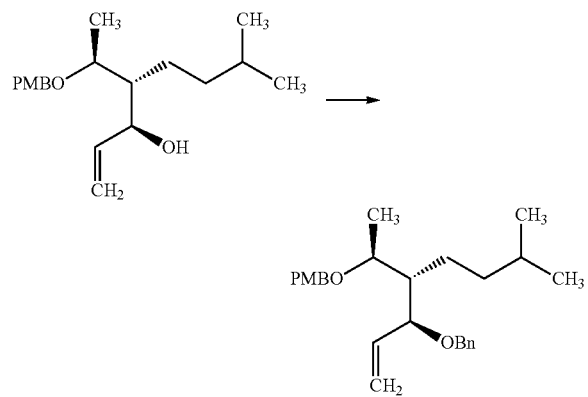

To a solution of (3S,4R)-4-((S)-1-((4-methoxybenzyl)oxy)ethyl)-7-methyloct-1-en-3-ol (2.34 g, 7.64 mmol) in DMF (15.3 mL) was added NaH (0.611 g, 15.3 mmol, 60% dispersion in mineral oil) at 0° C. After 20 min, benzyl bromide (2.27 mL, 19.1 mmol) was added and the reaction was stirred at 0° C. for 20 min, warmed to 45° C., and stirred at this temperature for 16 h. The reaction was cooled to room temperature and quenched with sat. aq. NH$_4$Cl (40 mL). The mixture was extracted with Et$_2$O (3×50 mL), and the combined organics were washed with brine (40 mL), dried over Na$_2$SO$_4$, filtered, and concentrated to dryness. The residue was purified using flash column chromatography (120 g SiO$_2$, 0→20% EtOAc/hexanes) to afford the title compound (2.75 g, 6.93 mmol, 91%) as a colorless oil: $^1$H NMR (400 MHz, CDCl$_3$) δ 7.38-7.34 (m, 2H), 7.32-7.25 (m, 3H), 7.22-7.17 (m, 2H), 6.87-6.78 (m, 2H), 5.78 (ddd, J=17.4, 9.9, 7.3 Hz, 1H), 5.27-5.18 (m, 2H), 4.58 (d, J=12.4 Hz, 1H), 4.42 (d, J=11.2 Hz, 1H), 4.29 (d, J=11.2 Hz, 1H), 4.26 (d, J=11.9 Hz, 1H), 4.04-3.96 (m, 1H), 3.77 (s, 3H), 3.64 (p, J=6.3 Hz, 1H), 1.73-1.63 (m, 1H), 1.55-1.42 (m, 2H), 1.43-1.21 (m, 3H), 1.15 (d, J=6.3 Hz, 3H), 0.86 (d, J=6.6 Hz, 6H); $^{13}$C NMR (101 MHz, CDCl$_3$) δ 158.92, 139.07, 137.94, 131.19, 129.17, 128.19, 127.77, 127.47, 116.82, 113.65, 81.13, 75.03, 70.36, 70.07, 55.22, 48.17, 38.66, 28.62, 23.67, 22.61, 16.84; ESIMS m/z 419 ([M+Na]$^+$).

Example 3, Step 1. Preparation of (2R,3S)-3-((S)-1-((4-methoxybenzyl)oxy)ethyl)-6-methyl-2-propoxyheptan-1-ol

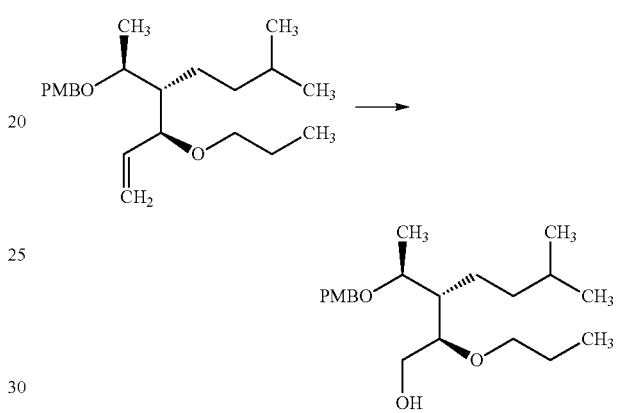

To a solution of 1-methoxy-4-(((((2S,3S)-6-methyl-3-((S)-1-propoxyallyl)heptan-2-yl)oxy)methyl)benzene (710 mg, 2.04 mmol) in DCM (20 mL) and MeOH (5 mL) were added NaHCO$_3$ (34.2 mg, 0.407 mmol) and 1-((E)-(4-((E)-phenyldiazenyl)phenyl)diazenyl)-naphthalen-2-ol (two drops, as a 1% w/v solution in DCM). The resulting faint-pink colored reaction mixture was cooled to −78° C. (dry ice/acetone) and the flask was vented to a trap containing a sat. aq. potassium iodide solution. Oxygen was bubbled through the solution for two min and then ozone was bubbled through the reaction mixture until the pink color dissipated (about 10 min). The ozone addition was stopped and the system was purged with oxygen for about 5 min. The system was placed under N$_2$ and NaBH$_4$ (231 mg, 6.11 mmol) was added along with additional MeOH (10 mL). The reaction mixture was stirred at room temperature for 16 h, quenched with sat. aq. NH$_4$Cl (10 mL), and extracted with DCM (3×10 mL). The combined organic extracts were passed through a phase separator cartridge to remove residual H$_2$O and then treated with Celite® (2 scoopula tip-fulls). The solvent was removed under reduced pressure and the resulting adsorbed material was directly loaded onto a column and purified using flash column chromatography (40 g SiO$_2$, 0→35% EtOAc/hexanes) to afford the title compound (578 mg, 1.64 mmol, 80%) as a colorless oil; $^1$H NMR (400 MHz, CDCl$_3$) δ 7.29-7.21 (m, 2H), 6.90-6.83 (m, 2H), 4.53 (d, J=11.2 Hz, 1H), 4.33 (d, J=11.2 Hz, 1H), 3.79 (s, 3H), 3.65-3.54 (m, 3H), 3.51-3.38 (m, 3H), 2.54-2.46 (m, 1H), 1.74-1.32 (m, 6H), 1.29-1.14 (m, 5H), 0.91 (t, J=7.4 Hz, 3H), 0.87 (app dd, J=6.6, 1.1 Hz, 6H); $^{13}$C NMR (101 MHz, CDCl$_3$) δ 159.06, 130.78, 129.22, 113.72, 81.26, 74.95, 72.16, 70.18, 62.89, 55.23, 45.05, 37.94, 28.55, 25.14, 23.45, 22.62, 22.59, 17.24, 10.76; ESIMS m/z 375 ([M+Na]$^1$).

Example 3, Step 2. Preparation of (S)-methyl 2-((tert-butoxycarbonyl)amino)-3-(((2R,3S)-3-((S)-1-((4-methoxybenzyl)oxy)ethyl)-6-methyl-2-propoxyheptyl)oxy)propanoate Example 3, Step 3. Preparation of (S)-methyl 2-((tert-butoxycarbonyl)amino)-3-(((2R,3S)-3-((S)-1-hydroxyethyl)-6-methyl-2-propoxyheptyl)oxy)propanoate

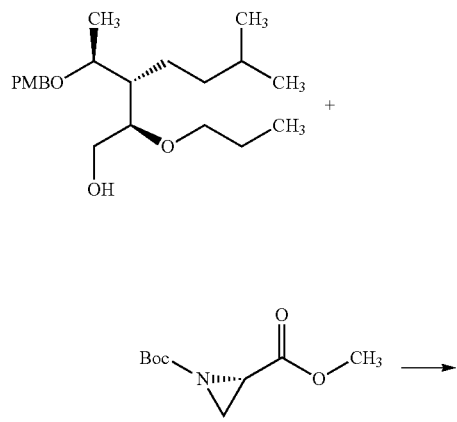

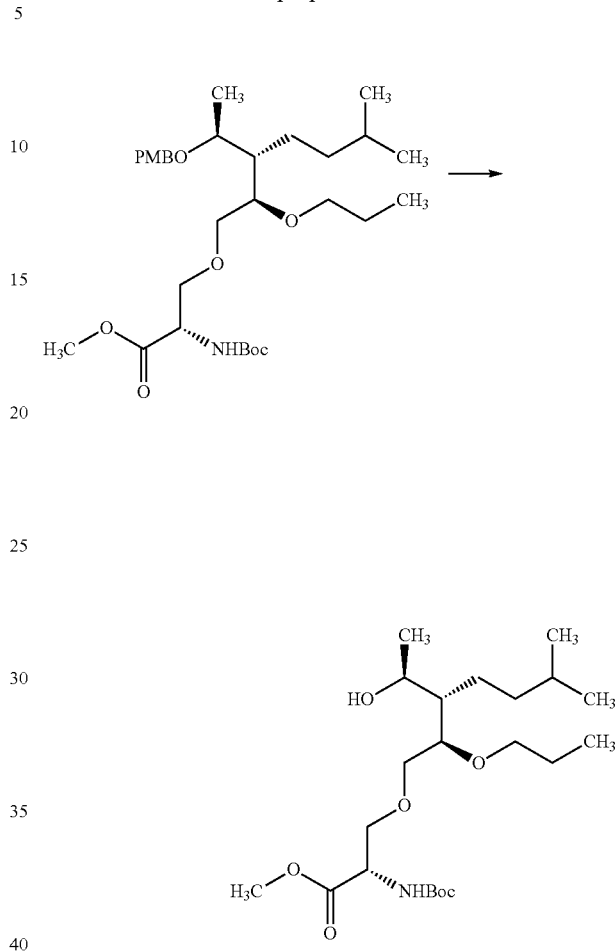

To a 0° C. solution of (S)-1-tert-butyl 2-methyl aziridine-1,2-dicarboxylate (325 mg, 1.62 mmol) and (2R,3S)-3-((S)-1-((4-methoxybenzyl)oxy)ethyl)-6-methyl-2-propoxyheptan-1-ol (475 mg, 1.35 mmol) in DCM (6.74 mL) was added BF$_3$—OEt$_2$ (34.2 microliters (4), 0.269 mmol). After 45 min at this temperature, sat. aq. NaHCO$_3$ (10 mL) was added and the phases were separated. The aq. phase was further extracted with DCM (3×10 mL) and the combined organic extracts were washed with brine (8 mL), dried over Na$_2$SO$_4$, filtered, and the filtrate was treated with Celite® (3 scoopula tip-fulls). The solvent was removed under reduced pressure and the resulting adsorbed material was directly loaded onto a column and purified using flash column chromatography (80 g SiO$_2$, 02→0% acetone/hexanes) to afford the title compound (325 mg, 0.516 mmol, 38%) as a colorless oil: $^1$H NMR (400 MHz, CDCl$_3$) δ 7.29-7.21 (m, 2H), 6.90-6.84 (m, 2H), 5.43 (d, J=8.8 Hz, 1H), 4.49 (d, J=11.3 Hz, 1H), 4.43-4.29 (m, 2H), 3.92-3.84 (m, 1H), 3.79 (s, 3H), 3.72 (s, 3H), 3.66-3.42 (m, 6H), 3.31 (app dt, J=9.0, 6.7 Hz, 1H), 1.60-1.46 (m, 3H), 1.46-1.16 (m, 17H), 0.93-0.84 (m, 9H); $^{13}$C NMR (101 MHz, CDCl$_3$) δ 171.15, 159.03, 155.54, 131.21, 129.13, 113.72, 79.83, 78.74, 75.23, 73.76, 72.69, 71.33, 70.07, 55.25, 54.12, 52.31, 45.63, 38.45, 28.62, 28.32, 24.03, 23.51, 22.61, 22.56, 17.15, 10.75; ESIMS m/z 576 ([M+Na]$^+$).

To a solution of (S)-methyl 2-((tert-butoxycarbonyl)amino)-3-(((2R,3S)-3-((S)-1-((4-methoxybenzyl)oxy)ethyl)-6-methyl-2-propoxyheptyl)oxy)propanoate (375 mg, 0.677 mmol) in H$_2$O (0.205 mL) and DCM (2.05 mL) at 0° C. was added DDQ (161 mg, 0.711 mmol). The mixture was vigorously stirred at this temperature for 1 h and then treated with 1N NaOH (677 µL, 0.677 mmol) and H$_2$O (8 mL). The phases were separated and the aq. phase was further extracted with DCM (3×15 mL). The combined organic extracts were washed with brine (8 mL), dried over Na$_2$SO$_4$, filtered, and the filtrate was treated with Celite® (2 scoopula tip-fulls). The solvent was removed under reduced pressure and the resulting adsorbed material was directly loaded onto a column and purified using flash column chromatography (40 g SiO$_2$, 0→60% EtOAc/hexanes) to afford the title compound (244 mg, 0.563 mmol, 83%) as a colorless oil; $^1$H NMR (400 MHz, CDCl$_3$) δ 5.45 (d, J=8.8 Hz, 1H), 4.53-4.33 (m, 1H), 3.95-3.87 (m, 1H), 3.82-3.71 (m, 6H), 3.70-3.44 (m, 5H), 1.63-1.35 (m, 14H), 1.31-1.09 (m, 6H), 1.00-0.80 (m, 9H); $^{13}$C NMR (101 MHz, CDCl$_3$) δ 171.02, 155.42, 80.23, 79.89, 72.20, 72.12, 71.49, 68.97, 54.01, 52.34, 46.18, 37.44, 28.27, 24.79, 23.27, 22.54, 22.49, 22.16, 10.57; ESIMS m/z 456 ([M+Na]$^+$).

Example 3, Step 4. Preparation of (S)-2-((tert-butoxycarbonyl)amino)-3-(((2R,3S)-3-((S)-1-hydroxyethyl)-6-methyl-2-propoxyheptyl)oxy)propanoic acid

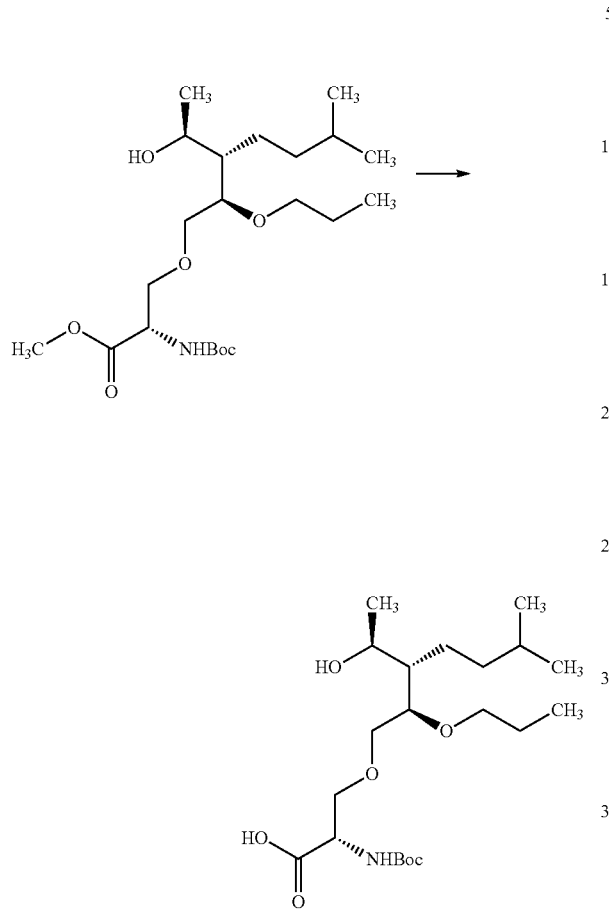

To a solution of (S)-methyl 2-((tert-butoxycarbonyl)amino)-3-(((2R,3S)-3-((S)-1-hydroxyethyl)-6-methyl-2-propoxyheptyl)oxy)propanoate (240 mg, 0.554 mmol) in THF (3.69 mL) and H$_2$O (1.85 mL) was added LiOH.H$_2$O (67.7 mg, 1.61 mmol), and the reaction was stirred at room temperature for 4 h and then diluted with EtOAc (10 mL) and 0.2N HCl (10 mL). The phases were separated and the aq. phase was further extracted with EtOAc (3×15 mL). The combined organic extracts were washed with brine (5 mL), dried over Na$_2$SO$_4$, filtered, and concentrated to dryness to afford the title compound (220 mg, 0.524 mmol, 95%) as a colorless oil: $^1$H NMR (400 MHz, CDCl$_3$) δ 7.87-7.62 (m, 2H), 5.54 (d, J=8.2 Hz, 1H), 4.43-4.35 (m, 1H), 3.97-3.89 (m, 1H), 3.89-3.77 (m, 1H), 3.75-3.42 (m, 6H), 1.64-1.32 (m, 14H), 1.28-1.09 (m, 6H), 0.96-0.84 (m, 9H); $^{13}$C NMR (101 MHz, CDCl$_3$) δ 174.07, 155.58, 80.32, 79.83, 72.19, 71.68, 71.61, 69.32, 54.10, 46.34, 37.40, 28.32, 28.27, 24.98, 23.17, 22.55, 22.47, 21.99, 10.56; ESIMS m/z 418 ([M−H]$^-$).

Example 4, Preparation of tert-butyl ((3S,7R,8S,9S)-8-isopentyl-9-methyl-2-oxo-7-propoxy-1,5-dioxonan-3-yl)carbamate (39)

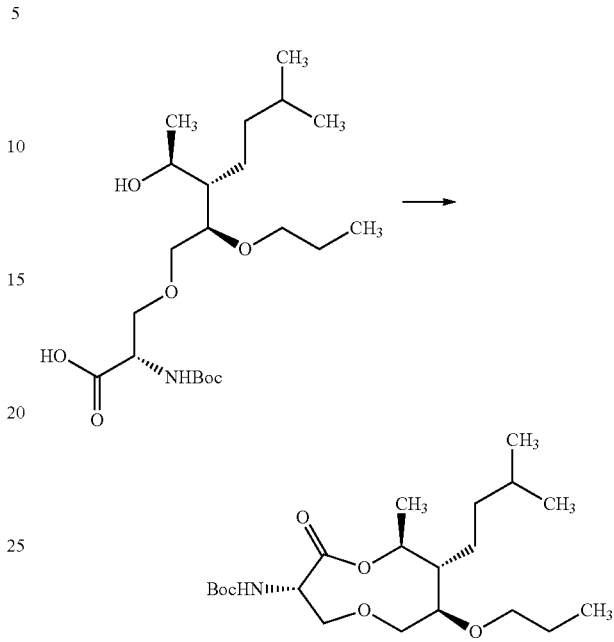

A solution of (S)-2-((tert-butoxycarbonyl)amino)-3-(((2R,3S)-3-((S)-1-hydroxyethyl)-6-methyl-2-propoxyheptyl)oxy)propanoic acid (220 mg, 0.524 mmol) in anhydrous DCM (30 mL) was added over 8 h, using a syringe pump, to a stirred solution of MNBA (361 mg, 1.05 mmol) and DMAP (384 mg, 3.15 mmol) in DCM (52 mL) at room temperature. The mixture was stirred for 10 h and then treated with Celite® (4 scoopula tip-fulls). The solvent was removed under reduced pressure and the resulting adsorbed material was directly loaded onto a column and purified using flash column chromatography (40 g SiO$_2$, 0→50% EtOAc/hexanes) to afford the title compound (178 mg, 0.443 mmol, 85%) as a white solid: mp 74-77° C.; $^1$H NMR (400 MHz, CDCl$_3$) δ 5.35 (d, J=8.4 Hz, 1H), 5.11-4.99 (m, 1H), 4.66-4.57 (m, 1H), 3.98-3.86 (m, 2H), 3.83-3.74 (m, 1H), 3.61-3.50 (m, 2H), 3.26-3.16 (m, 1H), 3.06-2.97 (m, 1H), 1.87-1.74 (m, 1H), 1.75-1.61 (m, 1H), 1.62-1.39 (m, 12H), 1.41-1.27 (m, 4H), 1.23-1.07 (m, 2H), 0.95-0.85 (m, 9H); $^{13}$C NMR (101 MHz, CDCl$_3$) δ 171.14, 155.20, 81.02, 79.95, 79.70, 75.26, 73.61, 71.33, 54.38, 50.13, 33.86, 28.73, 28.29, 25.98, 23.19, 22.55, 22.47, 19.86, 10.75; ESIMS m/z 424 ([M+Na]$^+$).

Example 5, Step 1. Preparation of tert-butyl ((3S,7R,8R,9S)-7-hydroxy-8-isopentyl-9-methyl-2-oxo-1,5-dioxonan-3-yl)carbamate (66)

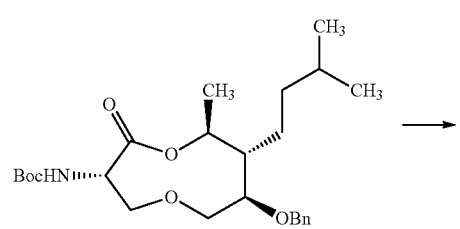

-continued

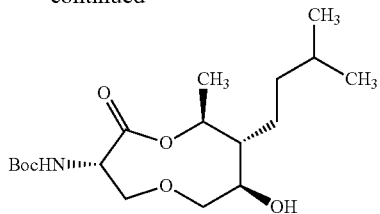

A solution of tert-butyl ((3S,7R,8S,9S)-7-(benzyloxy)-8-isopentyl-9-methyl-2-oxo-1,5-dioxonan-3-yl)carbamate (420 mg, 0.934 mmol) and 10% Pd/C (49.7 mg, 0.467 mmol) in THF (9.34 mL) was stirred under a hydrogen atmosphere (balloon) for 22 h. The balloon was refilled with hydrogen and stirred for an additional 16 h. The reaction mixture was filtered through a pad of Celite® and the pad was washed with EtOAc (2×15 mL). The combined filtrate and washes were concentrated to dryness to afford the title compound (315 mg, 0.806 mmol, 86%) as a white solid: mp 112-115° C.; $^1$H NMR (400 MHz, CDCl$_3$) δ 5.41 (d, J=8.2 Hz, 1H), 4.95 (dq, J=9.7, 6.3 Hz, 1H), 4.74-4.46 (m, 1H), 4.00 (dd, J=11.8, 6.8 Hz, 1H), 3.80-3.70 (m, 2H), 3.62-3.50 (m, 2H), 2.28-2.14 (m, 1H), 1.88-1.76 (m, 1H), 1.69-1.57 (m, 1H), 1.53-1.37 (m, 14H), 1.30-1.07 (m, 2H), 0.88 (app d, J=6.6 Hz, 6H); $^{13}$C NMR (101 MHz, CDCl$_3$) δ 171.70, 155.18, 80.10, 79.79, 73.84, 72.74, 53.48, 50.52, 33.91, 28.60, 28.28, 26.28, 22.55, 22.45, 20.01; ESIMS m/z 382 ([M+Na]$^+$).

Example 5, Step 2. Preparation of (3S,7R,8S,9S)-3-((tert-butoxycarbonyl)amino)-8-isopentyl-9-methyl-2-oxo-1,5-dioxonan-7-yl cyclopropanecarboxylate (49)

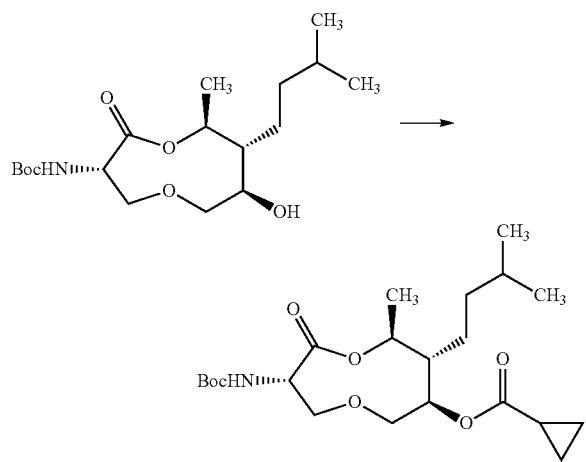

To a solution of tert-butyl ((3S,7R,8R,9S)-7-hydroxy-8-isopentyl-9-methyl-2-oxo-1,5-dioxonan-3-yl)carbamate (300 mg, 0.835 mmol) and DMAP (102 mg, 0.835 mmol) in anhydrous pyridine (2.50 mL) was added cyclopropanecarbonyl chloride (87 µL, 0.960 mmol) at 0° C., and the reaction was stirred at this temperature for 10 min and then removed from the cold bath. The reaction was stirred at room temperature for 3 h, treated with additional cyclopropanecarbonyl chloride (37.9 µL, 0.417 mmol), and stirred for an additional 1 h. The reaction was diluted with Et$_2$O (10 mL), followed by sat. aq. NH$_4$Cl (10 mL), and the phases were separated. The aq. phase was further extracted with Et$_2$O (2×10 mL), and the combined organic extracts were washed with brine (5 mL), dried over Na$_2$SO$_4$, filtered, and concentrated to dryness. The crude residue was loaded onto a silica gel and purified using flash column chromatography (40 g SiO$_2$, 0→50% EtOAc/hexanes) to afford the title compound (296 mg, 0.692 mmol, 83%) as a white solid: mp 92-95° C.; $^1$H NMR (400 MHz, CDCl$_3$) δ 5.31 (d, J=8.2 Hz, 1H), 5.09-4.97 (m, 1H), 4.75-4.60 (m, 2H), 3.99-3.89 (m, 1H), 3.78-3.63 (m, 3H), 2.13-2.01 (m, 1H), 1.65-1.54 (m, 1H), 1.53-1.26 (m, 15H), 1.19-1.04 (m, 2H), 1.05-0.93 (m, 2H), 0.90-0.82 (m, 8H); $^{13}$C NMR (101 MHz, CDCl$_3$) δ 173.70, 171.24, 155.15, 80.04, 78.29, 74.62, 74.25, 73.26, 53.76, 48.20, 33.52, 28.51, 28.28, 25.88, 22.47, 22.27, 19.80, 12.82, 8.53, 8.43; ESIMS m/z 450 ([M+Na]$^+$).

Example 6, Steps 1a and 2. Preparation of 3-hydroxy-N-((3S,7R,8S,9S)-8-isopentyl-9-methyl-2-oxo-7-propoxy-1,5-dioxonan-3-yl)-4-methoxypicolinamide (53)

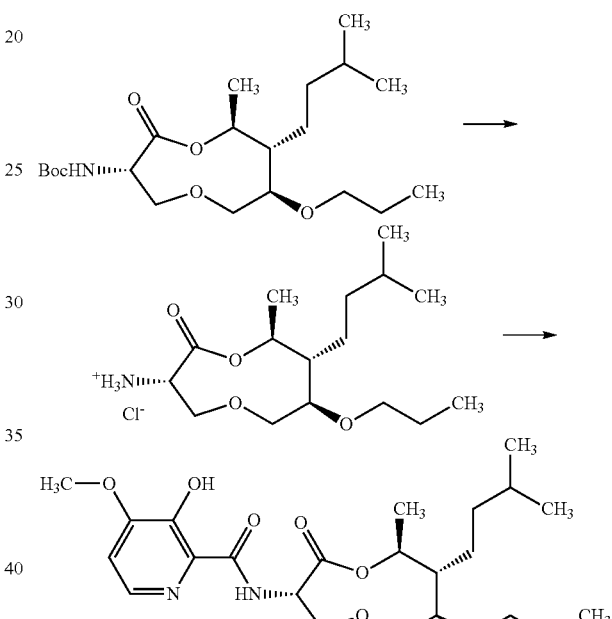

Step 1a

To a solution of tert-butyl ((3S,7R,8S,9S)-8-isopentyl-9-methyl-2-oxo-7-propoxy-1,5-dioxonan-3-yl)carbamate (170 mg, 0.423 mmol) in DCM (3 mL) was added 4M HCl in dioxane (1058 µL, 4.23 mmol) and the resulting solution was stirred at room temperature for 3 h. The solvent was evaporated under a stream of N$_2$ to give a white solid. This solid was triturated with Et$_2$O (3×3 mL) and the resulting powder was dried under high vacuum for 1 h. (3S,7R,8S,9S)-8-isopentyl-9-methyl-2-oxo-7-propoxy-1,5-dioxonan-3-aminium chloride: ESIMS m/z 302 ([M+H]$^+$).

Step 2

To a solution of (3S,7R,8S,9S)-8-isopentyl-9-methyl-2-oxo-7-propoxy-1,5-dioxonan-3-aminium chloride in DCM (3 mL) were added PyBop (242 mg, 0.466 mmol) and 3-hydroxy-4-methoxypicolinic acid (79 mg, 0.466 mmol), followed by the dropwise addition of N-Ethyl-N-isopropylpropan-2-amine (243 µL, 1.40 mmol). After 10 min, everything had solubilized and the solution was stirred for 5 h. The resulting pink solution was treated with Celite® (2 scoopula tip-fulls) and the solvent was removed under reduced pressure. The resulting adsorbed material was directly loaded onto a column and purified using flash column chromatography (40 g SiO$_2$, 0→100% EtOAc/hexanes) to provide the title compound (136 mg, 0.301 mmol, 71%) as a sticky, white solid: mp 54-57° C.; IR (thin film): 3368, 2955, 2873, 1746, 1648, 1528, 1263, 1087 cm$^{-1}$; $^1$H NMR (400 MHz, CDCl$_3$) δ 11.99 (s, 1H), 8.73 (d, J=8.1 Hz, 1H), 7.99 (d, J=5.2 Hz, 1H), 6.87 (d, J=5.3 Hz, 1H), 5.19-5.07 (m, 1H), 5.07-4.97 (m, 1H), 4.09-3.91 (m, 6H), 3.68-3.52 (m, 2H), 3.29-3.19 (m, 1H), 3.08 (dd, J=9.8, 6.0 Hz, 1H), 1.91-1.80 (m, 1H), 1.77-1.64 (m, 1H), 1.63-1.30 (m, 7H), 1.28-1.10 (m, 2H), 0.97-0.86 (m, 9H); HRMS-ESI m/z [M+H]$^+$ calcd for: C$_{23}$H$_{37}$N$_2$O$_7$, 453.2595. found, 453.2608.

Example 6, Steps 1b and 2. Preparation of N-((3S,7R,8S,9S)-8-benzyl-7-((benzyloxy)methoxy)-9-methyl-2-oxo-1,5-dioxonan-3-yl)-3-hydroxy-4-methoxypicolinamide (72)

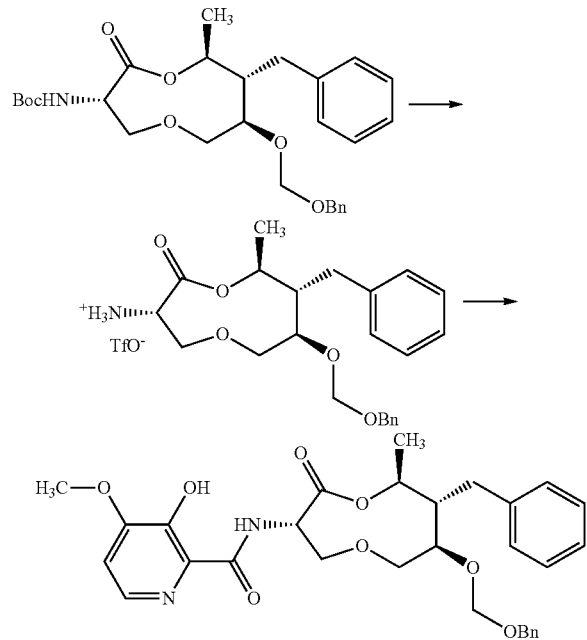

Step 1b

To a solution of tert-butyl ((3S,7R,8S,9S)-8-benzyl-7-((benzyloxy)methoxy)-9-methyl-2-oxo-1,5-dioxonan-3-yl)carbamate (46.3 mg, 0.093 mmol) in DCM (0.93 mL) was added 2,6-dimethylpyridine (32.4 µl, 0.278 mmol), followed by the dropwise addition of trimethylsilyl trifluoromethanesulfonate (33.5 µl, 0.185 mmol) at room temperature. The reaction was stirred at room temperature for 1.5 h, treated with MeOH (0.3 mL), and stirred overnight at room temperature. The solvent was then removed under a stream of N$_2$ to give (3S,7R,8S,9S)-8-benzyl-7-((benzyloxy)methoxy)-9-methyl-2-oxo-1,5-dioxonan-3-aminium trifluoromethanesulfonate: ESIMS m/z 400 ([M+H]$^+$).

Step 2

To a solution of (3S,7R,8S,9S)-8-benzyl-7-((benzyloxy)methoxy)-9-methyl-2-oxo-1,5-dioxonan-3-aminium trifluoromethanesulfonate in DCM (0.93 mL) was added 3-hydroxy-4-methoxypicolinic acid (17.24 mg, 0.102 mmol) followed by N-Ethyl-N-isopropylpropan-2-amine (53.3 µl, 0.306 mmol) and PyBop (53.1 mg, 0.102 mmol), and the reaction was stirred at room temperature overnight. The solvent was removed under a stream of N$_2$ and the resulting oil was purified by flash column chromatography (SiO$_2$, 1→40% acetone/hexanes) to afford the title compound (35.7 mg, 0.065 mmol, 70%) as a white foam: IR (thin film) 3369, 3028, 2938, 1744, 1649, 1577, 1528, 1453 cm$^{-1}$; $^1$H NMR (400 MHz, CDCl$_3$) δ 11.98 (d, J=0.7 Hz, 1H), 8.71 (d, J=8.1 Hz, 1H), 8.00 (d, J=5.2 Hz, 1H), 7.38-7.21 (m, 9H), 7.23-7.17 (m, 1H), 6.86 (d, J=5.2 Hz, 1H), 5.17 (dq, J=8.3, 6.4 Hz, 1H), 5.04 (ddd, J=8.1, 6.4, 4.6 Hz, 1H), 4.85 (d, J=7.0 Hz, 1H), 4.73 (d, J=7.0 Hz, 1H), 4.65 (d, J=11.9 Hz, 1H), 4.60 (d, J=11.8 Hz, 1H), 4.19 (dd, J=11.7, 6.4 Hz, 1H), 3.98-3.94 (m, 1H), 3.93 (s, 3H), 3.87 (dd, J=11.8, 5.5 Hz, 1H), 3.83 (dd, J=11.7, 4.7 Hz, 1H), 3.62 (ddd, J=8.8, 5.4, 2.0 Hz, 1H), 3.00 (dd, J=14.7, 4.5 Hz, 1H), 2.69 (dd, J=14.7, 7.2 Hz, 1H), 2.36 (tdd, J=8.5, 7.2, 4.5 Hz, 1H), 1.31 (d, J=6.4 Hz, 3H); HRMS-ESI m/z [M+H]$^+$ calcd for: C$_{30}$H$_{35}$N$_2$O$_8$, 551.2388. found, 551.2388.

Example 7, Preparation of ((2-(((3S,7R,8S,9S)-8-isopentyl-9-methyl-2-oxo-7-propoxy-1,5-dioxonan-3-yl)carbamoyl)-4-methoxypyridin-3-yl)oxy)methyl acetate (18)

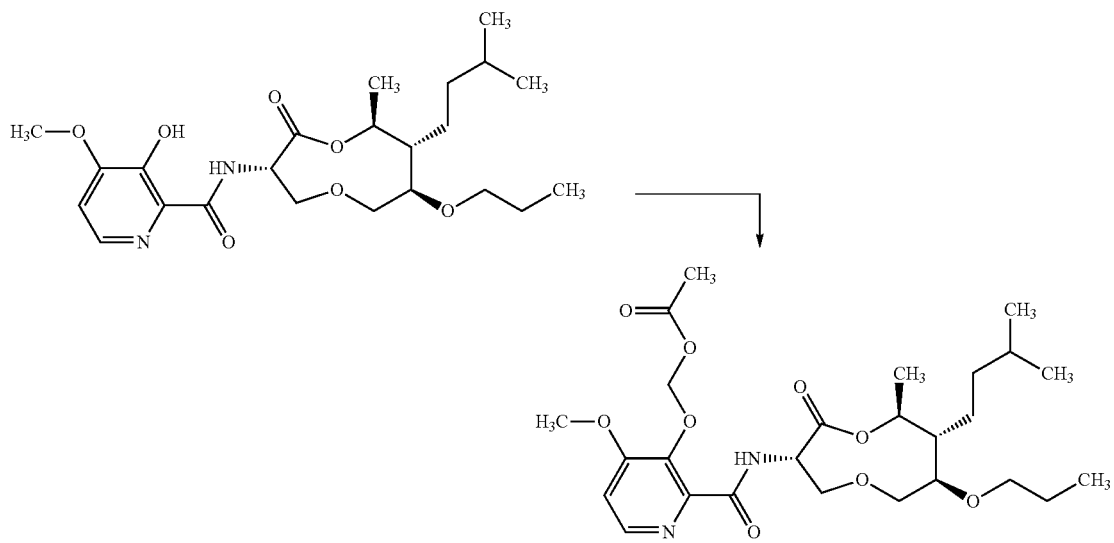

To a solution of 3-hydroxy-N-((3S,7R,8S,9S)-8-isopentyl-9-methyl-2-oxo-7-propoxy-1,5-dioxonan-3-yl)-4-methoxypicolinamide (105 mg, 0.232 mmol) and K$_2$CO$_3$ (64.1 mg, 0.464 mmol) in acetone (2.32 mL) was added bromomethyl acetate (49.7 mg, 0.325 mmol), and the reaction was heated to 50° C. and stirred at this temperature for 4 h. The mixture was cooled to room temperature, diluted with DCM (4 mL), and treated with Celite® (3 scoopula tip-fulls). The solvent was removed under reduced pressure and the resulting adsorbed material was directly loaded onto a column and purified using flash column chromatography (24 g SiO$_2$, 0→100% EtOAc/hexanes) to afford the title compound (79 mg, 0.151 mmol, 65%) as a slightly-yellow, viscous oil: IR (thin film): 3380, 2955, 2873, 1749, 1676, 1503, 1200, 1086 cm$^{-1}$; $^1$H NMR (400 MHz, CDCl$_3$) δ 8.60 (d, J=7.8 Hz, 1H), 8.29 (d, J=5.4 Hz, 1H), 6.96 (d, J=5.4 Hz, 1H), 5.78-5.69 (m, 2H), 5.16-5.00 (m, 2H), 4.08-3.86 (m, 6H), 3.68-3.52 (m, 2H), 3.31-3.15 (m, 1H), 3.07 (dd, J=9.9, 6.2 Hz, 1H), 2.07 (s, 3H), 1.92-1.80 (m, 1H), 1.78-1.65 (m, 1H), 1.62-1.31 (m, 7H), 1.25-1.07 (m, 2H), 0.96-0.85 (m, 9H); HRMS-ESI m/z [M+H]$^+$ calcd for: C$_{26}$H$_{41}$N$_2$O$_9$, 525.2807. found, 525.2805.

Example 8, Preparation of (3S,7R,8S,9S)-3-(3-acetoxy-4-methoxypicolinamido)-8-isopentyl-9-methyl-2-oxo-1,5-dioxonan-7-yl cyclopropanecarboxylate (68)

To a solution of (3S,7R,8S,9S)-3-(3-hydroxy-4-methoxypicolinamido)-8-isopentyl-9-methyl-2-oxo-1,5-dioxonan-7-yl cyclopropanecarboxylate (96 mg, 0.201 mmol) and acetyl chloride (21.4 μL, 0.301 mmol) in DCM (2.01 mL) was added TEA (41.9 μL, 0.301 mmol), and the reaction was stirred for 5 h. The mixture was treated with Celite® (3 scoopula tip-fulls) and the solvent was removed under reduced pressure. The adsorbed material was directly loaded onto a column and purified using flash column chromatography (24 g SiO$_2$, 0→100% EtOAc/hexanes) to afford the title compound (86 mg, 0.165 mmol, 82%) as a white powder: mp: 70-75° C.; IR (thin film): 3376, 2954, 1771, 1725, 1678, 1507, 1196, 1172 cm$^{-1}$; $^1$H NMR (400 MHz, CDCl$_3$) δ 8.72 (d, J=8.4 Hz, 1H), 8.34 (d, J=5.3 Hz, 1H), 7.01 (d, J=5.5 Hz, 1H), 5.13-5.00 (m, 2H), 4.75 (ddd, J=10.1, 5.2, 2.7 Hz, 1H), 4.04 (dd, J=11.8, 6.8 Hz, 1H), 3.90 (s, 3H), 3.81-3.72 (m, 3H), 2.38 (s, 3H), 2.16-2.04 (m, 1H), 1.66-1.28 (m, 7H), 1.18-1.06 (m, 2H), 1.04-0.95 (m, 2H), 0.91-0.82 (m, 8H); HRMS-ESI m/z [M+H]$^+$ calcd for: C$_{30}$H$_{35}$N$_2$O$_8$, 521.2494. found, 521.2495.

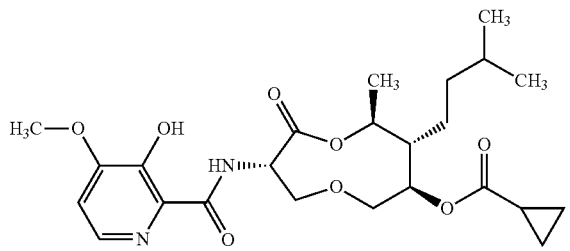

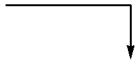

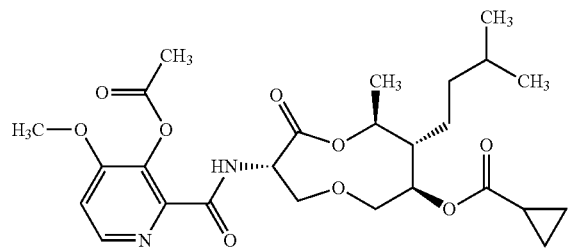

Example 9, Preparation of ((2-(((3S,7R,8S,9S)-8-(4-fluorobenzyl)-9-methyl-2-oxo-7-propoxy-1,5-dioxonan-3-yl)carbamoyl)-4-methoxypyridin-3-yl)oxy) methyl 2-ethoxyacetate

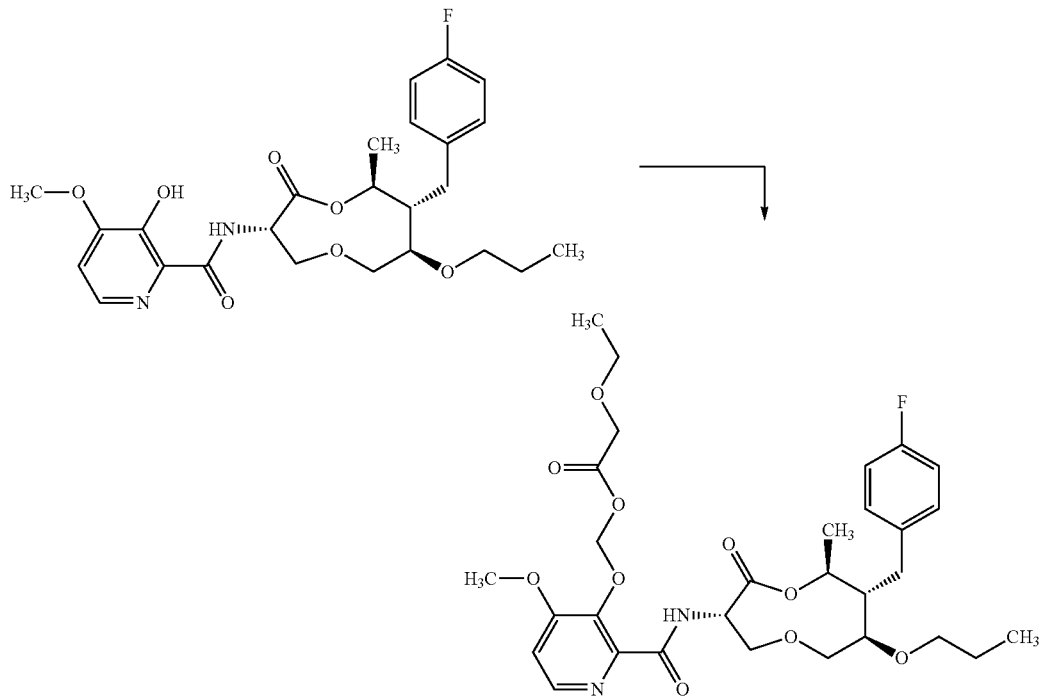

To a solution of N-((3S,7R,8S,9S)-8-(4-fluorobenzyl)-9-methyl-2-oxo-7-propoxy-1,5-dioxonan-3-yl)-3-hydroxy-4-methoxypicolinamide (64.5 mg, 0.131 mmol), Na$_2$CO$_3$ (27.9 mg, 0.263 mmol), and NaI (3.94 mg, 0.026 mmol) in acetone (1.3 mL) was added chloromethyl 2-ethoxyacetate (32.1 mg, 0.210 mmol), and the mixture was warmed to 55° C. and stirred at that temperature overnight. The solvent was evaporated under a stream of N$_2$ and the resulting oil was purified by flash column chromatography (SiO$_2$, 1→40% acetone/hexanes) to afford the title compound (64.6 mg, 0.106 mmol, 81%) as a white foam: $^1$H NMR (400 MHz, CDCl$_3$) δ 8.60 (d, J=7.8 Hz, 1H), 8.28 (d, J=5.4 Hz, 1H), 7.18 (dd, J=8.5, 5.6 Hz, 2H), 6.97 (t, J=8.7 Hz, 2H), 6.96 (d, J=5.5 Hz, 1H), 5.81 (s, 2H), 5.12 (dq, J=9.6, 6.3 Hz, 1H), 5.02 (ddd, J=7.8, 6.1, 3.8 Hz, 1H), 4.09 (s, 2H), 4.06 (dd, J=11.7, 5.8 Hz, 1H), 4.00 (d, J=10.0 Hz, 1H), 3.96-3.91 (m, 1H), 3.90 (s, 3H), 3.71 (dd, J=11.5, 5.8 Hz, 1H), 3.58 (q, J=7.0 Hz, 2H), 3.55-3.52 (m, 1H), 3.25 (dt, J=9.0, 6.6 Hz, 1H), 3.08 (dd, J=10.3, 5.1 Hz, 1H), 2.92 (dd, J=14.7, 4.1 Hz, 1H), 2.71 (dd, J=14.7, 6.0 Hz, 1H), 2.22-2.10 (m, 1H), 1.65-1.50 (m, 2H), 1.32 (d, J=6.3 Hz, 3H), 1.22 (t, J=7.0 Hz, 3H), 0.91 (t, J=7.4 Hz, 3H); $^{19}$F NMR (376 MHz, CDCl$_3$) δ −117.38; HRMS-ESI m/z [M+H)]$^+$ calcd for: C$_{30}$H$_{40}$FN$_2$O$_{10}$, 607.2662. found, 607.2673.

Example A: Evaluation of Fungicidal Activity: Leaf Blotch of Wheat (*Mycosphaerella graminicola*; Anamorph: *Septoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia Triticina*; Synonym: *Puccinia recondite* f Sp. *Tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf.

The plants were then transferred to a greenhouse set at 24° C. for disease to develop. Fungicide formulation, application and disease assessment followed the procedures as described in the Example A.

Example C: Evaluation of Fungicidal Activity: Wheat Glume Blotch (*Leptosphaeria Nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D: Evaluation of Fungicidal Activity: Apple Scab (*Venturia Inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% RH for 48 hr, and then moved to a greenhouse set at 20° C. for disease to develop. Fungicide formulation, application and disease assessment on the sprayed leaves followed the procedures as described in the Example A.

Example E: Evaluation of Fungicidal Activity: Grape Powdery Mildew (*Uncinula Necator*; Bayer Code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed. Fungicide formulation, application and disease assessment on the sprayed leaves followed the procedures as described in the Example A.

Example F: Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example G: Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example H: Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% RH then transferred to a growth room at 23° C. for disease to develop. Disease severity was assessed on the sprayed leaves.

Example I: Evaluation of Fungicidal Activity: Wheat Powdery Mildew (*Blumeria graminis* f. Sp. *Tritici*; Synonym: *Erysiphe graminis* f. Sp. *Tritici*; Bayer Code ERYSGT)

Wheat plants (variety Yuma) were grown from seed in a greenhouse in 50% mineral soil/50% soil-less Metro mix until the first leaf was fully emerged, with 7-10 seedlings per pot. These plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example J: Evaluation of Fungicidal Activity: Barley Powdery Mildew (*Blumeria graminis* f. Sp. *Hordei*; Synonym: *Erysiphe graminis* f. Sp. *Hordei*; Bayer Code ERYSGH)

Barley seedlings (variety Harrington) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example K: Evaluation of Fungicidal Activity: Barley Scald (*Rhyncosporium secalis*; Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example L: Evaluation of Fungicidal Activity: Rice Blast (*Magnaporthe grisea*; Anamorph: *Pyricularia oryzae*; Bayer Code PYRIOR)

Rice seedlings (variety *Japonica*) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example M: Evaluation of Fungicidal Activity: Tomato Early Blight (*Alternaria solani*; Bayer Code ALTESO)

Tomato plants (variety Outdoor girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example N: Evaluation of Fungicidal Activity: Cucumber Anthracnose (*Glomerella lagenarium*; Anamorph: *Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure and Appearance

| Compound Number | Structure | Prepared According To Example | Appearance |
|---|---|---|---|
| 1 | 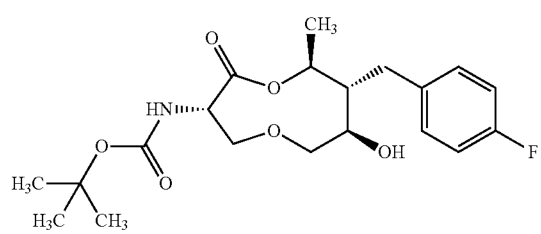 [SMILES: C[C@@H]1OC(=O)[C@@H](NC(=O)OC(C)(C)C)COC[C@H](O)[C@H]1Cc1ccc(F)cc1] | Example 5, Step 1. | Tacky Foam |
| 2 | 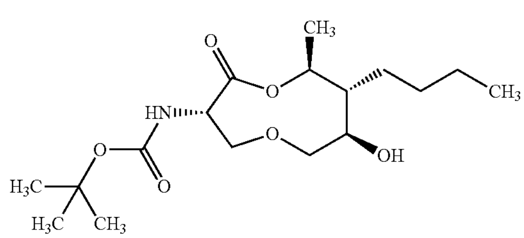 [SMILES: CCCC[C@H]1[C@H](C)OC(=O)[C@@H](NC(=O)OC(C)(C)C)COC[C@@H]1O] | Example 5, Step 1. | Colorless Oil |
| 3 | 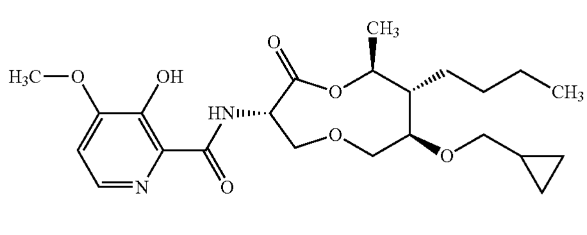 [SMILES: CCCC[C@H]1[C@H](C)OC(=O)[C@@H](NC(=O)c2nccc(OC)c2O)COC[C@@H]1OCC1CC1] | Example 6, Step 2. | White Solid |

TABLE 1-continued

Compound Structure and Appearance

| Compound Number | Structure | Prepared According To Example | Appearance |
|---|---|---|---|
| 4 | 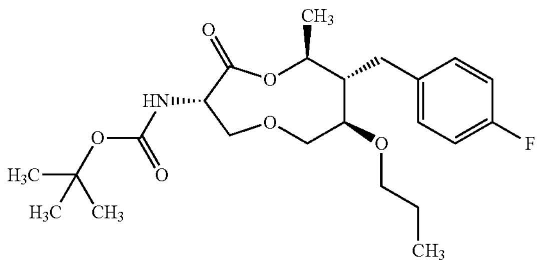 [SMILES: CCCO[C@H]1COC[C@H](NC(=O)OC(C)(C)C)C(=O)O[C@@H](C)[C@@H]1Cc1ccc(F)cc1] | Example 1, Steps 1, 3-5; Example 2, Step 2; Example 3, Steps 1-4; Example 4. | Pale Yellow Oil |
| 5 | 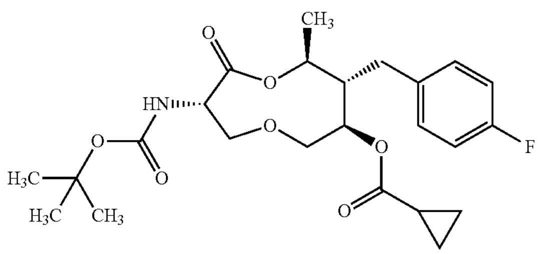 [SMILES: C[C@@H]1OC(=O)[C@@H](NC(=O)OC(C)(C)C)COC[C@H](OC(=O)C2CC2)[C@H]1Cc1ccc(F)cc1] | Example 5, Step 2. | Colorless Oil |
| 6 | 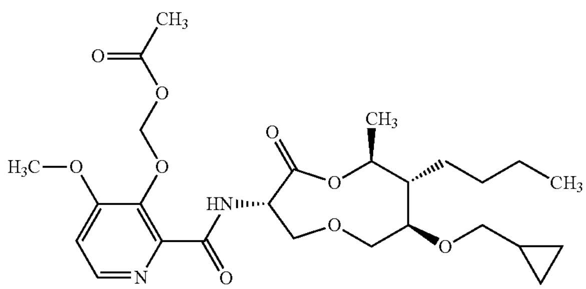 [SMILES: CCCC[C@H]1[C@H](C)OC(=O)[C@@H](NC(=O)c2nccc(OC)c2OCOC(C)=O)COC[C@@H]1OCC1CC1] | Example 7. | Colorless Oil |
| 7 | 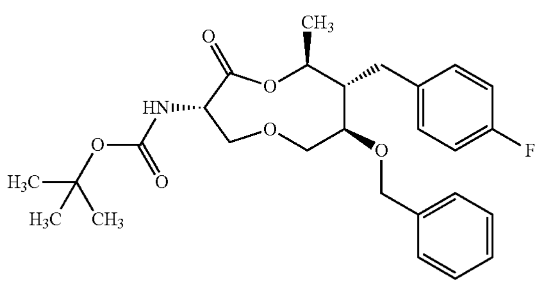 [SMILES: C[C@@H]1OC(=O)[C@@H](NC(=O)OC(C)(C)C)COC[C@H](OCc2ccccc2)[C@H]1Cc1ccc(F)cc1] | Example 1, Steps 1, 3-5; Example 2, Step 3; Example 3, Steps 1-4; Example 4. | White Foam |
| 8 | 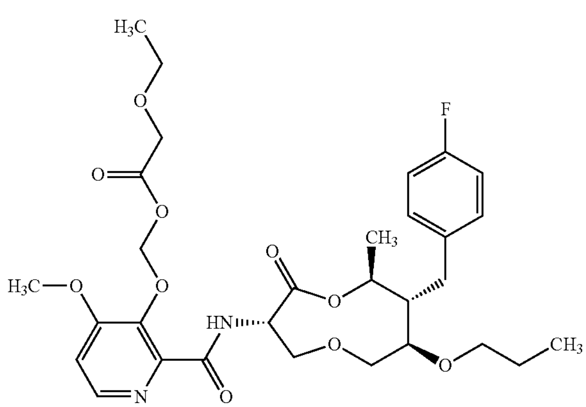 [SMILES: CCCO[C@H]1COC[C@H](NC(=O)c2nccc(OC)c2OCOC(=O)COCC)C(=O)O[C@@H](C)[C@@H]1Cc1ccc(F)cc1] | Example 9 | White Foam |

TABLE 1-continued

Compound Structure and Appearance

| Compound Number | Structure | Prepared According To Example | Appearance |
|---|---|---|---|
| 9 | 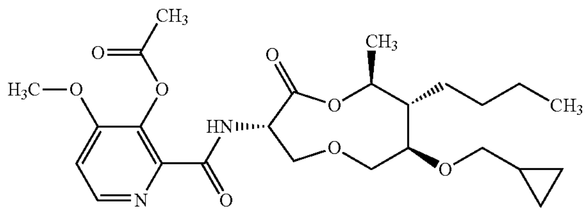 [SMILES: CCCC[C@H]1[C@H](C)OC(=O)[C@@H](NC(=O)c2nccc(OC)c2OC(C)=O)COC[C@@H]1OCC1CC1] | Example 8 | Yellow Foam |
| 10 | 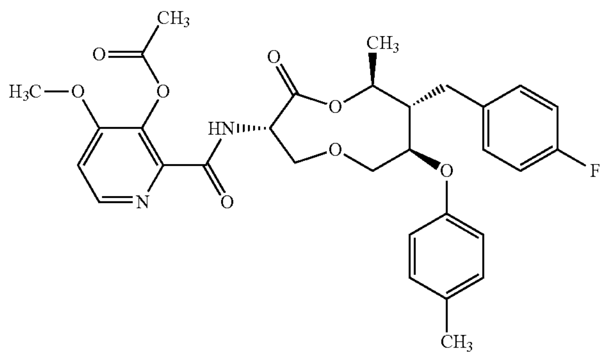 [SMILES: COc1ccnc(C(=O)N[C@H]2COC[C@H](Oc3ccc(C)cc3)[C@@H](Cc3ccc(F)cc3)[C@H](C)OC2=O)c1OC(C)=O] | Example 8. | White Foam |
| 11 | 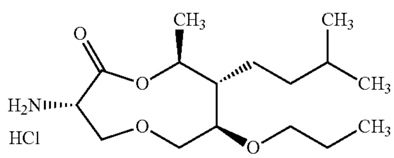 [SMILES: Cl ; CCCO[C@H]1COC[C@H](N)C(=O)O[C@@H](C)[C@@H]1CCC(C)C] | Example 6, Step 1a. | White Powder |
| 12 | 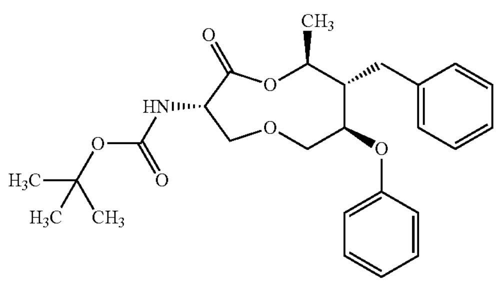 [SMILES: C[C@@H]1OC(=O)[C@@H](NC(=O)OC(C)(C)C)COC[C@H](Oc2ccccc2)[C@H]1Cc1ccccc1] | Example 1, Steps 1, 3, 6, 7, 8; Example 2, Step 1; Example 3, Steps 1-4; Example 4. | Clear Oil |
| 13 | 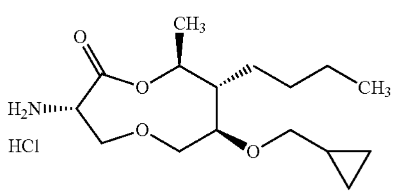 [SMILES: Cl ; CCCC[C@H]1[C@H](C)OC(=O)[C@@H](N)COC[C@@H]1OCC1CC1] | Example 6, Step 1a. | White Solid |
| 14 | 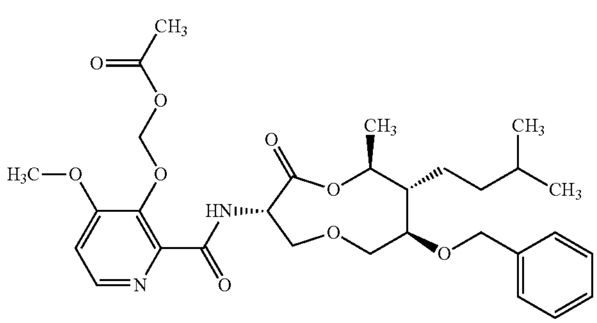 [SMILES: COc1ccnc(C(=O)N[C@H]2COC[C@H](OCc3ccccc3)[C@@H](CCC(C)C)[C@H](C)OC2=O)c1OCOC(C)=O] | Example 7. | Sticky Oil |

TABLE 1-continued

Compound Structure and Appearance

| Compound Number | Structure | Prepared According To Example | Appearance |
|---|---|---|---|
| 15 | 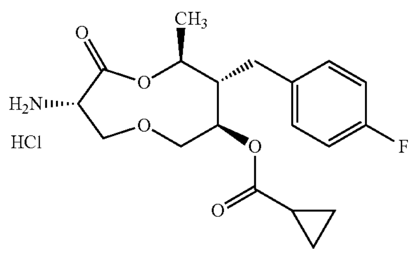 [SMILES: Cl ; C[C@@H]1OC(=O)[C@@H](N)COC[C@H](OC(=O)C2CC2)[C@H]1Cc1ccc(F)cc1] | Example 6, Step 1a. | White Solid |
| 16 | 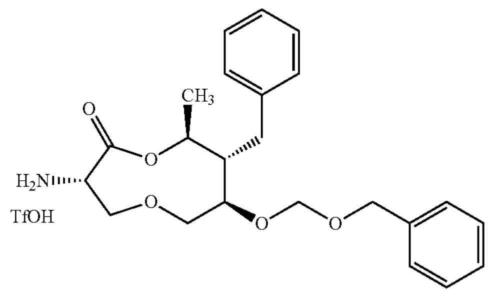 [SMILES: "TfOH" ; C[C@@H]1OC(=O)[C@@H](N)COC[C@H](OCOCc2ccccc2)[C@H]1Cc1ccccc1] | Example 6, Step 1b. | Colorless Oil |
| 17 | 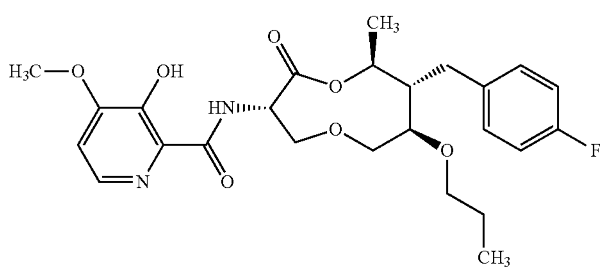 [SMILES: CCCO[C@H]1COC[C@H](NC(=O)c2nccc(OC)c2O)C(=O)O[C@@H](C)[C@@H]1Cc1ccc(F)cc1] | Example 6, Step 2. | White Solid |
| 18 | 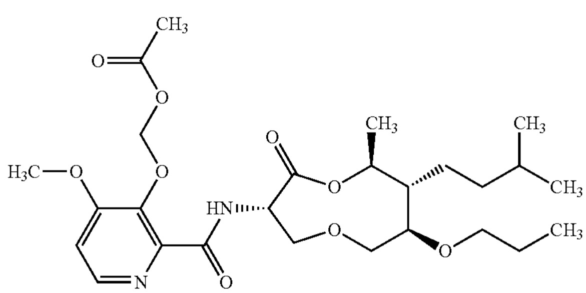 [SMILES: CCCO[C@H]1COC[C@H](NC(=O)c2nccc(OC)c2OCOC(C)=O)C(=O)O[C@@H](C)[C@@H]1CCC(C)C] | Example 7. | Viscous Oil |
| 19 | 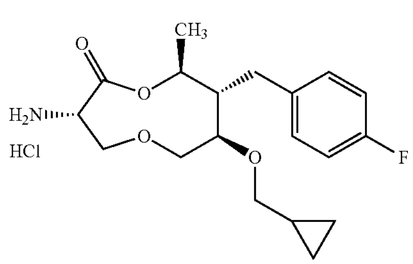 [SMILES: Cl ; C[C@@H]1OC(=O)[C@@H](N)COC[C@H](OCC2CC2)[C@H]1Cc1ccc(F)cc1] | Example 6, Step 1a. | White Solid |

TABLE 1-continued

Compound Structure and Appearance

| Compound Number | Structure | Prepared According To Example | Appearance |
|---|---|---|---|
| 20 | 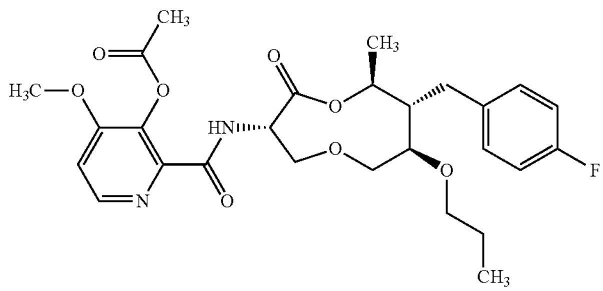 [SMILES: CCCO[C@H]1COC[C@H](NC(=O)c2nccc(OC)c2OC(C)=O)C(=O)O[C@@H](C)[C@@H]1Cc1ccc(F)cc1] | Example 8. | White Foam |
| 21 | 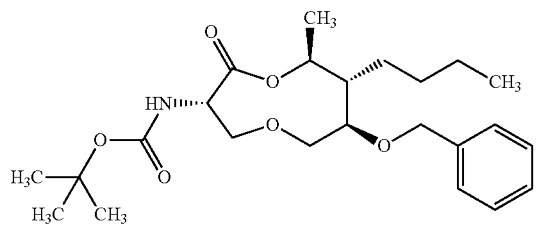 [SMILES: CCCC[C@H]1[C@H](C)OC(=O)[C@@H](NC(=O)OC(C)(C)C)COC[C@@H]1OCc1ccccc1] | Example 1, Steps 1-5; Example 2, Step 3; Example 3, Steps 1-4; Example 4. | Colorless Oil |
| 22 | 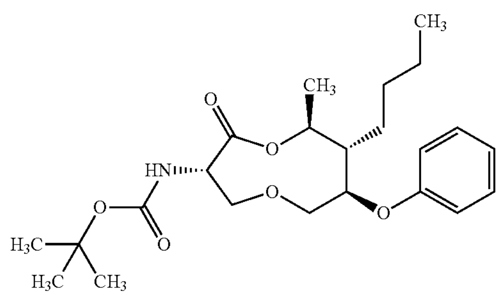 [SMILES: CCCC[C@H]1[C@H](C)OC(=O)[C@@H](NC(=O)OC(C)(C)C)COC[C@@H]1Oc1ccccc1] | Example 1, Steps 1-5; Example 2, Step 1; Example 3, Steps 1-4; Example 4. | Colorless Oil |
| 23 | 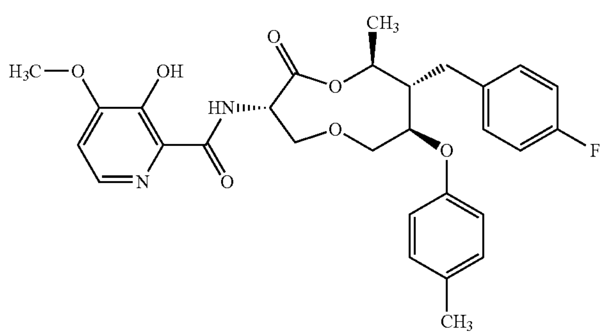 [SMILES: COc1ccnc(C(=O)N[C@H]2COC[C@H](Oc3ccc(C)cc3)[C@@H](Cc3ccc(F)cc3)[C@H](C)OC2=O)c1O] | Example 6, Step 2. | White Foam |
| 24 | 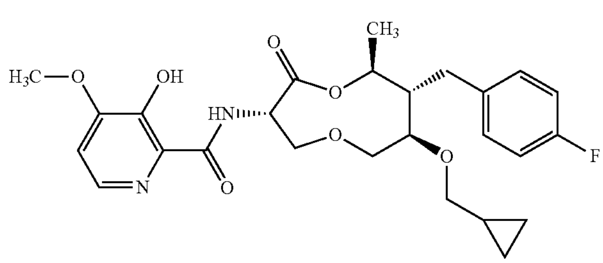 [SMILES: COc1ccnc(C(=O)N[C@H]2COC[C@H](OCC3CC3)[C@@H](Cc3ccc(F)cc3)[C@H](C)OC2=O)c1O] | Example 6, Step 2. | White Foam |

TABLE 1-continued

Compound Structure and Appearance

| Compound Number | Structure | Prepared According To Example | Appearance |
|---|---|---|---|
| 25 | 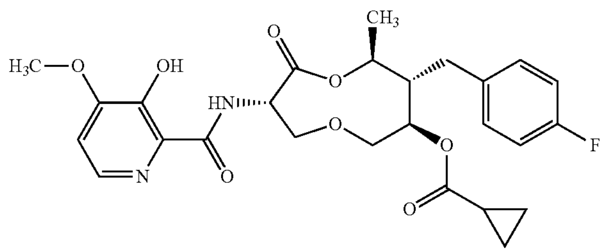 [SMILES: COc1ccnc(C(=O)N[C@H]2COC[C@H](OC(=O)C3CC3)[C@@H](Cc3ccc(F)cc3)[C@H](C)OC2=O)c1O] | Example 6, Step 2. | White Solid |
| 26 | 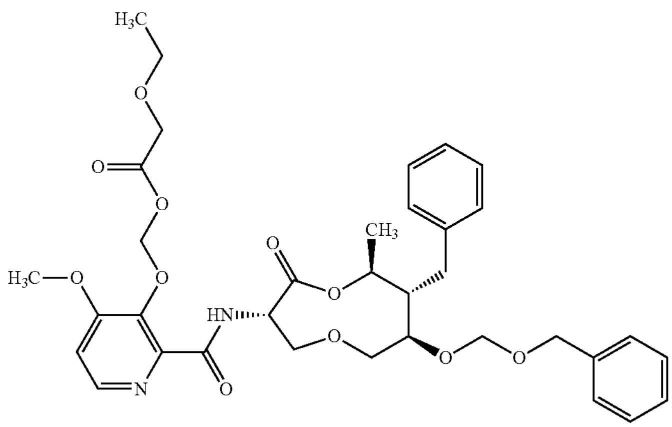 [SMILES: CCOCC(=O)OCOc1c(OC)ccnc1C(=O)N[C@H]1COC[C@H](OCOCc2ccccc2)[C@@H](Cc2ccccc2)[C@H](C)OC1=O] | Example 9. | Colorless Oil |
| 27 | 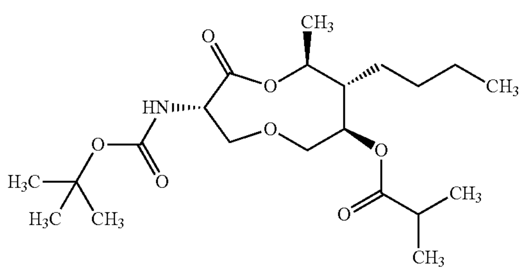 [SMILES: CCCC[C@H]1[C@H](C)OC(=O)[C@@H](NC(=O)OC(C)(C)C)COC[C@@H]1OC(=O)C(C)C] | Example 5, Step 2. | Colorless Oil |
| 28 | 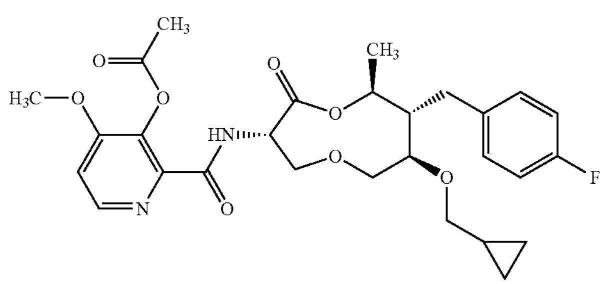 [SMILES: COc1ccnc(C(=O)N[C@H]2COC[C@H](OCC3CC3)[C@@H](Cc3ccc(F)cc3)[C@H](C)OC2=O)c1OC(C)=O] | Example 8. | White Foam |
| 29 | 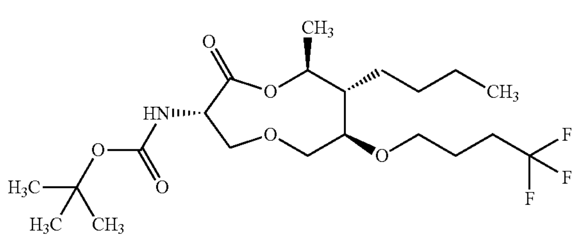 [SMILES: CCCC[C@H]1[C@H](C)OC(=O)[C@@H](NC(=O)OC(C)(C)C)COC[C@@H]1OCCCC(F)(F)F] | Example 1, Steps 1-5; Example 2, Step 2; Example 3, Steps 1-4; Example 4. | Colorless Oil |

TABLE 1-continued

Compound Structure and Appearance

| Compound Number | Structure | Prepared According To Example | Appearance |
|---|---|---|---|
| 30 | 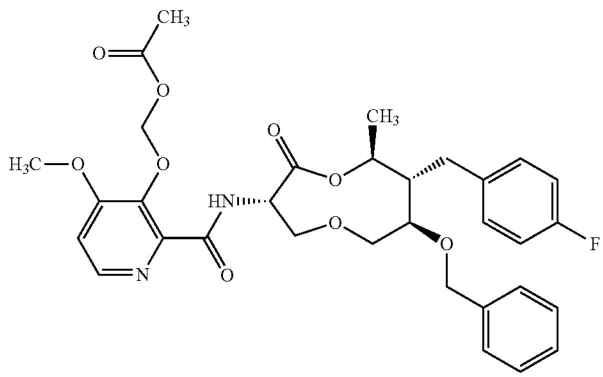 [SMILES: COc1ccnc(C(=O)N[C@H]2COC[C@H](OCc3ccccc3)[C@@H](Cc3ccc(F)cc3)[C@H](C)OC2=O)c1OCOC(C)=O] | Example 7. | White Foam |
| 31 | 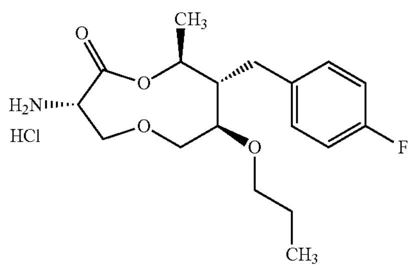 [SMILES: Cl ; CCCO[C@H]1COC[C@H](N)C(=O)O[C@@H](C)[C@@H]1Cc1ccc(F)cc1] | Example 6, Step 1a. | White Solid |
| 32 | 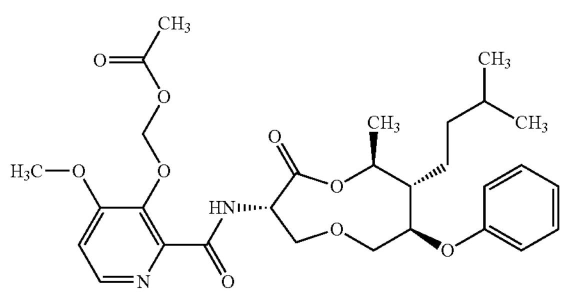 [SMILES: COc1ccnc(C(=O)N[C@H]2COC[C@H](Oc3ccccc3)[C@@H](CCC(C)C)[C@H](C)OC2=O)c1OCOC(C)=O] | Example 7. | Sticky White Solid |
| 33 | 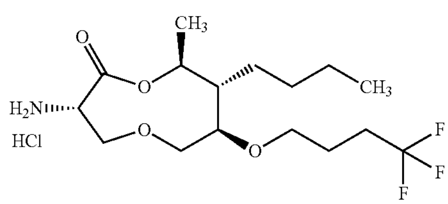 [SMILES: Cl ; CCCC[C@H]1[C@H](C)OC(=O)[C@@H](N)COC[C@@H]1OCCCC(F)(F)F] | Example 6, Step 1a. | White Solid |
| 34 | 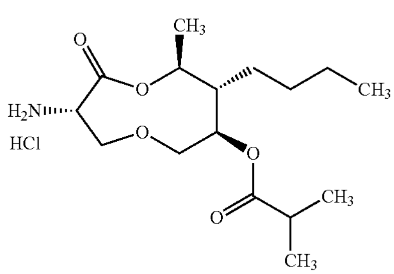 [SMILES: Cl ; CCCC[C@H]1[C@H](C)OC(=O)[C@@H](N)COC[C@@H]1OC(=O)C(C)C] | Example 6, Step 1a. | White Solid |

TABLE 1-continued

Compound Structure and Appearance

| Compound Number | Structure | Prepared According To Example | Appearance |
|---|---|---|---|
| 35 | 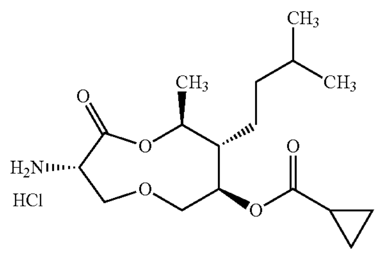 [SMILES: Cl ; CC(C)CC[C@H]1[C@H](C)OC(=O)[C@@H](N)COC[C@@H]1OC(=O)C1CC1] | Example 6, Step 1a. | White Powder |
| 36 | 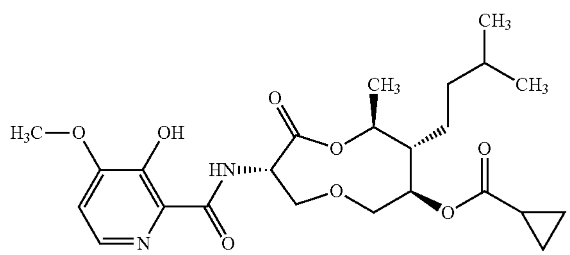 [SMILES: COc1ccnc(C(=O)N[C@H]2COC[C@H](OC(=O)C3CC3)[C@@H](CCC(C)C)[C@H](C)OC2=O)c1O] | Example 6, Step 2. | White Solid |
| 37 | 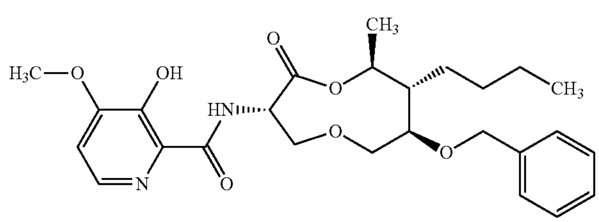 [SMILES: CCCC[C@H]1[C@H](C)OC(=O)[C@@H](NC(=O)c2nccc(OC)c2O)COC[C@@H]1OCc1ccccc1] | Example 6, Step 2. | White Solid |
| 38 | 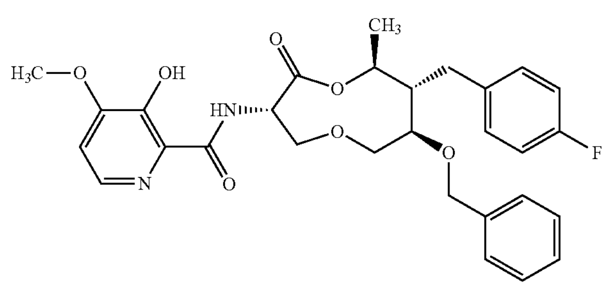 [SMILES: COc1ccnc(C(=O)N[C@H]2COC[C@H](OCc3ccccc3)[C@@H](Cc3ccc(F)cc3)[C@H](C)OC2=O)c1O] | Example 6, Step 2. | White Solid |
| 39 | 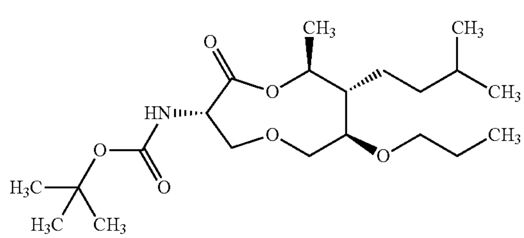 [SMILES: CCCO[C@H]1COC[C@H](NC(=O)OC(C)(C)C)C(=O)O[C@@H](C)[C@@H]1CCC(C)C] | Example 1, Steps 1-5; Example 2, Step 2; Example 3, Steps 1-4; Example 4. | White Solid |

TABLE 1-continued

Compound Structure and Appearance

| Compound Number | Structure | Prepared According To Example | Appearance |
| --- | --- | --- | --- |
| 40 | 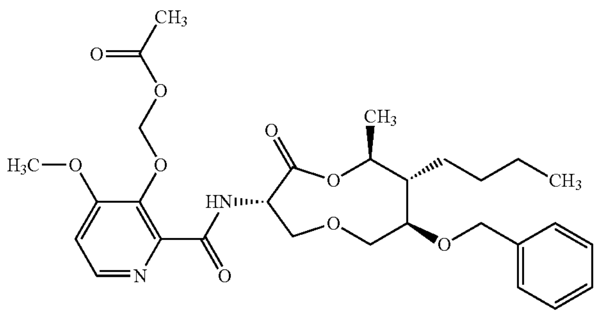 [SMILES: CCCC[C@H]1[C@H](C)OC(=O)[C@@H](NC(=O)c2nccc(OC)c2OCOC(C)=O)COC[C@@H]1OCc1ccccc1] | Example 7. | Colorless Oil |
| 41 | 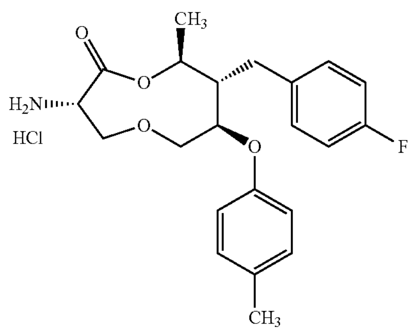 [SMILES: Cl ; Cc1ccc(O[C@H]2COC[C@H](N)C(=O)O[C@@H](C)[C@@H]2Cc2ccc(F)cc2)cc1] | Example 6, Step 1a. | White Solid |
| 42 | 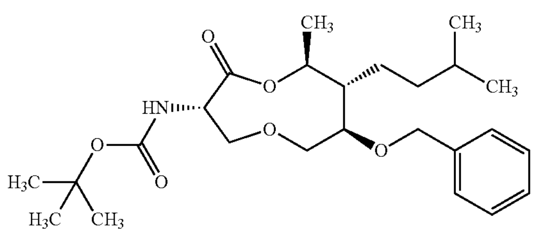 [SMILES: CC(C)CC[C@H]1[C@H](C)OC(=O)[C@@H](NC(=O)OC(C)(C)C)COC[C@@H]1OCc1ccccc1] | Example 1, Steps 1-5; Example 2, Step 3; Example 3, Steps 1-4; Example 4. | White Solid |
| 43 | 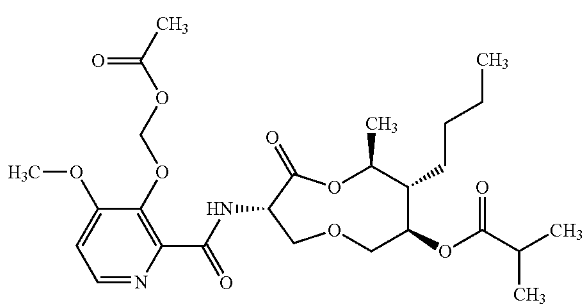 [SMILES: CCCC[C@H]1[C@H](C)OC(=O)[C@@H](NC(=O)c2nccc(OC)c2OCOC(C)=O)COC[C@@H]1OC(=O)C(C)C] | Example 7. | Colorless Oil |
| 44 | 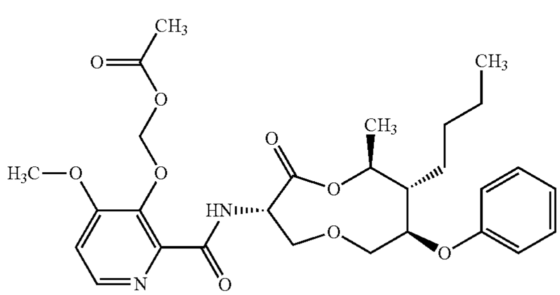 [SMILES: CCCC[C@H]1[C@H](C)OC(=O)[C@@H](NC(=O)c2nccc(OC)c2OCOC(C)=O)COC[C@@H]1Oc1ccccc1] | Example 7. | White Foam |

TABLE 1-continued

Compound Structure and Appearance

| Compound Number | Structure | Prepared According To Example | Appearance |
|---|---|---|---|
| 45 | 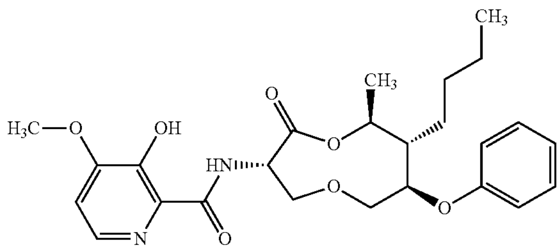 [SMILES: CCCC[C@H]1[C@H](C)OC(=O)[C@@H](NC(=O)c2nccc(OC)c2O)COC[C@@H]1Oc1ccccc1] | Example 6, Step 2. | White Foam |
| 46 | 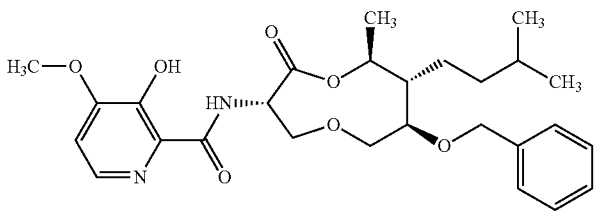 [SMILES: COc1ccnc(C(=O)N[C@H]2COC[C@H](OCc3ccccc3)[C@@H](CCC(C)C)[C@H](C)OC2=O)c1O] | Example 6, Step 2. | White Powder |
| 47 | 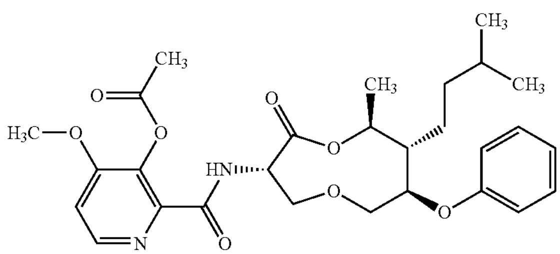 [SMILES: COc1ccnc(C(=O)N[C@H]2COC[C@H](Oc3ccccc3)[C@@H](CCC(C)C)[C@H](C)OC2=O)c1OC(C)=O] | Example 8. | White Powder |
| 48 | 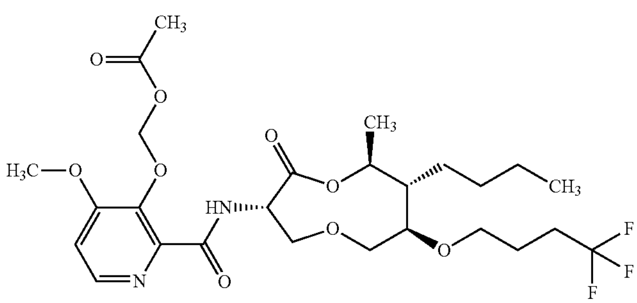 [SMILES: CCCC[C@H]1[C@H](C)OC(=O)[C@@H](NC(=O)c2nccc(OC)c2OCOC(C)=O)COC[C@@H]1OCCCC(F)(F)F] | Example 7. | Colorless Oil |
| 49 | 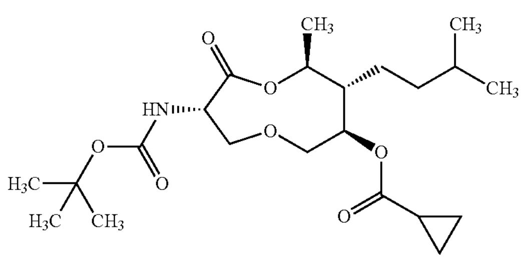 [SMILES: CC(C)CC[C@H]1[C@H](C)OC(=O)[C@@H](NC(=O)OC(C)(C)C)COC[C@@H]1OC(=O)C1CC1] | Example 5, Step 2. | White Solid |

TABLE 1-continued

Compound Structure and Appearance

| Compound Number | Structure | Prepared According To Example | Appearance |
| --- | --- | --- | --- |
| 50 | 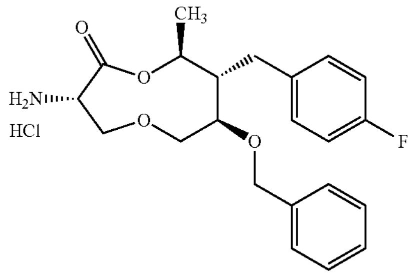 [SMILES: Cl ; C[C@@H]1OC(=O)[C@@H](N)COC[C@H](OCc2ccccc2)[C@H]1Cc1ccc(F)cc1] | Example 6, Step 1a. | White Solid |
| 51 | 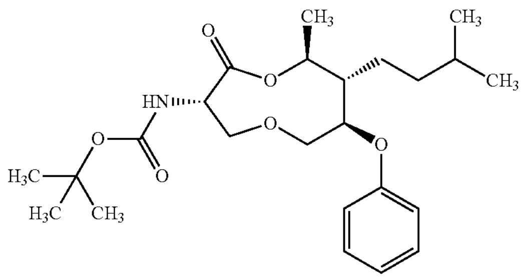 [SMILES: CC(C)CC[C@H]1[C@H](C)OC(=O)[C@@H](NC(=O)OC(C)(C)C)COC[C@@H]1Oc1ccccc1] | Example 1, Steps 1-5; Example 2, Step 1; Example 3, Steps 1-4; Example 4. | Colorless Oil |
| 52 | 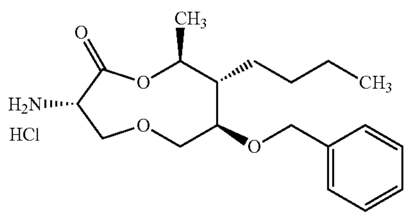 [SMILES: Cl ; CCCC[C@H]1[C@H](C)OC(=O)[C@@H](N)COC[C@@H]1OCc1ccccc1] | Example 6, Step 1a. | White Solid |
| 53 | 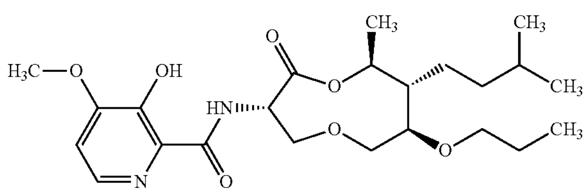 [SMILES: CCCO[C@H]1COC[C@H](NC(=O)c2nccc(OC)c2O)C(=O)O[C@@H](C)[C@@H]1CCC(C)C] | Example 6, Step 2. | Sticky White Solid |
| 54 | 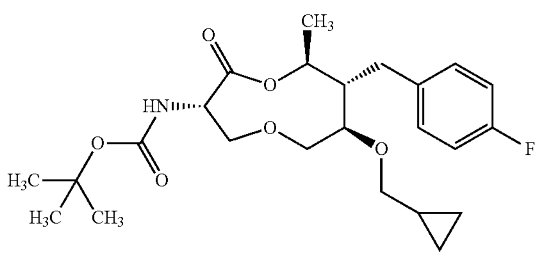 [SMILES: C[C@@H]1OC(=O)[C@@H](NC(=O)OC(C)(C)C)COC[C@H](OCC2CC2)[C@H]1Cc1ccc(F)cc1] | Example 1, Steps 1, 3-5; Example 2, Step 3; Example 3, Steps 1-4; Example 4. | Pale Yellow Oil |
| 55 | 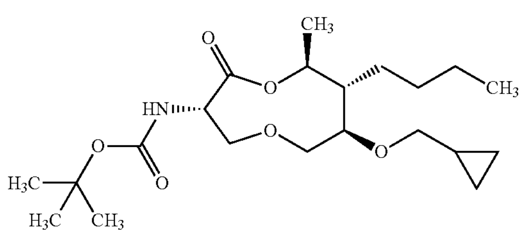 [SMILES: CCCC[C@H]1[C@H](C)OC(=O)[C@@H](NC(=O)OC(C)(C)C)COC[C@@H]1OCC1CC1] | Example 1, Steps 1-5; Example 2, Step 2; Example 3, Steps 1-4; Example 4. | Colorless Oil |

TABLE 1-continued

Compound Structure and Appearance

| Compound Number | Structure | Prepared According To Example | Appearance |
|---|---|---|---|
| 56 | 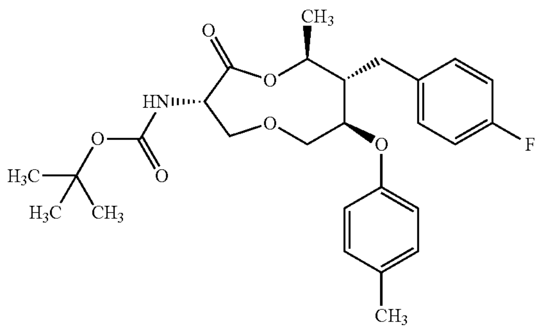 [SMILES: Cc1ccc(O[C@H]2COC[C@H](NC(=O)OC(C)(C)C)C(=O)O[C@@H](C)[C@@H]2Cc2ccc(F)cc2)cc1] | Example 1, Steps 1, 3-5; Example 2, Step 1; Example 3, Steps 1-4; Example 4. | White Foam |
| 57 | 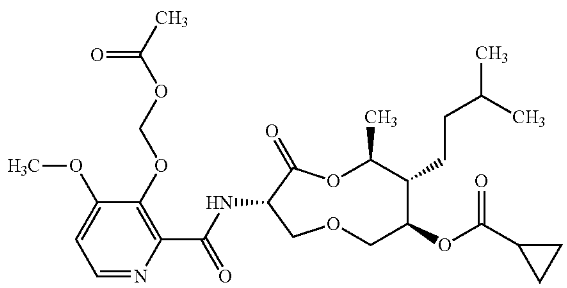 [SMILES: COc1ccnc(C(=O)N[C@H]2COC[C@H](OC(=O)C3CC3)[C@@H](CCC(C)C)[C@H](C)OC2=O)c1OCOC(C)=O] | Example 7. | White Powder |
| 58 | 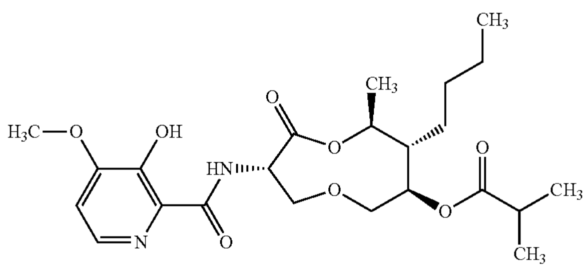 [SMILES: CCCC[C@H]1[C@H](C)OC(=O)[C@@H](NC(=O)c2nccc(OC)c2O)COC[C@@H]1OC(=O)C(C)C] | Example 6, Step 2. | White Solid |
| 59 | 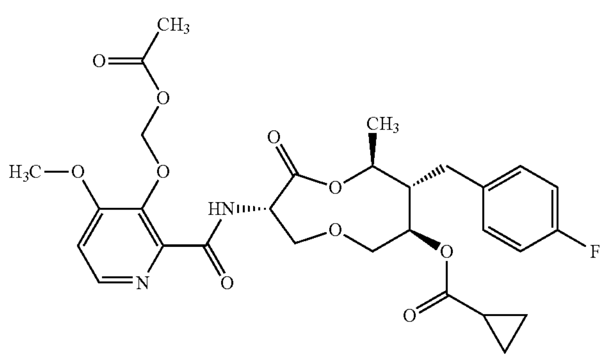 [SMILES: COc1ccnc(C(=O)N[C@H]2COC[C@H](OC(=O)C3CC3)[C@@H](Cc3ccc(F)cc3)[C@H](C)OC2=O)c1OCOC(C)=O] | Example 7. | White Foam |
| 60 | 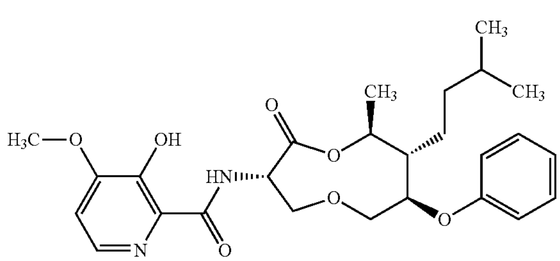 [SMILES: COc1ccnc(C(=O)N[C@H]2COC[C@H](Oc3ccccc3)[C@@H](CCC(C)C)[C@H](C)OC2=O)c1O] | Example 6, Step 2. | White Powder |

TABLE 1-continued

Compound Structure and Appearance

| Compound Number | Structure | Prepared According To Example | Appearance |
|---|---|---|---|
| 61 | 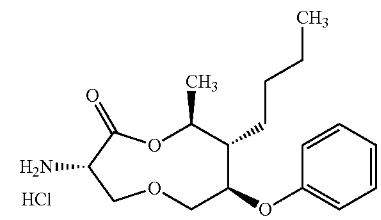 [SMILES: Cl ; CCCC[C@H]1[C@H](C)OC(=O)[C@@H](N)COC[C@@H]1Oc1ccccc1] | Example 6, Step 1a. | Colorless Oil |
| 62 | 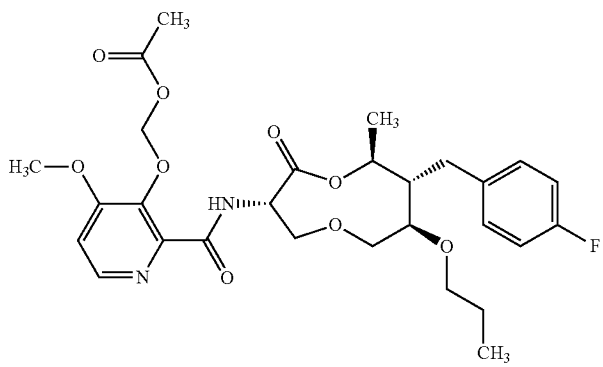 [SMILES: CCCO[C@H]1COC[C@H](NC(=O)c2nccc(OC)c2OCOC(C)=O)C(=O)O[C@@H](C)[C@@H]1Cc1ccc(F)cc1] | Example 7. | White Foam |
| 63 | 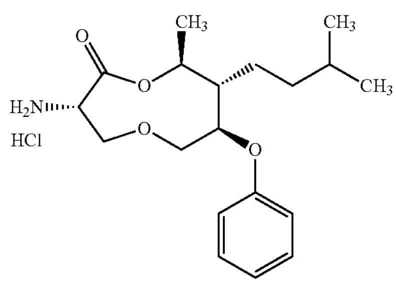 [SMILES: Cl ; CC(C)CC[C@H]1[C@H](C)OC(=O)[C@@H](N)COC[C@@H]1Oc1ccccc1] | Example 6, Step 1a. | White Powder |
| 64 | 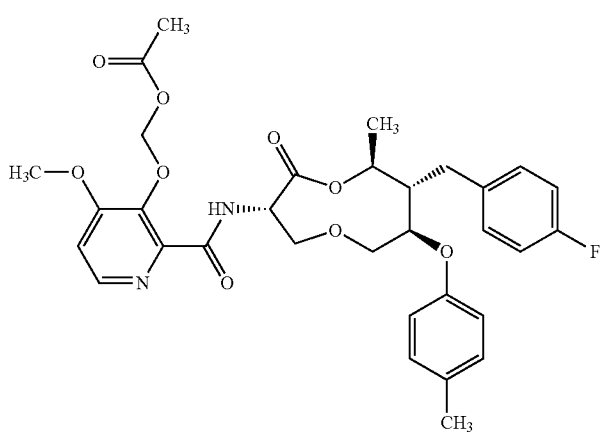 [SMILES: COc1ccnc(C(=O)N[C@H]2COC[C@H](Oc3ccc(C)cc3)[C@@H](Cc3ccc(F)cc3)[C@H](C)OC2=O)c1OCOC(C)=O] | Example 7. | White Foam |
| 65 | 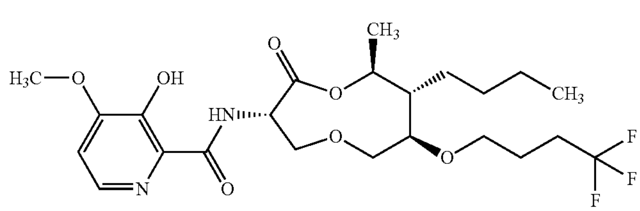 [SMILES: CCCC[C@H]1[C@H](C)OC(=O)[C@@H](NC(=O)c2nccc(OC)c2O)COC[C@@H]1OCCCC(F)(F)F] | Example 6, Step 2. | White Solid |

TABLE 1-continued

Compound Structure and Appearance

| Compound Number | Structure | Prepared According To Example | Appearance |
|---|---|---|---|
| 66 | 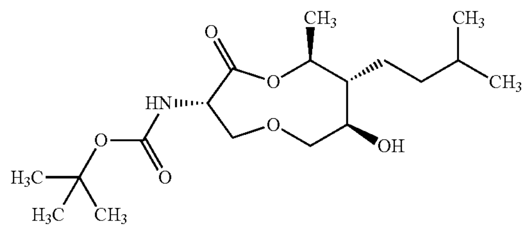 [SMILES: CC(C)CC[C@H]1[C@H](C)OC(=O)[C@@H](NC(=O)OC(C)(C)C)COC[C@@H]1O] | Example 5, Step 1. | White Solid |
| 67 | 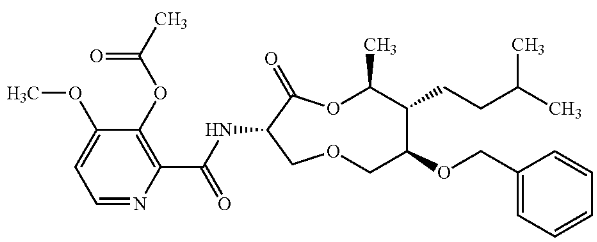 [SMILES: COc1ccnc(C(=O)N[C@H]2COC[C@H](OCc3ccccc3)[C@@H](CCC(C)C)[C@H](C)OC2=O)c1OC(C)=O] | Example 8. | White Powder |
| 68 | 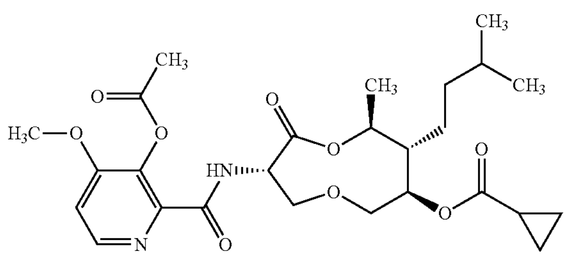 [SMILES: COc1ccnc(C(=O)N[C@H]2COC[C@H](OC(=O)C3CC3)[C@@H](CCC(C)C)[C@H](C)OC2=O)c1OC(C)=O] | Example 8. | White Powder |
| 69 | 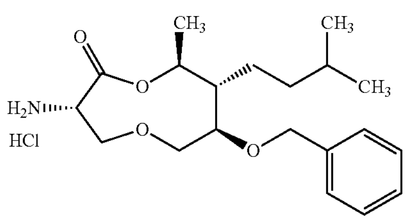 [SMILES: Cl ; CC(C)CC[C@H]1[C@H](C)OC(=O)[C@@H](N)COC[C@@H]1OCc1ccccc1] | Example 6, Step 1a. | White Powder |
| 70 | 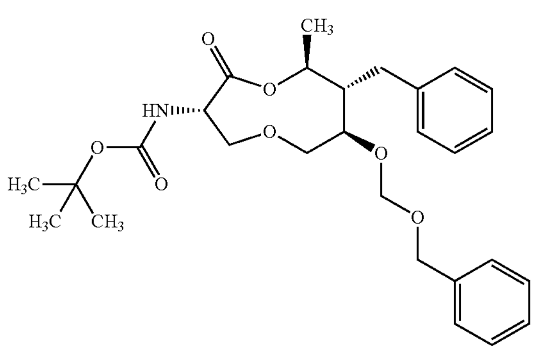 [SMILES: C[C@@H]1OC(=O)[C@@H](NC(=O)OC(C)(C)C)COC[C@H](OCOCc2ccccc2)[C@H]1Cc1ccccc1] | Example 1, Steps 1, 3-5; Example 2, Step 2; Example 3, Steps 1-4; Example 4. | Colorless Oil |

TABLE 1-continued

Compound Structure and Appearance

| Compound Number | Structure | Prepared According To Example | Appearance |
|---|---|---|---|
| 71 | 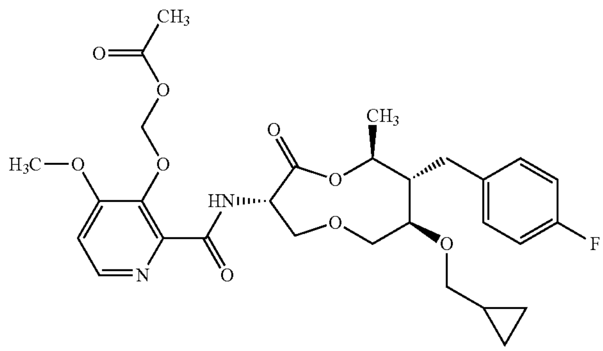 [SMILES: COc1ccnc(C(=O)N[C@H]2COC[C@H](OCC3CC3)[C@@H](Cc3ccc(F)cc3)[C@H](C)OC2=O)c1OCOC(C)=O] | Example 7. | Pale Yellow Foam |
| 72 | 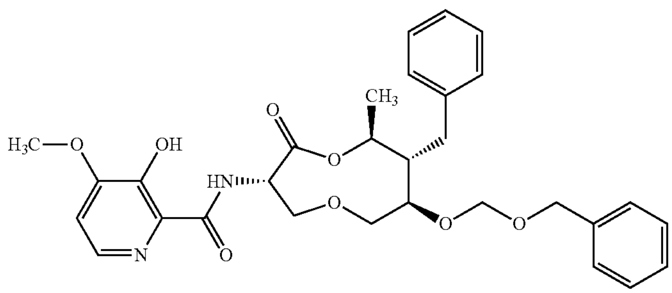 [SMILES: COc1ccnc(C(=O)N[C@H]2COC[C@H](OCOCc3ccccc3)[C@@H](Cc3ccccc3)[C@H](C)OC2=O)c1O] | Example 6, Step 2. | Foam |
| 73 | 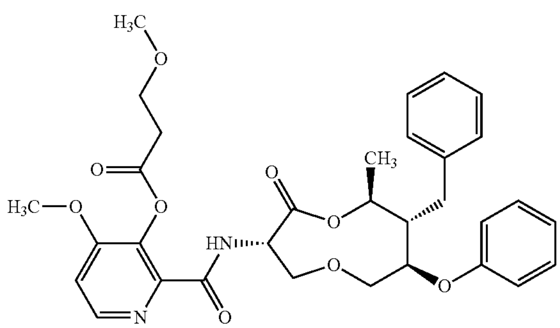 [SMILES: COCCC(=O)Oc1c(OC)ccnc1C(=O)N[C@H]1COC[C@H](Oc2ccccc2)[C@@H](Cc2ccccc2)[C@H](C)OC1=O] | Example 8. | Clear Gel |
| 74 | 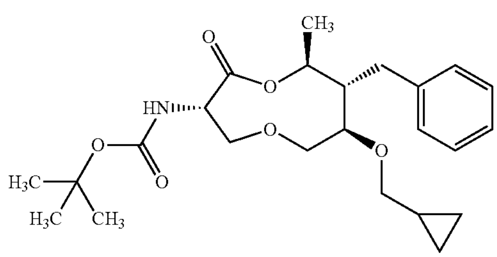 [SMILES: C[C@@H]1OC(=O)[C@@H](NC(=O)OC(C)(C)C)COC[C@H](OCC2CC2)[C@H]1Cc1ccccc1] | Example 1, Steps 1, 3, 6, 7, 8; Example 2, Step 3; Example 3, Steps 1-4; Example 4. | Clear Oil |
| 75 | 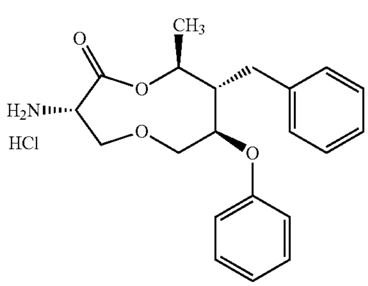 [SMILES: Cl ; C[C@@H]1OC(=O)[C@@H](N)COC[C@H](Oc2ccccc2)[C@H]1Cc1ccccc1] | Example 6, Step 1a. | White Solid |

TABLE 1-continued

Compound Structure and Appearance

| Compound Number | Structure | Prepared According To Example | Appearance |
|---|---|---|---|
| 76 | 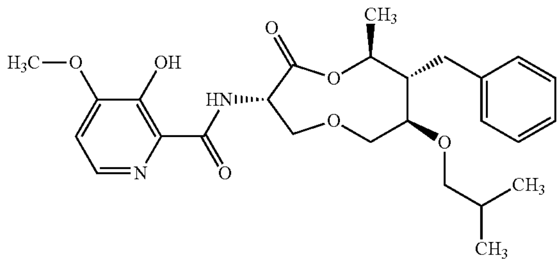 [SMILES: COc1ccnc(C(=O)N[C@H]2COC[C@H](OCC(C)C)[C@@H](Cc3ccccc3)[C@H](C)OC2=O)c1O] | Example 6, Step 2. | Clear Gel |
| 77 | 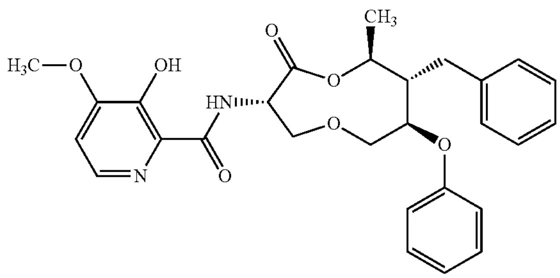 [SMILES: COc1ccnc(C(=O)N[C@H]2COC[C@H](Oc3ccccc3)[C@@H](Cc3ccccc3)[C@H](C)OC2=O)c1O] | Example 6, Step 2. | Pink Solid |
| 78 | 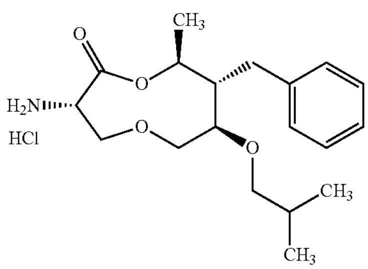 [SMILES: Cl ; CC(C)CO[C@H]1COC[C@H](N)C(=O)O[C@@H](C)[C@@H]1Cc1ccccc1] | Example 6, Step 1a. | Tan Solid |
| 79 | 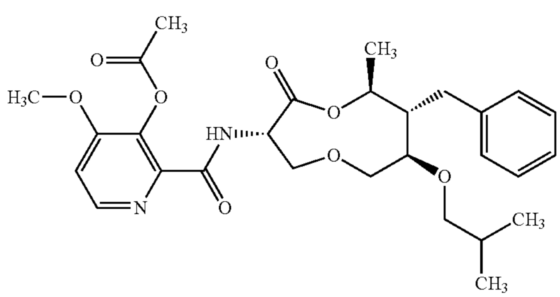 [SMILES: COc1ccnc(C(=O)N[C@H]2COC[C@H](OCC(C)C)[C@@H](Cc3ccccc3)[C@H](C)OC2=O)c1OC(C)=O] | Example 8. | White Solid |
| 80 | 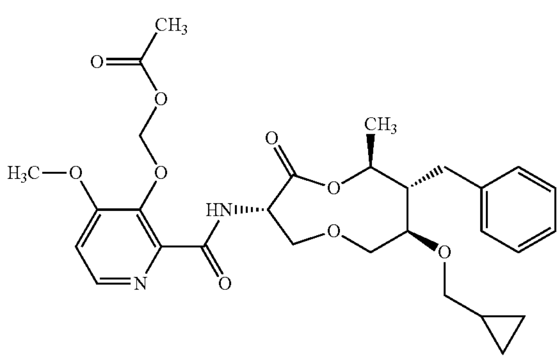 [SMILES: COc1ccnc(C(=O)N[C@H]2COC[C@H](OCC3CC3)[C@@H](Cc3ccccc3)[C@H](C)OC2=O)c1OCOC(C)=O] | Example 7. | Yellow Gel |

TABLE 1-continued

Compound Structure and Appearance

| Compound Number | Structure | Prepared According To Example | Appearance |
|---|---|---|---|
| 81 | 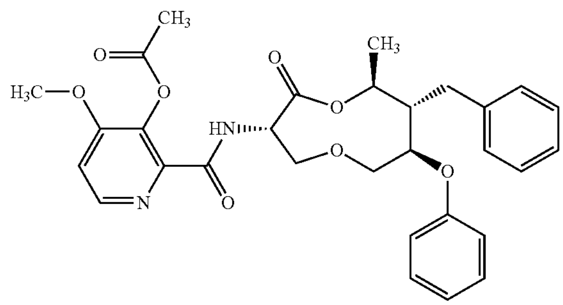 [SMILES: COc1ccnc(C(=O)N[C@H]2COC[C@H](Oc3ccccc3)[C@@H](Cc3ccccc3)[C@H](C)OC2=O)c1OC(C)=O] | Example 8. | White Solid |
| 82 | 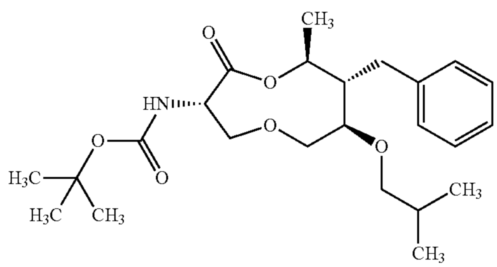 [SMILES: CC(C)CO[C@H]1COC[C@H](NC(=O)OC(C)(C)C)C(=O)O[C@@H](C)[C@@H]1Cc1ccccc1] | Example 1, Steps 1, 3, 6, 7, 8; Example 2, Step 2; Example 3, Steps 1-4; Example 4. | Clear Oil |
| 83 | 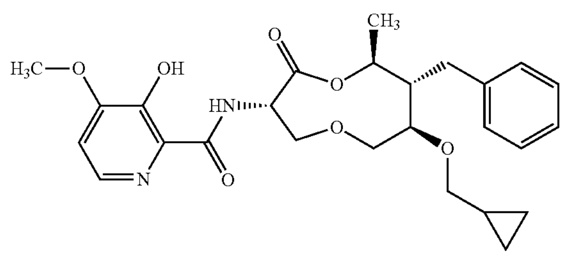 [SMILES: COc1ccnc(C(=O)N[C@H]2COC[C@H](OCC3CC3)[C@@H](Cc3ccccc3)[C@H](C)OC2=O)c1O] | Example 6, Step 2. | White Foam |
| 84 | 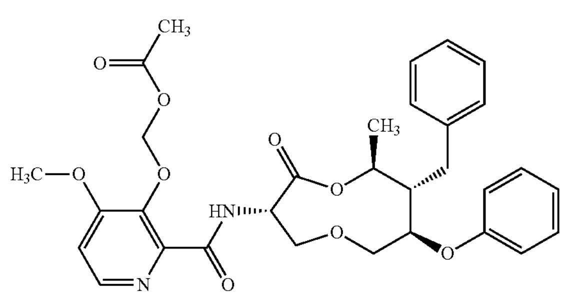 [SMILES: COc1ccnc(C(=O)N[C@H]2COC[C@H](Oc3ccccc3)[C@@H](Cc3ccccc3)[C@H](C)OC2=O)c1OCOC(C)=O] | Example 7. | Yellow Gel |
| 85 | 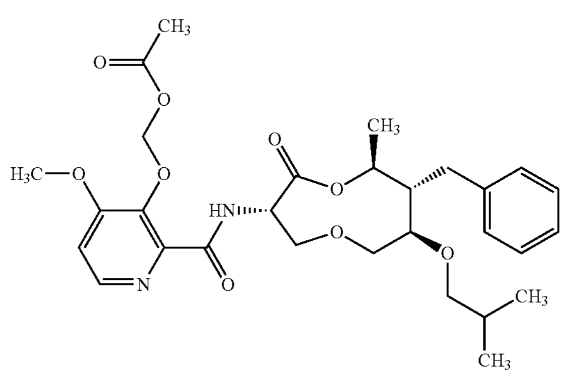 [SMILES: COc1ccnc(C(=O)N[C@H]2COC[C@H](OCC(C)C)[C@@H](Cc3ccccc3)[C@H](C)OC2=O)c1OCOC(C)=O] | Example 7. | Yellow Gel |

TABLE 1-continued

Compound Structure and Appearance

| Compound Number | Structure | Prepared According To Example | Appearance |
|---|---|---|---|
| 86 | 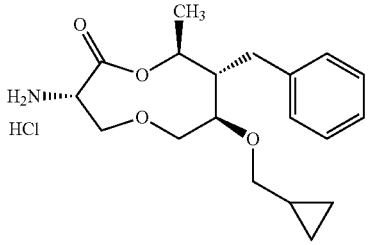 [SMILES: Cl ; C[C@@H]1OC(=O)[C@@H](N)COC[C@H](OCC2CC2)[C@H]1Cc1ccccc1] | Example 6, Step 1a. | White Solid |
| 87 | 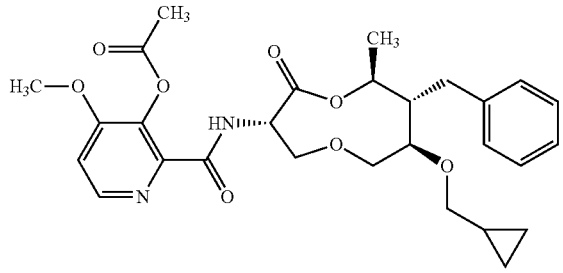 [SMILES: COc1ccnc(C(=O)N[C@H]2COC[C@H](OCC3CC3)[C@@H](Cc3ccccc3)[C@H](C)OC2=O)c1OC(C)=O] | Example 8. | White Foam |

TABLE 2

Analytical Data

| Cmpd. No. | MP (° C.) | IR (cm$^{-1}$) | MASS | $^1$H NMR | $^{13}$C or $^{19}$F NMR |
|---|---|---|---|---|---|
| 1 | — | — | ESIMS m/z 420 ([M + Na]$^+$) | $^1$H NMR (CDCl$_3$) δ 7.24-7.17 (m, 2H), 6.96 (t, J = 8.7 Hz, 2H), 5.54 (d, J = 8.3 Hz, 1H), 4.98 (dq, J = 9.0, 6.3 Hz, 1H), 4.70-4.49 (m, 1H), 4.00 (dd, J = 11.9, 6.6 Hz, 1H), 3.83-3.72 (m, 2H), 3.61 (dd, J = 11.9, 5.3 Hz, 1H), 3.55-3.42 (m, 1H), 2.94-2.76 (m, 3H), 2.14 (tt, J = 9.1, 5.4 Hz, 1H), 1.43 (s, 9H), 1.36 (d, J = 6.4 Hz, 3H) | $^{19}$F NMR (CDCl$_3$) δ −116.84 |
| 2 | — | — | ESIMS m/z 368 ([M + Na]$^+$) | $^1$H NMR (CDCl$_3$) δ 5.48 (d, J = 8.3 Hz, 1H), 5.03-4.90 (m, 1H), 4.67-4.56 (m, 1H), 4.00 (dd, J = 11.8, 6.7 Hz, 1H), 3.82-3.70 (m, 2H), 3.60 (dd, J = 11.8, 5.5 Hz, 1H), 3.56-3.48 (m, 1H), 2.33 (d, J = 6.2 Hz, 1H), 1.82 (tt, J = 9.1, 4.2 Hz, 1H), 1.69-1.58 (m, 1H), 1.44 (s, 9H), 1.39 (d, J = 6.4 Hz, 3H), 1.35-1.22 (m, 5H), 0.90 (t, J = 6.9 Hz, 3H) | $^{13}$C NMR (CDCl$_3$) δ 171.68, 155.21, 80.16, 80.05, 74.03, 73.87, 72.94, 53.59, 50.52, 28.39, 28.27, 27.28, 23.28, 20.04, 13.93 |
| 3 | — | (Thin Film) 3345, 2947, 2868, 1741, 1651 | ESIMS m/z 451 ([M + H]$^+$) | $^1$H NMR (CDCl$_3$) δ 11.99 (d, J = 0.7 Hz, 1H), 8.73 (d, J = 8.0 Hz, 1H), 8.00 (d, J = 5.2 Hz, 1H), 6.87 (d, J = 5.2 Hz, 1H), 5.13 (dq, J = 10.4, 6.3 Hz, 1H), 5.02 (ddd, J = 8.0, 6.2, 3.9 Hz, 1H), 4.09-3.95 (m, 2H), 3.96-3.90 (m, 4H), 3.64 (dd, J = 11.2, 6.3 Hz, | — |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 1H), 3.43 (dd, J = 10.0, 6.9 Hz, 1H), 3.17 (dd, J = 10.0, 6.8 Hz, 1H), 3.11 (ddd, J = 10.0, 6.4, 1.1 Hz, 1H), 1.88 (tt, J = 10.1, 3.9 Hz, 1H), 1.73 (ddt, J = 12.5, 10.3, 4.1 Hz, 1H), 1.40 (d, J = 6.3 Hz, 3H), 1.39-1.19 (m, 5H), 1.03 (dddd, J = 12.8, 6.8, 5.0, 2.6 Hz, 1H), 0.97-0.87 (t, J = 6.9 Hz, 3H), 0.60-0.47 (m, 2H), 0.24-0.14 (m, 2H) | |
| 4 | — | — | ESIMS m/z 462 ([M + Na]⁺) | ¹H NMR (CDCl₃) δ 7.20-7.12 (m, 2H), 7.00-6.89 (m, 2H), 5.41-5.32 (m, 1H), 5.08 (dq, J = 9.6, 6.4 Hz, 1H), 4.66-4.52 (m, 1H), 4.02-3.88 (m, 2H), 3.86-3.76 (m, 1H), 3.64 (dd, J = 11.5, 5.7 Hz, 1H), 3.53 (dt, J = 9.0, 6.6 Hz, 1H), 3.23 (dt, J = 9.0, 6.6 Hz, 1H), 3.02 (ddd, J = 9.7, 5.7, 1.4 Hz, 1H), 2.91 (dd, J = 14.6, 4.1 Hz, 1H), 2.67 (dd, J = 14.7, 6.1 Hz, 1H), 2.21-2.05 (m, 1H), 1.57 (p, J = 6.8 Hz, 2H), 1.43 (s, 9H), 1.29 (d, J = 6.3 Hz, 3H), 0.90 (t, J = 7.4 Hz, 3H) | ¹³C NMR (CDCl₃) δ 170.94, 161.34 (d, J = 244.1 Hz), 155.21, 135.97 (d, J = 3.4 Hz), 130.49 (d, J = 7.8 Hz), 115.07 (d, J = 21.0 Hz), 81.83, 80.00, 79.09, 75.30, 73.70, 70.94, 54.48, 51.98, 34.69, 28.28, 23.13, 20.70, 10.72 |
| 5 | — | — | ESIMS m/z 488 ([M + Na]⁺) | ¹H NMR (CDCl₃) δ 7.15 (dd, J = 8.5, 5.5 Hz, 2H), 6.97 (t, J = 8.7 Hz, 2H), 5.42 (d, J = 8.2 Hz, 1H), 5.16-5.01 (m, 1H), 4.72 (ddd, J = 9.4, 4.7, 2.6 Hz, 1H), 4.67 (ddd, J = 8.2, 6.3, 4.5 Hz, 1H), 4.01 (dd, J = 11.6, 6.4 Hz, 1H), 3.83-3.73 (m, 2H), 3.69 (dd, J = 11.6, 4.6 Hz, 1H), 2.76 (dd, J = 14.8, 6.3 Hz, 1H), 2.65 (dd, J = 14.8, 5.6 Hz, 1H), 2.45 (td, J = 8.9, 4.4 Hz, 1H), 1.52-1.46 (m, 1H), 1.43 (s, 9H), 1.37 (d, J = 6.4 Hz, 3H), 0.98-0.92 (m, 2H), 0.87-0.81 (m, 2H) | ¹⁹F NMR (CDCl₃) δ −116.80 |
| 6 | — | (Thin Film) 3377, 2934, 2873, 1748, 1676 | HRMS-ESI (m/z) [M + H]⁺ calcd for C₂₆H₃₈N₂O₉, 523.2650; found, 523.2659 | ¹H NMR (CDCl₃) δ 8.59 (d, J = 7.8 Hz, 1H), 8.29 (d, J = 5.4 Hz, 1H), 6.95 (d, J = 5.4 Hz, 1H), 5.78-5.70 (m, 2H), 5.15-5.01 (m, 2H), 4.06-3.95 (m, 2H), 3.93-3.86 (m, 4H), 3.64 (dd, J = 11.1, 6.4 Hz, 1H), 3.42 (dd, J = 10.0, 6.9 Hz, 1H), 3.16 (dd, J = 10.0, 6.8 Hz, 1H), 3.10 (ddd, J = 10.0, 6.5, 1.2 Hz, 1H), 2.07 (s, 3H), 1.93-1.82 (m, 1H), 1.79-1.68 (m, 1H), 1.39 (d, J = 6.3 Hz, 3H), 1.36-1.17 (m, 5H), 1.02 (dddd, J = 12.9, 6.8, 5.0, 2.6 Hz, 1H), 0.90 (t, J = 6.9 Hz, 3H), 0.60-0.45 (m, 2H), 0.24-0.13 (m, 2H) | — |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| 7 | — | — | ESIMS m/z 510 ([M + Na]$^+$) | $^1$H NMR (CDCl$_3$) δ 7.36-7.22 (m, 5H), 7.11 (dd, J = 8.5, 5.5 Hz, 2H), 6.91 (t, J = 8.7 Hz, 2H), 5.45 (d, J = 8.0 Hz, 1H), 5.11 (dt, J = 12.6, 6.3 Hz, 1H), 4.63 (d, J = 11.5 Hz, 2H), 4.36 (d, J = 11.5 Hz, 1H), 4.10 (d, J = 11.6 Hz, 1H), 3.97 (dd, J = 12.1, 5.9 Hz, 1H), 3.85 (dd, J = 12.1, 3.5 Hz, 1H), 3.72 (dd, J = 11.7, 5.7 Hz, 1H), 3.21 (ddd, J = 9.6, 5.7, 1.4 Hz, 1H), 2.89 (dd, J = 14.7, 4.3 Hz, 1H), 2.71 (dd, J = 14.7, 6.0 Hz, 1H), 2.19 (dtd, J = 9.7, 6.5, 6.1, 3.6 Hz, 1H), 1.44 (s, 9H), 1.31 (d, J = 6.4 Hz, 3H) | $^{19}$F NMR (CDCl$_3$) δ −117.05 |
| 8 | — | — | HRMS-ESI (m/z) [M + H]$^+$ calcd for C$_{30}$H$_{40}$FN$_2$O$_{10}$, 607.2662; found, 607.2673 | $^1$H NMR (CDCl$_3$) δ 8.60 (d, J = 7.8 Hz, 1H), 8.28 (d, J = 5.4 Hz, 1H), 7.18 (dd, J = 8.5, 5.6 Hz, 2H), 6.97 (t, J = 8.7 Hz, 2H), 6.96 (d, J = 5.5 Hz, 1H), 5.81 (s, 2H), 5.12 (dq, J = 9.6, 6.3 Hz, 1H), 5.02 (ddd, J = 7.8, 6.1, 3.8 Hz, 1H), 4.09 (s, 2H), 4.06 (dd, J = 11.7, 5.8 Hz, 1H), 4.00 (d, J = 10.0 Hz, 1H), 3.96-3.91 (m, 1H), 3.90 (s, 3H), 3.71 (dd, J = 11.5, 5.8 Hz, 1H), 3.58 (q, J = 7.0 Hz, 2H), 3.55-3.52 (m, 1H), 3.25 (dt, J = 9.0, 6.6 Hz, 1H), 3.08 (dd, J = 10.3, 5.1 Hz, 1H), 2.92 (dd, J = 14.7, 4.1 Hz, 1H), 2.71 (dd, J = 14.7, 6.0 Hz, 1H), 2.22-2.10 (m, 1H), 1.65-1.50 (m, 2H), 1.32 (d, J = 6.3 Hz, 3H), 1.22 (t, J = 7.0 Hz, 3H), 0.91 (t, J = 7.4 Hz, 3H) | $^{19}$F NMR (CDCl$_3$) δ −117.38 |
| 9 | — | (Thin Film) 3376, 2934, 2873, 1771, 1745 | HRMS-ESI (m/z) [M + H]$^+$ calcd for C$_{25}$H$_{36}$N$_2$O$_8$, 493.2544; found 493.2557 | $^1$H NMR (CDCl$_3$) δ 8.75 (s, 1H), 8.35 (d, J = 5.4 Hz, 1H), 7.00 (d, J = 5.5 Hz, 1H), 5.14-4.98 (m, 2H), 4.05-3.94 (m, 2H), 3.91 (s, 3H), 3.86 (dd, J = 12.0, 4.1 Hz, 1H), 3.63 (dd, J = 11.0, 6.5 Hz, 1H), 3.42 (dd, J = 10.0, 6.9 Hz, 1H), 3.16 (dd, J = 10.0, 6.8 Hz, 1H), 3.10 (dd, J = 9.9, 6.3 Hz, 1H), 2.39 (s, 3H), 1.92-1.81 (m, 1H), 1.80-1.67 (m, 1H), 1.38 (d, J = 6.3 Hz, 3H), 1.35-1.18 (m, 5H), 1.08-0.97 (m, 1H), 0.95-0.84 (m, 3H), 0.59-0.47 (m, 2H), 0.24-0.13 (m, 2H) | — |
| 10 | — | — | HRMS-ESI (m/z) [M + H]$^+$ calcd for C$_{31}$H$_{34}$FN$_2$O$_8$, 581.2294; found, 581.2303 | $^1$H NMR (CDCl$_3$) δ 8.79 (d, J = 8.1 Hz, 1H), 8.35 (d, J = 5.4 Hz, 1H), 7.12-7.05 (m, 4H), 7.00 (d, J = 5.5 Hz, 1H), 6.91 (t, J = 8.7 Hz, 2H), 6.74 (d, J = 8.5 Hz, 2H), 5.20 (dq, J = 10.1, 6.2 Hz, 1H), 5.06 (ddd, J = 8.1, 6.1, 3.5 Hz, 1H), 4.06-3.93 (m, 3H), | $^{19}$F NMR (CDCl$_3$) δ −116.96 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
|  |  |  |  | 3.95-3.87 (m, 1H), 3.89 (s, 3H), 3.73 (dd, J = 11.2, 6.2 Hz, 1H), 2.95 (dd, J = 14.7, 4.9 Hz, 1H), 2.83 (dd, J = 14.7, 4.3 Hz, 1H), 2.44-2.38 (m, 1H), 2.38 (s, 3H), 2.28 (s, 3H), 1.48 (d, J = 6.3 Hz, 3H) |  |
| 11 | — | — | ESIMS m/z 302 ([M + H]$^+$) | — | — |
| 12 | — | — | ESIMS m/z 478.4 ([M + Na]$^+$) | $^1$H NMR (CDCl$_3$) δ 7.32-7.10 (m, 7H), 6.96 (t, J = 7.4 Hz, 1H), 6.83 (d, J = 9.7 Hz, 2H), 5.39 (d, J = 7.9 Hz, 1H), 5.26-5.12 (m, 1H), 4.71-4.59 (m, 1H), 4.07-3.82 (m, 4H), 3.72 (dd, J = 11.4, 6.1 Hz, 1H), 2.95-2.85 (m, 2H), 2.51-2.33 (m, 1H), 1.46 (d, J = 6.4 Hz, 3H), 1.44 (s, 9H) | — |
| 13 | — | — | ESIMS m/z 300 ([M + H]$^+$) | $^1$H NMR (CDCl$_3$) δ 8.70 (bs, 3H), 5.06 (dq, J = 12.2, 6.2 Hz, 1H), 4.60 (dd, J = 5.8, 3.2 Hz, 1H), 4.34 (d, J = 13.3 Hz, 1H), 4.13-3.90 (m, 2H), 3.56 (dd, J = 11.3, 6.1 Hz, 1H), 3.42 (dd, J = 10.1, 6.8 Hz, 1H), 3.16 (dd, J = 10.0, 6.8 Hz, 1H), 3.09 (dd, J = 10.0, 6.0 Hz, 1H), 1.90-1.78 (m, 1H), 1.76-1.62 (m, 1H), 1.39 (d, J = 6.2 Hz, 3H), 1.35-1.19 (m, 5H), 1.07-0.96 (m, 1H), 0.91 (t, J = 6.8 Hz, 3H), 0.51 (d, J = 8.0 Hz, 2H), 0.25-0.13 (m, 2H) | $^{13}$C NMR (CDCl$_3$) δ 168.36, 80.25, 79.95, 74.80, 74.29, 71.11, 53.89, 49.92, 27.99, 27.09, 23.33, 19.78, 13.94, 10.70, 2.96 |
| 14 | — | (Thin Film) 3378, 2952, 2871, 1748, 1676, 1502, 1200 | HRMS-ESI (m/z) [M + H]$^+$ calcd for C$_{30}$H$_{41}$N$_2$O$_9$, 573.2807; found, 573.2823 | $^1$H NMR (CDCl$_3$) δ 8.62 (d, J = 7.8 Hz, 1H), 8.30 (d, J = 5.4 Hz, 1H), 7.38-7.25 (m, 5H), 6.96 (d, J = 5.4 Hz, 1H), 5.78-5.70 (m, 2H), 5.18-5.02 (m, 2H), 4.65 (d, J = 11.2 Hz, 1H), 4.38 (d, J = 11.2 Hz, 1H), 4.15-4.02 (m, 2H), 3.98-3.88 (m, 4H), 3.73 (dd, J = 11.2, 6.3 Hz, 1H), 3.28 (dd, J = 9.9, 6.0 Hz, 1H), 2.07 (s, 3H), 1.99-1.86 (m, 1H), 1.80-1.66 (m, 1H), 1.47-1.29 (m, 5H), 1.20-1.00 (m, 2H), 0.84 (app t, J = 7.1 Hz, 6H) | — |
| 15 | — | — | ESIMS m/z 366 ([M + H]$^+$) | — | — |
| 16 | — | — | ESIMS m/z 400 ([M + H]$^+$) | — | — |
| 17 | — | — | HRMS-ESI (m/z) [M + H]$^+$ calcd for C$_{25}$H$_{32}$FN$_2$O$_7$, 491.2188; found, 491.2198 | $^1$H NMR (CDCl$_3$) δ 11.97 (d, J = 0.6 Hz, 1H), 8.72 (d, J = 8.0 Hz, 1H), 8.01 (d, J = 5.2 Hz, 1H), 7.23-7.13 (m, 2H), 6.97 (t, J = 8.7 Hz, 2H), 6.87 (d, J = 5.4 Hz, 1H), 5.15 (dq, J = 9.5, 6.3 Hz, 1H), 5.01 (ddd, J = 8.0, 6.0, 3.6 Hz, 1H), 4.08 (dd, J = 12.1, | $^{19}$F NMR (CDCl$_3$) δ −117.30 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 6.0 Hz, 1H), 4.02 (d, J = 11.2 Hz, 1H), 3.96 (dd, J = 12.1, 3.6 Hz, 1H), 3.94 (s, 3H), 3.71 (dd, J = 11.6, 5.7 Hz, 1H), 3.55 (dt, J = 9.0, 6.7 Hz, 1H), 3.26 (dt, J = 8.9, 6.6 Hz, 1H), 3.09 (ddd, J = 9.8, 5.6, 1.3 Hz, 1H), 2.93 (dd, J = 14.7, 4.2 Hz, 1H), 2.71 (dd, J = 14.6, 6.1 Hz, 1H), 2.23-2.09 (m, 1H), 1.67-1.50 (m, 2H), 1.33 (d, J = 6.3 Hz, 3H), 0.91 (t, J = 7.4 Hz, 3H) | |
| 18 | — | (Thin Film) 3380, 2955, 2873, 1749, 1676, 1503, 1200, 1086 | HRMS-ESI (m/z) [M + H]$^+$ calcd for C$_{26}$H$_{41}$N$_2$O$_9$, 525.2807; found, 525.2805 | $^1$H NMR (CDCl$_3$) δ 8.60 (d, J = 7.8 Hz, 1H), 8.29 (d, J = 5.4 Hz, 1H), 6.96 (d, J = 5.4 Hz, 1H), 5.78-5.69 (m, 2H), 5.16-5.00 (m, 2H), 4.08-3.86 (m, 6H), 3.68-3.52 (m, 2H), 3.31-3.15 (m, 1H), 3.07 (dd, J = 9.9, 6.2 Hz, 1H), 2.07 (s, 3H), 1.92-1.80 (m, 1H), 1.78-1.65 (m, 1H), 1.62-1.31 (m, 7H), 1.25-1.07 (m, 2H), 0.96-0.85 (m, 9H) | — |
| 19 | — | — | ESIMS m/z 352 ([M + H]$^+$) | — | — |
| 20 | — | — | HRMS-ESI (m/z) [M + H]$^+$ calcd for C$_{27}$H$_{34}$FN$_2$O$_8$, 533.2294; found, 533.2307 | $^1$H NMR (CDCl$_3$) δ 8.76 (d, J = 7.9 Hz, 1H), 8.33 (d, J = 5.4 Hz, 1H), 7.18 (dd, J = 8.5, 5.6 Hz, 2H), 7.00 (d, J = 5.5 Hz, 1H), 6.96 (t, J = 8.7 Hz, 2H), 5.11 (dq, J = 9.6, 6.3 Hz, 1H), 5.01 (ddd, J = 8.0, 6.1, 3.8 Hz, 1H), 4.04 (dd, J = 12.2, 6.3 Hz, 1H), 4.00 (d, J = 11.5 Hz, 1H), 3.94-3.85 (m, 1H), 3.89 (s, 3H), 3.69 (dd, J = 11.4, 5.8 Hz, 1H), 3.55 (dt, J = 8.9, 6.6 Hz, 1H), 3.25 (dt, J = 8.9, 6.6 Hz, 1H), 3.07 (ddd, J = 9.8, 5.9, 1.4 Hz, 1H), 2.91 (dd, J = 14.7, 4.0 Hz, 1H), 2.70 (dd, J = 14.7, 6.0 Hz, 1H), 2.38 (s, 3H), 2.15 (tdd, J = 9.8, 6.1, 4.1 Hz, 1H), 1.64-1.50 (m, 2H), 1.31 (d, J = 6.3 Hz, 3H), 0.91 (t, J = 7.4 Hz, 3H) | $^{19}$F NMR (CDCl$_3$) δ −117.35 |
| 21 | — | — | ESIMS m/z 458 ([M + Na]$^+$) | $^1$H NMR (CDCl$_3$) δ 7.39-7.27 (m, 5H), 5.35 (d, J = 8.0 Hz, 1H), 5.07 (dq, J = 12.2, 6.3 Hz, 1H), 4.69-4.59 (m, 2H), 4.36 (d, J = 11.3 Hz, 1H), 4.11-4.03 (m, 1H), 3.95 (dd, J = 12.0, 6.1 Hz, 1H), 3.86-3.78 (m, 1H), 3.66 (dd, J = 11.3, 6.2 Hz, 1H), 3.21 (ddd, J = 9.9, 6.2, 1.2 Hz, 1H), 1.88 (tt, J = 10.1, 3.9 Hz, 1H), 1.74-1.56 (m, 2H), 1.44 (s, 9H), 1.37 (d, J = 6.3 Hz, 3H), 1.29-1.17 (m, 3H), 1.17-1.05 (m, 1H), 0.85 (t, J = 7.0 Hz, 3H) | $^{13}$C NMR (CDCl$_3$) δ 171.19, 155.22, 137.86, 128.39, 127.90, 127.74, 80.71, 80.06, 79.43, 75.31, 73.62, 71.51, 54.36, 49.97, 28.31, 28.02, 26.95, 23.39, 19.93, 13.97 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| 22 | — | — | ESIMS m/z 444 ([M + Na]⁺) | ¹H NMR (CDCl₃) δ 7.32-7.25 (m, 2H), 6.94 (tt, J = 7.4, 1.1 Hz, 1H), 6.90-6.85 (m, 2H), 5.45 (d, J = 8.0 Hz, 1H), 5.19 (dq, J = 10.4, 6.3 Hz, 1H), 4.68 (dt, J = 8.6, 4.5 Hz, 1H), 4.06-3.97 (m, 2H), 3.90 (d, J = 5.1 Hz, 2H), 3.66 (dd, J = 11.3, 6.2 Hz, 1H), 2.09 (tt, J = 10.3, 3.9 Hz, 1H), 1.80-1.67 (m, 1H), 1.45 (s, 9H), 1.42 (d, J = 6.3 Hz, 3H), 1.35-1.10 (m, 5H), 0.81 (t, J = 7.1 Hz, 3H) | ¹³C NMR (CDCl₃) δ 170.94, 157.21, 155.27, 129.65, 120.89, 115.09, 80.18, 80.09, 78.41, 75.86, 73.27, 54.68, 50.18, 28.32, 28.04, 27.02, 23.16, 19.92, 13.83 |
| 23 | — | — | HRMS-ESI (m/z) [M + H]⁺ calcd for C₂₉H₃₂FN₂O₇, 539.2188; found, 539.2194 | ¹H NMR (CDCl₃) δ 11.97 (s, 1H), 8.76 (d, J = 8.0 Hz, 1H), 8.02 (d, J = 5.2 Hz, 1H), 7.14-7.05 (m, 4H), 6.91 (t, J = 8.7 Hz, 2H), 6.88 (d, J = 5.2 Hz, 1H), 6.74 (d, J = 8.5 Hz, 2H), 5.25 (dq, J = 10.0, 6.3 Hz, 1H), 5.06 (dt, J = 8.0, 4.6 Hz, 1H), 4.07 (d, J = 11.3 Hz, 1H), 4.02 (d, J = 4.6 Hz, 2H), 4.00-3.96 (m, 1H), 3.94 (s, 3H), 3.74 (dd, J = 11.4, 6.0 Hz, 1H), 2.97 (dd, J = 14.7, 4.9 Hz, 1H), 2.84 (dd, J = 14.7, 4.3 Hz, 1H), 2.41 (tt, J = 9.8, 4.6 Hz, 1H), 2.29 (s, 3H), 1.50 (d, J = 6.3 Hz, 3H) | ¹⁹F NMR (CDCl₃) δ −116.88 |
| 24 | — | — | HRMS-ESI (m/z) [M + H]⁺ calcd for C₂₆H₃₂FN₂O₇, 503.2188; found, 503.2214 | ¹H NMR (CDCl₃) δ 11.97 (s, 1H), 8.72 (d, J = 8.0 Hz, 1H), 8.05-7.93 (m, 1H), 7.21 (dd, J = 8.4, 5.5 Hz, 2H), 7.03-6.92 (m, 2H), 6.91-6.82 (m, 1H), 5.23-5.10 (m, 1H), 5.01 (ddd, J = 7.7, 6.0, 3.5 Hz, 1H), 4.11-3.96 (m, 3H), 3.94 (s, 3H), 3.71 (dd, J = 11.6, 5.7 Hz, 1H), 3.36 (dd, J = 10.1, 7.1 Hz, 1H), 3.24 (dd, J = 10.1, 6.6 Hz, 1H), 3.12 (dd, J = 9.7, 5.6 Hz, 1H), 2.95 (dd, J = 14.7, 4.1 Hz, 1H), 2.74 (dd, J = 14.7, 5.9 Hz, 1H), 2.18 (tdd, J = 9.8, 5.9, 4.1 Hz, 1H), 1.34 (d, J = 6.3 Hz, 3H), 1.10-0.98 (m, 1H), 0.59-0.49 (m, 2H), 0.26-0.18 (m, 2H) | ¹⁹F NMR (CDCl₃) δ −117.23 |
| 25 | — | — | HRMS-ESI (m/z) [M + H]⁺ calcd for C₂₆H₃₀FN₂O₈, 517.1986; found, 517.1981 | ¹H NMR (CDCl₃) δ 11.95 (s, 1H), 8.72 (d, J = 8.1 Hz, 1H), 7.99 (d, J = 5.2 Hz, 1H), 7.17 (dd, J = 8.5, 5.5 Hz, 2H), 6.98 (t, J = 8.7 Hz, 2H), 6.87 (d, J = 5.2 Hz, 1H), 5.16 (dq, J = 8.1, 6.4 Hz, 1H), 5.07 (ddd, J = 8.1, 6.3, 4.4 Hz, 1H), 4.78 (ddd, J = 9.2, 4.5, 2.7 Hz, 1H), 4.16 (dd, J = 11.6, 6.4 Hz, 1H), 3.93 (s, 3H), 3.88-3.81 (m, 3H), 2.80 (dd, J = 14.7, 6.5 Hz, 1H), 2.68 (dd, J = 14.8, 5.5 Hz, 1H), 2.55-2.44 (m, 1H), 1.51 | ¹⁹F NMR (CDCl₃) δ −116.75 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
|  |  |  |  | (tt, J = 8.0, 4.6 Hz, 1H), 1.40 (d, J = 6.4 Hz, 3H), 1.00-0.94 (m, J = 2.5, 1.9 Hz, 2H), 0.89-0.84 (m, 2H) |  |
| 26 | — | (Thin Film) 3375, 2919, 1746, 1677, 1505 | HRMS-ESI (m/z) [M + H]⁺ calcd for $C_{35}H_{43}N_2O_{11}$, 667.2861; found, 667.2875 | ¹H NMR (CDCl₃) δ 8.58 (d, J = 7.9 Hz, 1H), 8.29 (d, J = 5.4 Hz, 1H), 7.36-7.15 (m, 10H), 6.95 (d, J = 5.4 Hz, 1H), 5.81 (s, 2H), 5.14 (dq, J = 8.3, 6.4 Hz, 1H), 5.06 (ddd, J = 8.0, 6.5, 4.8 Hz, 1H), 4.85 (d, J = 7.1 Hz, 1H), 4.72 (d, J = 7.0 Hz, 1H), 4.67-4.56 (m, 2H), 4.17 (dd, J = 11.7, 6.6 Hz, 1H), 4.09 (s, 2H), 3.96-3.91 (m, 1H), 3.91 (s, 3H), 3.87 (dd, J = 11.6, 5.5 Hz, 1H), 3.82-3.75 (m, 1H), 3.66-3.52 (m, 3H), 3.01 (dd, J = 14.7, 4.4 Hz, 1H), 2.68 (dd, J = 14.7, 7.2 Hz, 1H), 2.41-2.27 (m, 1H), 1.31 (d, J = 6.4 Hz, 3H), 1.22 (t, J = 7.0 Hz, 3H) | — |
| 27 | — | — | ESIMS m/z 438 ([M + Na]⁺) | ¹H NMR (CDCl₃) δ 5.33 (d, J = 8.3 Hz, 1H), 5.05 (dq, J = 10.1, 6.3 Hz, 1H), 4.74-4.61 (m, 2H), 3.93 (dd, J = 11.9, 6.6 Hz, 1H), 3.69 (m, 3H), 2.54 (p, J = 7.0 Hz, 1H), 2.06 (ddt, J = 9.9, 6.0, 4.0 Hz, 1H), 1.46 (d, J = 5.8 Hz, 1H), 1.43 (s, 9H), 1.39 (d, J = 6.3 Hz, 3H), 1.37-1.26 (m, 1H), 1.25-1.19 (m, 4H), 1.16 (dd, J = 7.0, 2.0 Hz, 6H), 0.87 (t, J = 6.9 Hz, 3H) | ¹³C NMR (CDCl₃) δ 175.82, 171.25, 155.16, 80.04, 78.40, 74.45, 74.25, 73.28, 53.76, 48.15, 34.09, 28.27, 27.95, 26.78, 23.24, 19.84, 18.93, 13.84 |
| 28 | — | (Thin Film) 3377, 2938, 2878, 1770, 1745, 1508 | HRMS-ESI (m/z) [M + H]⁺ calcd for $C_{28}H_{34}FN_2O_8$, 545.2294; found, 545.2325 | ¹H NMR (CDCl₃) δ 8.55 (d, J = 7.8 Hz, 1H), 8.14 (d, J = 5.4 Hz, 1H), 7.02 (dd, J = 8.5, 5.6 Hz, 2H), 6.84-6.72 (m, 3H), 4.93 (dq, J = 9.6, 6.3 Hz, 1H), 4.82 (ddd, J = 8.0, 6.1, 3.7 Hz, 1H), 3.84 (dd, J = 11.4, 5.5 Hz, 1H), 3.80 (d, J = 11.2 Hz, 1H), 3.74-3.65 (m, 1H), 3.70 (s, 3H), 3.50 (dd, J = 11.4, 5.9 Hz, 1H), 3.17 (dd, J = 10.1, 7.0 Hz, 1H), 3.04 (dd, J = 10.1, 6.6 Hz, 1H), 2.92 (ddd, J = 9.5, 6.0, 1.4 Hz, 1H), 2.75 (dd, J = 14.7, 4.1 Hz, 1H), 2.53 (dd, J = 14.6, 5.9 Hz, 1H), 2.19 (s, 3H), 2.04-1.91 (m, 1H), 1.13 (d, J = 6.3 Hz, 3H), 0.88-0.78 (m, 1H), 0.37-0.26 (m, 2H), 0.10--0.10 (m, 2H) | — |
| 29 | — | — | ESIMS m/z 478 ([M + Na]⁺) | ¹H NMR (CDCl₃) δ 5.35 (d, J = 7.9 Hz, 1H), 5.07 (dq, J = 10.3, 6.3 Hz, 1H), 4.61 (ddd, J = 8.3, 6.0, 3.6 Hz, 1H), 3.91 (dd, J = 12.0, 6.1 Hz, 2H), 3.81 (dd, J = 12.0, 3.7 Hz, 1H), 3.66 (dt, J = 9.2, 5.8 Hz, 1H), 3.63-3.53 (m, 1H), | ¹³C NMR (CDCl₃) δ 171.08, 155.22, 127.16 (q, J = 276.1 Hz), 81.58, 80.04, 79.75, 75.54, 73.50, 67.49, 54.44, 50.05, 30.83 (q, J = 29.0 Hz), 28.28, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 3.29 (dt, J = 9.1, 6.2 Hz, 1H), 3.08-2.97 (m, 1H), 2.27-2.07 (m, 2H), 1.80 (qt, J = 8.0, 4.8 Hz, 3H), 1.60 (tq, J = 10.4, 3.7 Hz, 1H), 1.44 (s, 9H), 1.37 (d, J = 6.2 Hz, 3H), 1.35-1.21 (m, 4H), 1.22-1.10 (m, 1H), 0.89 (t, J = 7.1 Hz, 3H) | 28.12, 27.32, 23.33, 22.73 (q, J = 3.1 Hz), 19.85, 13.92 |
| 30 | — | — | HRMS-ESI (m/z) [M + H]$^+$ calcd for C$_{32}$H$_{36}$FN$_2$O$_9$, 611.2399; found, 611.2398 | $^1$H NMR (CDCl$_3$) δ 8.62 (d, J = 7.7 Hz, 1H), 8.29 (d, J = 5.3 Hz, 1H), 7.36-7.25 (m, 5H), 7.13 (dd, J = 8.5, 5.6 Hz, 2H), 6.98-6.88 (m, 3H), 5.79-5.65 (m, 2H), 5.17 (dq, J = 9.5, 6.3 Hz, 1H), 5.06 (ddd, J = 7.8, 6.0, 3.6 Hz, 1H), 4.65 (d, J = 11.5 Hz, 1H), 4.39 (d, J = 11.5 Hz, 1H), 4.13 (d, J = 10.3 Hz, 1H), 4.10 (dd, J = 11.0, 4.9 Hz, 1H), 3.97 (dd, J = 12.1, 3.6 Hz, 1H), 3.90 (s, 3H), 3.79 (dd, J = 11.6, 5.7 Hz, 1H), 3.27 (ddd, J = 9.7, 5.7, 1.4 Hz, 1H), 2.91 (dd, J = 14.7, 4.2 Hz, 1H), 2.75 (dd, J = 14.7, 6.0 Hz, 1H), 2.24 (tdd, J = 9.7, 6.0, 4.3 Hz, 1H), 2.06 (s, 3H), 1.34 (d, J = 6.3 Hz, 3H) | $^{19}$F NMR (CDCl$_3$) δ −117.21 |
| 31 | — | — | ESIMS m/z 340 ([M + H]$^+$) | — | — |
| 32 | 44-50 | — | HRMS-ESI (m/z) [M + H]$^+$ calcd for C$_{29}$H$_{39}$N$_2$O$_9$, 559.2650; found, 559.2673 | $^1$H NMR (CDCl$_3$) δ 8.67 (d, J = 7.8 Hz, 1H), 8.32 (d, J = 5.4 Hz, 1H), 7.32-7.23 (m, 2H), 7.00-6.86 (m, 4H), 5.75 (s, 2H), 5.25 (dq, J = 12.3, 6.3 Hz, 1H), 5.15-5.06 (m, 1H), 4.11-4.00 (m, 4H), 3.92 (s, 3H), 3.72 (dd, J = 11.3, 6.2 Hz, 1H), 2.20-2.05 (m, 4H), 1.85-1.73 (m, 1H), 1.48-1.33 (m, 5H), 1.30-1.15 (m, 1H), 1.10-0.97 (m, 1H), 0.82 (d, J = 6.6 Hz, 3H), 0.77 (d, J = 6.6 Hz, 3H) | — |
| 33 | — | — | ESIMS m/z 356 ([M + H]$^+$) | — | — |
| 34 | — | — | ESIMS m/z 316 ([M + H]$^+$) | $^1$H NMR (CDCl$_3$) δ 8.74 (bs, 3H), 5.19-5.10 (m, 1H), 4.66-4.58 (m, 2H), 4.43 (dd, J = 13.0, 3.3 Hz, 1H), 4.08 (dd, J = 13.1, 6.3 Hz, 1H), 3.85 (d, J = 11.2 Hz, 1H), 3.70-3.62 (m, 1H), 2.53 (p, J = 7.0 Hz, 1H), 2.07 (dq, J = 10.1, 5.8, 4.9 Hz, 1H), 1.45 (d, J = 5.2 Hz, 1H), 1.41 (d, J = 6.3 Hz, 3H), 1.38-1.18 (m, 5H), 1.15 (dd, J = 7.0, 0.9 Hz, 6H), 0.90-0.83 (m, 3H) | — |
| 35 | — | — | ESIMS m/z 328 ([M + H]$^+$) | — | — |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| 36 | 80-82 | — | HRMS-ESI (m/z) [M + H]$^+$ calcd for C$_{24}$H$_{35}$N$_2$O$_8$, 479.2388; found, 479.2385 | $^1$H NMR (CDCl$_3$) δ 11.95 (s, 1H), 8.69 (d, J = 8.3 Hz, 1H), 8.00 (d, J = 5.2 Hz, 1H), 6.88 (d, J = 5.2 Hz, 1H), 5.17-5.01 (m, 2H), 4.76 (ddd, J = 10.0, 5.6, 2.2 Hz, 1H), 4.08 (dd, J = 11.9, 6.7 Hz, 1H), 3.94 (s, 3H), 3.88-3.72 (m, 3H), 2.19-2.07 (m, 1H), 1.67-1.29 (m, 7H), 1.19-1.06 (m, 2H), 1.05-0.96 (m, 2H), 0.93-0.83 (m, 8H) | — |
| 37 | — | (Thin Film) 3377, 2936, 2871, 1731, 1641 | HRMS-ESI (m/z) [M + H]$^+$ calcd for C$_{26}$H$_{34}$N$_2$O$_7$, 487.2439; found, 487.2413 | $^1$H NMR (CDCl$_3$) δ 12.00 (d, J = 0.6 Hz, 1H), 8.75 (d, J = 8.1 Hz, 1H), 8.02 (d, J = 5.2 Hz, 1H), 7.41-7.23 (m, 5H), 6.87 (dd, J = 5.3, 0.6 Hz, 1H), 5.14 (dq, J = 10.3, 6.3 Hz, 1H), 5.04 (ddd, J = 8.0, 6.1, 3.8 Hz, 1H), 4.65 (d, J = 11.3 Hz, 1H), 4.39 (d, J = 11.3 Hz, 1H), 4.12 (dd, J = 11.5, 1.0 Hz, 1H), 4.06 (d, J = 6.2 Hz, 1H), 3.98 (d, J = 3.9 Hz, 1H), 3.94 (s, 3H), 3.72 (dd, J = 11.3, 6.1 Hz, 1H), 3.28 (ddd, J = 10.0, 6.1, 1.1 Hz, 1H), 2.01-1.86 (m, 1H), 1.77-1.64 (m, 1H), 1.40 (d, J = 6.3 Hz, 3H), 1.38-1.29 (m, 1H), 1.28-1.19 (m, 3H), 1.19-1.07 (m, 1H), 0.86 (t, J = 7.0 Hz, 3H) | — |
| 38 | — | — | HRMS-ESI (m/z) [M + H]$^+$ calcd for C$_{29}$H$_{32}$FN$_2$O$_7$, 539.2188; found, 539.2186 | $^1$H NMR (CDCl$_3$) δ 11.99 (d, J = 0.6 Hz, 1H), 8.75 (d, J = 8.0 Hz, 1H), 8.00 (d, J = 5.2 Hz, 1H), 7.37-7.26 (m, 5H), 7.13 (dd, J = 8.6, 5.5 Hz, 2H), 6.93 (t, J = 8.7 Hz, 2H), 6.86 (d, J = 5.5 Hz, 1H), 5.19 (dq, J = 9.3, 6.3 Hz, 1H), 5.03 (ddd, J = 8.0, 5.9, 3.4 Hz, 1H), 4.65 (d, J = 11.5 Hz, 1H), 4.40 (d, J = 11.5 Hz, 1H), 4.14 (d, J = 10.8 Hz, 1H), 4.11 (dd, J = 11.6, 5.4 Hz, 1H), 4.00 (dd, J = 12.1, 3.4 Hz, 1H), 3.92 (s, 3H), 3.79 (dd, J = 11.7, 5.6 Hz, 1H), 3.28 (ddd, J = 9.6, 5.5, 1.4 Hz, 1H), 2.91 (dd, J = 14.7, 4.3 Hz, 1H), 2.75 (dd, J = 14.6, 6.0 Hz, 1H), 2.24 (tdd, J = 9.4, 6.0, 4.3 Hz, 1H), 1.35 (d, J = 6.3 Hz, 3H) | $^{19}$F NMR (CDCl$_3$) δ −117.10 |
| 39 | 74-77 | — | ESIMS m/z 424 ([M + Na]$^+$) | $^1$H NMR (CDCl$_3$) δ 5.35 (d, J = 8.4 Hz, 1H), 5.11-4.99 (m, 1H), 4.66-4.57 (m, 1H), 3.98-3.86 (m, 2H), 3.83-3.74 (m, 1H), 3.61-3.50 (m, 2H), 3.26-3.16 (m, 1H), 3.06-2.97 (m, 1H), 1.87-1.74 (m, 1H), 1.75-1.61 (m, 1H), 1.62-1.39 (m, 12H), 1.41-1.27 (m, 4H), 1.23-1.07 (m, 2H), 0.95-0.85 (m, 9H) | — |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| 40 | — | (Thin Film) 3380, 2953, 2872, 1748, 1676 | HRMS-ESI (m/z) [M + H]⁺ calcd for $C_{29}H_{38}N_2O_9$, 559.2650; found, 559.2651 | ¹H NMR (CDCl₃) δ 8.62 (d, J = 7.8 Hz, 1H), 8.30 (d, J = 5.4 Hz, 1H), 7.39-7.27 (m, 5H), 6.96 (d, J = 5.4 Hz, 1H), 5.74 (d, J = 1.7 Hz, 2H), 5.18-5.02 (m, 2H), 4.65 (d, J = 11.3 Hz, 1H), 4.38 (d, J = 11.3 Hz, 1H), 4.14-4.01 (m, 2H), 3.97-3.92 (m, 1H), 3.91 (s, 3H), 3.72 (dd, J = 11.3, 6.2 Hz, 1H), 3.28 (ddd, J = 10.1, 6.3, 1.2 Hz, 1H), 2.07 (s, 3H), 1.91 (tt, J = 10.1, 3.9 Hz, 1H), 1.77-1.65 (m, 1H), 1.39 (d, J = 6.3 Hz, 3H), 1.37-1.30 (m, 1H), 1.30-1.18 (m, 3H), 1.17-1.05 (m, 1H), 0.85 (t, J = 7.0 Hz, 3H) | — |
| 41 | — | — | ESIMS m/z 388 ([M + H]⁺) | — | — |
| 42 | 70-72 | — | ESIMS m/z 472 ([M + Na]⁺) | ¹H NMR (CDCl₃) δ 7.38-7.24 (m, 5H), 5.35 (d, J = 8.2 Hz, 1H), 5.07 (dq, J = 12.3, 6.3 Hz, 1H), 4.68-4.59 (m, 2H), 4.36 (d, J = 11.2 Hz, 1H), 4.07 (d, J = 11.3 Hz, 1H), 3.95 (dd, J = 12.0, 6.2 Hz, 1H), 3.81 (dd, J = 11.9, 3.9 Hz, 1H), 3.66 (dd, J = 11.3, 6.2 Hz, 1H), 3.22 (dd, J = 9.9, 6.2 Hz, 1H), 1.95-1.83 (m, 1H), 1.77-1.63 (m, 1H), 1.48-1.27 (m, 14H), 1.19-0.99 (m, 2H), 0.83 (app dd, J = 7.6, 6.6 Hz, 6H) | — |
| 43 | — | (Thin Film) 3376, 2956, 2875, 1733, 1676 cm−1 | HRMS-ESI (m/z) [M + H]⁺ calcd for $C_{26}H_{38}N_2O_4$, 539.2599; found, 539.2604 | ¹H NMR (CDCl₃) δ 8.56 (d, J = 8.0 Hz, 1H), 8.29 (d, J = 5.3 Hz, 1H), 6.96 (d, J = 5.4 Hz, 1H), 5.73 (d, J = 0.8 Hz, 2H), 5.16-5.03 (m, 2H), 4.74 (ddd, J = 10.1, 5.8, 2.2 Hz, 1H), 4.06 (dd, J = 11.8, 6.8 Hz, 1H), 3.91 (s, 3H), 3.80 (dd, J = 11.9, 4.9 Hz, 1H), 3.78-3.70 (m, 2H), 2.55 (hept, J = 7.0 Hz, 1H), 2.16-2.08 (m, 1H), 2.07 (s, 3H), 1.55-1.44 (m, 1H), 1.41 (d, J = 6.3 Hz, 3H), 1.39-1.29 (m, 1H), 1.29-1.19 (m, 4H), 1.17 (dd, J = 7.0, 2.1 Hz, 6H), 0.87 (t, J = 6.9 Hz, 3H) | — |
| 44 | — | (Thin Film) 3378, 2954, 2873, 1748, 1676 | HRMS-ESI (m/z) [M + H]⁺ calcd for $C_{28}H_{36}N_2O_9$, 545.2494; found, 545.2503 | ¹H NMR (CDCl₃) δ 8.67 (d, J = 7.8 Hz, 1H), 8.32 (d, J = 5.3 Hz, 1H), 7.34-7.23 (m, 2H), 7.00-6.86 (m, 4H), 5.75 (d, J = 1.0 Hz, 2H), 5.24 (dq, J = 10.6, 6.3 Hz, 1H), 5.10 (ddd, J = 7.8, 5.4, 4.1 Hz, 1H), 4.10-4.01 (m, 4H), 3.92 (s, 3H), 3.73 (dd, J = 11.4, 6.3 Hz, 1H), 2.13 (tt, J = 10.3, 3.8 Hz, 1H), 2.07 (s, 3H), 1.76 (ddt, J = 13.8, 11.6, 4.1 Hz, 2H), 1.45 (d, J = 6.2 Hz, 3H), | — |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| 45 | — | (Thin Film) 3367, 2936, 2873, 1745, 1649 | HRMS-ESI (m/z) [M + H]⁺ calcd for C₂₅H₃₂N₂O₇, 473.2282; found, 473.2287 | 1.42-1.10 (m, 4H), 0.82 (t, J = 7.0 Hz, 3H) ¹H NMR (CDCl₃) δ 11.99 (d, J = 0.6 Hz, 1H), 8.81 (d, J = 8.0 Hz, 1H), 8.04 (d, J = 5.2 Hz, 1H), 7.34-7.25 (m, 2H), 6.95 (tt, J = 7.4, 1.0 Hz, 1H), 6.92-6.87 (m, 3H), 5.27 (dq, J = 10.4, 6.3 Hz, 1H), 5.08 (ddd, J = 8.0, 5.4, 3.9 Hz, 1H), 4.14-4.03 (m, 4H), 3.95 (s, 3H), 3.72 (dd, J = 11.3, 6.1 Hz, 1H), 2.20-2.08 (m, 1H), 1.76 (ddt, J = 13.7, 11.5, 4.2 Hz, 1H), 1.46 (d, J = 6.3 Hz, 3H), 1.43-1.11 (m, 5H), 0.83 (t, J = 7.1 Hz, 3H) | — |
| 46 | 104-106 | — | HRMS-ESI (m/z) [M + H]⁺ calcd for C₂₇H₃₇N₂O₇, 501.2595; found, 501.2616 | ¹H NMR (CDCl₃) δ 12.00 (s, 1H), 8.75 (d, J = 8.0 Hz, 1H), 8.02 (d, J = 5.2 Hz, 1H), 7.39-7.24 (m, 5H), 6.87 (d, J = 5.2 Hz, 1H), 5.14 (dq, J = 10.4, 6.3 Hz, 1H), 5.04 (ddd, J = 8.1, 6.2, 3.9 Hz, 1H), 4.65 (d, J = 11.2 Hz, 1H), 4.39 (d, J = 11.2 Hz, 1H), 4.16-4.03 (m, 2H), 4.01-3.92 (m, 4H), 3.72 (dd, J = 11.3, 6.1 Hz, 1H), 3.33-3.24 (m, 1H), 2.00-1.88 (m, 1H), 1.80-1.66 (m, 1H), 1.49-1.29 (m, 5H), 1.21-1.01 (m, 2H), 0.84 (app dd, J = 7.3, 6.6 Hz, 6H) | — |
| 47 | 66-70 | — | HRMS-ESI (m/z) [M + H]⁺ calcd for C₂₈H₃₇N₂O₈, 529.2544; found, 529.2558 | ¹H NMR (CDCl₃) δ 8.84 (d, J = 8.4 Hz, 1H), 8.38 (d, J = 5.4 Hz, 1H), 7.33-7.24 (m, 2H), 7.02 (d, J = 5.5 Hz, 1H), 6.98-6.91 (m, 1H), 6.91-6.85 (m, 2H), 5.24 (dq, J = 10.4, 6.2 Hz, 1H), 5.07 (ddd, J = 8.0, 5.4, 4.1 Hz, 1H), 4.10-3.96 (m, 4H), 3.91 (s, 3H), 3.71 (dd, J = 11.3, 6.3 Hz, 1H), 2.39 (s, 3H), 2.19-2.07 (m, 1H), 1.86-1.71 (m, 1H), 1.47-1.32 (m, 5H), 1.29-1.15 (m, 1H), 1.10-0.97 (m, 1H), 0.81 (d, J = 6.6 Hz, 3H), 0.77 (d, J = 6.6 Hz, 3H) | — |
| 48 | — | (Thin Film) 3380, 2955, 2875, 1749, 1676 | HRMS-ESI (m/z) [M + H]⁺ calcd for C₂₆H₃₇F₃N₂O₉, 579.2524; found, 579.2528 | ¹H NMR (CDCl₃) δ 8.60 (d, J = 7.8 Hz, 1H), 8.29 (d, J = 5.3 Hz, 1H), 6.96 (d, J = 5.4 Hz, 1H), 5.79-5.68 (m, 2H), 5.12 (dq, J = 10.4, 6.3 Hz, 1H), 5.04 (ddd, J = 7.8, 6.1, 3.8 Hz, 1H), 4.03 (dd, J = 12.1, 6.1 Hz, 1H), 3.98-3.92 (m, 2H), 3.91 (s, 3H), 3.66 (ddt, J = 14.5, 11.3, 5.9 Hz, 2H), 3.31 (dt, J = 9.3, 6.2 Hz, 1H), 3.09 (ddd, J = 10.0, 6.0, 1.1 Hz, 1H), 2.26-2.10 (m, 2H), 2.07 (s, 3H), 1.91-1.74 (m, 3H), 1.61 (ddt, J = 11.1, 8.3, 3.5 Hz, 1H), | — |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| 49 | 92-95 | — | ESIMS m/z 450 ([M + Na]⁺) | 1.39 (d, J = 6.2 Hz, 3H), 1.37-1.13 (m, 5H), 0.90 (t, J = 6.9 Hz, 3H) ¹H NMR (CDCl₃) δ 5.31 (d, J = 8.2 Hz, 1H), 5.09-4.97 (m, 1H), 4.75-4.60 (m, 2H), 3.99-3.89 (m, 1H), 3.78-3.63 (m, 3H), 2.13-2.01 (m, 1H), 1.65-1.54 (m, 1H), 1.53-1.26 (m, 15H), 1.19-1.04 (m, 2H), 1.05-0.93 (m, 2H), 0.90-0.82 (m, 8H) | — |
| 50 | — | — | ESIMS m/z 388 ([M + H]⁺) | — | — |
| 51 | — | — | ESIMS m/z 458 ([M + Na]⁺) | ¹H NMR (CDCl₃) δ 7.31-7.22 (m, 2H), 6.98-6.90 (m, 1H), 6.90-6.83 (m, 2H), 5.42 (d, J = 7.9 Hz, 1H), 5.19 (dq, J = 10.4, 6.2 Hz, 1H), 4.72-4.63 (m, 1H), 4.07-3.95 (m, 2H), 3.90 (d, J = 4.9 Hz, 2H), 3.66 (dd, J = 11.3, 6.2 Hz, 1H), 2.16-2.04 (m, 1H), 1.82-1.69 (m, 1H), 1.49-1.32 (m, 14H), 1.29-1.16 (m, 1H), 1.10-0.97 (m, 1H), 0.81 (d, J = 6.6 Hz, 3H), 0.77 (d, J = 6.6 Hz, 3H) | ¹³C NMR (CDCl₃) δ 170.91, 157.22, 155.27, 129.62, 120.88, 115.09, 80.26, 80.09, 78.29, 75.90, 73.25, 54.71, 50.29, 33.75, 28.50, 28.33, 25.98, 22.48, 22.32, 19.88 |
| 52 | — | — | ESIMS m/z 336 ([M + H]⁺) | ¹H NMR (CDCl₃) δ 8.85 (bs, 3H), 7.35-7.27 (m, 5H), 5.20-5.08 (m, 1H), 4.61 (d, J = 11.3 Hz, 1H), 4.55 (dd, J = 5.8, 2.9 Hz, 1H), 4.45 (dd, J = 13.1, 2.9 Hz, 1H), 4.36 (d, J = 11.4 Hz, 1H), 4.15 (d, J = 11.5 Hz, 1H), 4.05 (dd, J = 13.1, 5.8 Hz, 1H), 3.61 (dd, J = 11.7, 5.8 Hz, 1H), 3.25 (dd, J = 9.9, 5.5 Hz, 1H), 1.92-1.82 (m, 1H), 1.64 (t, J = 12.8 Hz, 1H), 1.37 (d, J = 6.3 Hz, 3H), 1.34-1.15 (m, 4H), 1.15-1.04 (m, 1H), 0.83 (t, J = 6.9 Hz, 3H) | — |
| 53 | 54-57 | — | HRMS-ESI (m/z) [M + H]⁺ calcd for C₂₃H₃₇N₂O₇, 453.2595; found, 453.2608 | ¹H NMR (CDCl₃) δ 11.99 (s, 1H), 8.73 (d, J = 8.1 Hz, 1H), 7.99 (d, J = 5.2 Hz, 1H), 6.87 (d, J = 5.3 Hz, 1H), 5.19-5.07 (m, 1H), 5.07-4.97 (m, 1H), 4.09-3.91 (m, 6H), 3.68-3.52 (m, 2H), 3.29-3.19 (m, 1H), 3.08 (dd, J = 9.8, 6.0 Hz, 1H), 1.91-1.80 (m, 1H), 1.77-1.64 (m, 1H), 1.63-1.30 (m, 7H), 1.28-1.10 (m, 2H), 0.97-0.86 (m, 9H) | — |
| 54 | — | — | ESIMS m/z 452 ([M + H]⁺) | ¹H NMR (CDCl₃) δ 7.19 (dd, J = 8.4, 5.6 Hz, 2H), 6.97 (t, J = 8.7 Hz, 2H), 5.35-5.29 (m, 1H), 5.08 (dt, J = 12.4, 6.2 Hz, 1H), 4.65-4.56 (m, 1H), 4.00-3.89 (m, 2H), 3.85-3.76 (m, 1H), 3.64 (dd, J = 11.5, 5.8 Hz, 1H), 3.34 (dd, J = 10.1, 7.1 Hz, 1H), 3.21 (dd, J = 10.1, 6.6 Hz, | ¹⁹F NMR (CDCl₃) δ −117.31 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 1H), 3.04 (dd, J = 9.4, 5.9 Hz, 1H), 2.93 (dd, J = 14.7, 4.2 Hz, 1H), 2.70 (dd, J = 14.6, 6.0 Hz, 1H), 2.13 (tt, J = 9.7, 5.3 Hz, 1H), 1.43 (s, 9H), 1.30 (d, J = 6.3 Hz, 3H), 1.09-0.95 (m, 1H), 0.58-0.46 (m, 2H), 0.25-0.11 (m, 2H) | |
| 55 | — | — | ESIMS m/z 422 ([M + Na]⁺) | ¹H NMR (CDCl₃) δ 5.37 (d, J = 7.9 Hz, 1H), 5.05 (dq, J = 10.3, 6.3 Hz, 1H), 4.62 (ddd, J = 8.0, 6.2, 3.9 Hz, 1H), 3.98-3.86 (m, 2H), 3.82-3.75 (m, 1H), 3.58 (dd, J = 11.2, 6.3 Hz, 1H), 3.41 (dd, J = 10.0, 6.9 Hz, 1H), 3.14 (dd, J = 10.0, 6.8 Hz, 1H), 3.05 (dd, J = 9.9, 6.2 Hz, 1H), 1.84 (tt, J = 10.1, 3.8 Hz, 1H), 1.70 (m, 1H), 1.44 (s, 9H), 1.37 (d, J = 6.3 Hz, 3H), 1.33-1.16 (m, 5H), 1.01 (m, 1H), 0.89 (t, J = 7.0 Hz, 3H), 0.58-0.45 (m, 2H), 0.24-0.12 (m, 2H) | ¹³C NMR (CDCl₃) δ 171.17, 155.20, 80.60, 79.96, 79.73, 75.21, 74.35, 73.59, 54.32, 50.00, 28.27, 27.97, 26.96, 23.39, 19.89, 13.97, 10.68, 2.97 |
| 56 | — | — | ESIMS m/z 510 ([M + Na]⁺) | ¹H NMR (CDCl₃) δ 7.12-7.04 (m, 4H), 6.91 (t, J = 8.7 Hz, 2H), 6.71 (d, J = 8.5 Hz, 2H), 5.37 (d, J = 7.9 Hz, 1H), 5.17 (dq, J = 10.0, 6.3 Hz, 1H), 4.70-4.62 (m, 1H), 4.01 (d, J = 11.3 Hz, 1H), 3.97-3.80 (m, 3H), 3.68 (dd, J = 11.4, 6.1 Hz, 1H), 2.93 (dd, J = 14.7, 5.0 Hz, 1H), 2.83 (dd, J = 14.7, 4.4 Hz, 1H), 2.37 (tt, J = 9.8, 4.7 Hz, 1H), 2.29 (s, 3H), 1.46 (d, J = 6.3 Hz, 3H), 1.44 (s, 9H) | ¹⁹F NMR (CDCl₃) δ −116.99 |
| 57 | 45-50 | — | HRMS-ESI (m/z) [M + H]⁺ calcd for C₂₇H₃₉N₂O₁₀, 551.2599; found, 551.2610 | ¹H NMR (CDCl₃) δ 8.55 (d, J = 8.1 Hz, 1H), 8.29 (d, J = 5.3 Hz, 1H), 6.96 (d, J = 5.4 Hz, 1H), 5.77-5.69 (m, 2H), 5.13-5.03 (m, 1H), 4.80-4.71 (m, 1H), 4.07 (dd, J = 11.8, 6.8 Hz, 1H), 3.91 (s, 3H), 3.84-3.74 (m, 3H), 2.07 (s, 4H), 1.67-1.28 (m, 7H), 1.19-1.06 (m, 2H), 1.04-0.96 (m, 2H), 0.91-0.82 (m, 8H) | — |
| 58 | — | (Thin Film) 3376, 2963, 2873, 1728, 1641 | ESIMS m/z 467 ([M + H]⁺) | ¹H NMR (CDCl₃) δ 11.95 (d, J = 0.6 Hz, 1H), 8.70 (d, J = 8.3 Hz, 1H), 8.00 (d, J = 5.2 Hz, 1H), 6.88 (d, J = 5.2 Hz, 1H), 5.16-5.02 (m, 2H), 4.74 (ddd, J = 10.1, 4.7, 3.1 Hz, 1H), 4.09-4.03 (m, 1H), 3.94 (s, 3H), 3.84 (dd, J = 11.9, 4.8 Hz, 1H), 3.79-3.75 (m, 2H), 2.56 (p, J = 7.0 Hz, 1H), 2.19-2.06 (m, 1H), 1.58-1.45 (m, 1H), 1.42 (d, J = 6.3 Hz, 3H), | — |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 1.40-1.29 (m, 1H), 1.30-1.19 (m, 4H), 1.18 (dd, J = 7.0, 2.1 Hz, 6H), 0.88 (t, J = 6.9 Hz, 3H) | |
| 59 | — | — | HRMS-ESI (m/z) [M + H]$^+$ calcd for C$_{29}$H$_{34}$FN$_2$O$_{10}$, 589.2192; found, 589.2189 | $^1$H NMR (CDCl$_3$) δ 8.57 (d, J = 7.9 Hz, 1H), 8.29 (d, J = 5.3 Hz, 1H), 7.17 (dd, J = 8.5, 5.5 Hz, 2H), 7.02-6.93 (m, 3H), 5.83-5.65 (m, 2H), 5.19-5.03 (m, 2H), 4.77 (ddd, J = 9.3, 5.1, 2.2 Hz, 1H), 4.14 (dd, J = 11.6, 6.5 Hz, 1H), 3.91 (s, 3H), 3.88-3.75 (m, 3H), 2.79 (dd, J = 14.8, 6.3 Hz, 1H), 2.67 (dd, J = 14.8, 5.5 Hz, 1H), 2.55-2.42 (m, 1H), 2.06 (s, 3H), 1.50 (tt, J = 8.0, 4.6 Hz, 1H), 1.39 (d, J = 6.4 Hz, 3H), 1.00-0.92 (m, 2H), 0.92-0.78 (m, 2H) | $^{19}$F NMR (CDCl$_3$) δ −116.84 |
| 60 | 58-62 | — | HRMS-ESI (m/z) [M + H]$^+$ calcd for C$_{26}$H$_{35}$N$_2$O$_7$, 487.2439; found, 487.2469 | $^1$H NMR (CDCl$_3$) δ 11.98 (s, 1H), 8.80 (d, J = 8.0 Hz, 1H), 8.04 (d, J = 5.2 Hz, 1H), 7.33-7.23 (m, 2H), 6.99-6.85 (m, 4H), 5.27 (dq, J = 10.4, 6.3 Hz, 1H), 5.07 (ddd, J = 8.0, 5.4, 3.8 Hz, 1H), 4.15-3.99 (m, 4H), 3.95 (s, 3H), 3.72 (dd, J = 11.4, 6.2 Hz, 1H), 2.21-2.09 (m, 1H), 1.86-1.72 (m, 1H), 1.49-1.34 (m, 5H), 1.31-1.17 (m, 1H), 1.12-0.99 (m, 1H), 0.82 (d, J = 6.6 Hz, 3H), 0.78 (d, J = 6.6 Hz, 3H) | — |
| 61 | — | — | ESIMS m/z 322 ([M + H]$^+$) | $^1$H NMR (CDCl$_3$) δ 7.32-7.23 (m, 2H), 6.94 (td, J = 7.4, 1.1 Hz, 1H), 6.91-6.86 (m, 2H), 5.08 (dq, J = 10.5, 6.3 Hz, 1H), 4.02 (ddd, J = 9.9, 6.5, 1.1 Hz, 1H), 3.97-3.86 (m, 2H), 3.83 (dd, J = 6.7, 4.6 Hz, 1H), 3.72 (dd, J = 10.9, 6.6 Hz, 1H), 3.63 (dd, J = 11.5, 4.6 Hz, 1H), 2.09 (tt, J = 10.2, 3.9 Hz, 1H), 1.77-1.66 (m, 2H), 1.42 (d, J = 6.3 Hz, 3H), 1.34-1.01 (m, 4H), 0.93-0.77 (m, 5H) | — |
| 62 | — | — | HRMS-ESI (m/z) [M + H]$^+$ calcd for C$_{28}$H$_{36}$FN$_2$O$_9$, 563.2399; found, 563.2414 | $^1$H NMR (CDCl$_3$) δ 8.59 (d, J = 7.8 Hz, 1H), 8.28 (d, J = 5.3 Hz, 1H), 7.22-7.13 (m, 2H), 7.02-6.90 (m, 3H), 5.77-5.67 (m, 2H), 5.12 (dq, J = 9.6, 6.3 Hz, 1H), 5.04 (ddd, J = 7.8, 6.1, 3.7 Hz, 1H), 4.07 (dd, J = 12.1, 6.1 Hz, 1H), 4.01 (d, J = 11.2 Hz, 1H), 3.92 (dd, J = 12.1, 3.8 Hz, 1H), 3.91 (s, 3H), 3.71 (dd, J = 11.5, 5.8 Hz, 1H), 3.55 (dt, J = 9.0, 6.6 Hz, 1H), 3.25 (dt, J = 8.9, 6.6 Hz, 1H), 3.08 (dd, J = 9.6, 5.8 Hz, 1H), 2.92 (dd, J = 14.7, 4.1 Hz, 1H), 2.71 (dd, J = 14.7, 6.0 Hz, 1H), | $^{19}$F NMR (CDCl$_3$) δ −117.38 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 2.22-2.09 (m, 1H), 2.06 (s, 3H), 1.64-1.51 (m, 2H), 1.32 (d, $J$ = 6.3 Hz, 3H), 0.91 (t, $J$ = 7.4 Hz, 3H) | |
| 63 | — | — | ESIMS m/z 336 ([M + H]⁺) | — | — |
| 64 | — | — | HRMS-ESI (m/z) [M + H]⁺ calcd for $C_{32}H_{36}FN_2O_9$, 611.2399; found, 611.2400 | ¹H NMR (CDCl₃) δ 8.62 (d, $J$ = 7.7 Hz, 1H), 8.30 (d, $J$ = 5.4 Hz, 1H), 7.14-7.04 (m, 4H), 6.96 (d, $J$ = 5.4 Hz, 1H), 6.91 (t, $J$ = 8.7 Hz, 2H), 6.74 (d, $J$ = 8.6 Hz, 2H), 5.79-5.64 (m, 2H), 5.21 (dq, $J$ = 10.0, 6.2 Hz, 1H), 5.09 (ddd, $J$ = 7.8, 5.9, 3.6 Hz, 1H), 4.08-3.93 (m, 4H), 3.91 (s, 3H), 3.75 (dd, $J$ = 11.3, 6.2 Hz, 1H), 2.96 (dd, $J$ = 14.7, 4.9 Hz, 1H), 2.84 (dd, $J$ = 14.7, 4.3 Hz, 1H), 2.41 (tt, $J$ = 9.8, 4.6 Hz, 1H), 2.28 (s, 3H), 2.06 (s, 3H), 1.49 (d, $J$ = 6.3 Hz, 3H) | ¹⁹F NMR (CDCl₃) δ −116.97 |
| 65 | — | (Thin Film) 3359, 2956, 2873, 1746, 1644 | HRMS-ESI (m/z) [M + H]⁺ calcd for $C_{23}H_{33}F_3N_2O_7$, 507.2313; found, 507.2320 | ¹H NMR (CDCl₃) δ 11.98 (s, 1H), 8.74 (d, $J$ = 8.1 Hz, 1H), 8.01 (d, $J$ = 5.2 Hz, 1H), 6.88 (d, $J$ = 5.2 Hz, 1H), 5.14 (dq, $J$ = 10.3, 6.3 Hz, 1H), 5.02 (ddd, $J$ = 8.0, 6.0, 3.7 Hz, 1H), 4.04 (dd, $J$ = 12.1, 6.0 Hz, 1H), 3.97 (d, $J$ = 3.8 Hz, 1H), 3.96-3.93 (m, 4H), 3.67 (ddt, $J$ = 13.8, 11.4, 5.6 Hz, 2H), 3.32 (dt, $J$ = 9.2, 6.2 Hz, 1H), 3.10 (ddd, $J$ = 10.0, 5.8, 1.1 Hz, 1H), 2.26-2.10 (m, 2H), 1.93-1.76 (m, 3H), 1.63 (ddt, $J$ = 15.0, 11.1, 4.3 Hz, 1H), 1.40 (d, $J$ = 6.3 Hz, 3H), 1.38-1.23 (m, 5H), 0.91 (t, $J$ = 7.0 Hz, 3H) | — |
| 66 | 112-115 | — | ESIMS m/z 382 ([M + Na]⁺) | ¹H NMR (CDCl₃) δ 5.41 (d, $J$ = 8.2 Hz, 1H), 4.95 (dq, $J$ = 9.7, 6.3 Hz, 1H), 4.74-4.46 (m, 1H), 4.00 (dd, $J$ = 11.8, 6.8 Hz, 1H), 3.80-3.70 (m, 2H), 3.62-3.50 (m, 2H), 2.28-2.14 (m, 1H), 1.88-1.76 (m, 1H), 1.69-1.57 (m, 1H), 1.53-1.37 (m, 14H), 1.30-1.07 (m, 2H), 0.88 (app d, $J$ = 6.6 Hz, 6H) | — |
| 67 | 55-61 | — | HRMS-ESI (m/z) [M + H]⁺ calcd for $C_{29}H_{39}N_2O_8$, 543.2701; found, 543.2702 | ¹H NMR (CDCl₃) δ 8.78 (d, $J$ = 8.2 Hz, 1H), 8.35 (d, $J$ = 5.4 Hz, 1H), 7.38-7.24 (m, 5H), 7.01 (d, $J$ = 5.4 Hz, 1H), 5.17-5.00 (m, 2H), 4.65 (d, $J$ = 11.2 Hz, 1H), 4.38 (d, $J$ = 11.2 Hz, 1H), 4.14-3.99 (m, 2H), 3.94-3.85 (m, 4H), 3.71 (dd, $J$ = 11.2, 6.3 Hz, 1H), 3.33-3.23 (m, 1H), 2.39 (s, 3H), 1.98-1.85 (m, 1H), 1.80-1.66 (m, 1H), 1.47-1.28 (m, 5H), | — |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| 68 | 70-75 | — | HRMS-ESI (m/z) [M + H]$^+$ calcd for C$_{26}$H$_{37}$N$_2$O$_9$, 521.2494; found, 521.2495 | 1.20-1.00 (m, 2H), 0.88-0.80 (m, 6H) $^1$H NMR (CDCl$_3$) δ 8.72 (d, J = 8.4 Hz, 1H), 8.34 (d, J = 5.3 Hz, 1H), 7.01 (d, J = 5.5 Hz, 1H), 5.13-5.00 (m, 2H), 4.75 (ddd, J = 10.1, 5.2, 2.7 Hz, 1H), 4.04 (dd, J = 11.8, 6.8 Hz, 1H), 3.90 (s, 3H), 3.81-3.72 (m, 3H), 2.38 (s, 3H), 2.16-2.04 (m, 1H), 1.66-1.28 (m, 7H), 1.18-1.06 (m, 2H), 1.04-0.95 (m, 2H), 0.91-0.82 (m, 8H) | — |
| 69 | — | — | ESIMS m/z 350 ([M + H]$^+$) | — | — |
| 70 | — | — | ESIMS m/z 522 ([M + Na]$^+$) | $^1$H NMR (CDCl$_3$) δ 7.39-7.14 (m, 10H), 5.33 (d, J = 8.1 Hz, 1H), 5.15-5.03 (m, 1H), 4.83 (d, J = 7.0 Hz, 1H), 4.70 (d, J = 7.0 Hz, 1H), 4.66-4.63 (m, 1H), 4.60 (d, J = 4.3 Hz, 2H), 4.05 (dd, J = 11.7, 6.3 Hz, 1H), 3.92-3.86 (m, 1H), 3.80 (dd, J = 11.6, 5.4 Hz, 1H), 3.68 (dd, J = 11.7, 4.6 Hz, 1H), 3.55 (ddd, J = 8.9, 5.4, 2.0 Hz, 1H), 2.98 (dd, J = 14.7, 4.5 Hz, 1H), 2.64 (dd, J = 14.7, 7.2 Hz, 1H), 2.40-2.26 (m, 1H), 1.44 (s, 9H), 1.28 (d, J = 6.4 Hz, 3H) | $^{13}$C NMR (CDCl$_3$) δ 171.40, 155.17, 140.35, 137.58, 129.00, 128.47, 128.45, 127.77, 127.76, 126.14, 94.13, 80.50, 80.05, 77.06, 74.11, 74.10, 70.20, 53.95, 51.15, 36.11, 28.32, 21.10 |
| 71 | — | (Thin Film) 3377, 2934, 1748, 1676, 1508 | HRMS-ESI (m/z) [M + H]$^+$ calcd for C$_{29}$H$_{36}$FN$_2$O$_9$, 575.2399; found, 575.2453 | $^1$H NMR (CDCl$_3$) δ 8.57 (d, J = 7.8 Hz, 1H), 8.28 (d, J = 5.3 Hz, 1H), 7.27-7.12 (m, 2H), 7.02-6.90 (m, 3H), 5.77-5.67 (m, 2H), 5.13 (dq, J = 9.6, 6.3 Hz, 1H), 5.04 (ddd, J = 7.8, 6.1, 3.7 Hz, 1H), 4.05 (dd, J = 12.1, 6.1 Hz, 1H), 4.00 (d, J = 11.0 Hz, 1H), 3.95-3.90 (m, 1H), 3.90 (s, 3H), 3.71 (dd, J = 11.5, 5.9 Hz, 1H), 3.36 (dd, J = 10.1, 7.0 Hz, 1H), 3.23 (dd, J = 10.2, 6.5 Hz, 1H), 3.11 (ddd, J = 9.7, 5.9, 1.4 Hz, 1H), 2.95 (dd, J = 14.7, 4.2 Hz, 1H), 2.72 (dd, J = 14.7, 6.0 Hz, 1H), 2.22-2.11 (m, 1H), 2.05 (s, 3H), 1.33 (d, J = 6.3 Hz, 3H), 1.09-0.95 (m, 1H), 0.58-0.47 (m, 2H), 0.27-0.12 (m, 2H) | — |
| 72 | — | (Thin Film) 3369, 3028, 2938, 1744, 1649, 1577, 1528, 1453 | HRMS-ESI (m/z) [M + H]$^+$ calcd for C$_{30}$H$_{35}$N$_2$O$_8$, 551.2388; found, 551.2388 | $^1$H NMR (CDCl$_3$) δ 11.98 (d, J = 0.7 Hz, 1H), 8.71 (d, J = 8.1 Hz, 1H), 8.00 (d, J = 5.2 Hz, 1H), 7.38-7.21 (m, 9H), 7.23-7.17 (m, 1H), 6.86 (d, J = 5.2 Hz, 1H), 5.17 (dq, J = 8.3, 6.4 Hz, 1H), 5.04 (ddd, J = 8.1, 6.4, 4.6 Hz, 1H), 4.85 (d, J = 7.0 Hz, 1H), 4.73 (d, J = 7.0 Hz, 1H), 4.65 (d, J = 11.9 Hz, 1H), 4.60 (d, J = 11.8 Hz, 1H), | — |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 4.19 (dd, J = 11.7, 6.4 Hz, 1H), 3.98-3.94 (m, 1H), 3.93 (s, 3H), 3.87 (dd, J = 11.8, 5.5 Hz, 1H), 3.83 (dd, J = 11.7, 4.7 Hz, 1H), 3.62 (ddd, J = 8.8, 5.4, 2.0 Hz, 1H), 3.00 (dd, J = 14.7, 4.5 Hz, 1H), 2.69 (dd, J = 14.7, 7.2 Hz, 1H), 2.36 (tdd, J = 8.5, 7.2, 4.5 Hz, 1H), 1.31 (d, J = 6.4 Hz, 3H) | |
| 73 | — | — | HRMS-ESI (m/z) [M + H]⁺ calcd for C₃₂H₃₆N₂O₉, 592.2421; found, 592.2426 | ¹H NMR (CDCl₃) δ 8.78 (d, J = 7.5 Hz, 1H), 8.36 (d, J = 5.4 Hz, 1H), 7.34-7.09 (m, 7H), 7.01 (d, J = 5.5 Hz, 1H), 6.96 (t, J = 7.3 Hz, 1H), 6.85 (d, J = 7.9 Hz, 2H), 5.31-5.18 (m, 1H), 5.12-4.95 (m, 1H), 4.10-3.91 (m, 4H), 3.89 (s, 3H), 3.80 (t, J = 6.6 Hz, 2H), 3.40 (s, 3H), 2.97 (t, J = 6.6 Hz, 2H), 2.92 (t, J = 4.8 Hz, 2H), 2.46 (tt, J = 9.7, 4.7 Hz, 1H), 1.47 (d, J = 6.3 Hz, 3H) | ¹³C NMR (CDCl₃) δ 170.11, 169.38, 162.77, 159.45, 156.58, 146.88, 141.24, 139.10, 129.68, 129.40, 128.38, 126.23, 121.00, 115.28, 109.93, 78.95, 78.18, 77.25, 74.99, 73.21, 67.57, 58.79, 56.34, 53.08, 51.57, 35.06, 34.60, 20.64 |
| 74 | — | — | ESIMS m/z 433.3 ([M + H]⁺) | ¹H NMR (CDCl₃) δ 7.32-7.14 (m, 5H), 5.35 (d, J = 7.7 Hz, 1H), 5.15-5.05 (m, 1H), 4.65-4.56 (m, 1H), 4.00-3.88 (m, 2H), 3.84-3.78 (m, 1H), 3.66 (dd, J = 11.5, 5.8 Hz, 1H), 3.34 (dd, J = 10.1, 7.1 Hz, 1H), 3.22 (dd, J = 10.0, 6.6 Hz, 1H), 3.11-2.94 (m, 2H), 2.72 (dd, J = 14.6, 6.2 Hz, 1H), 2.23-2.15 (m, 1H), 1.43 (s, 9H), 1.29 (d, J = 6.3 Hz, 3H), 1.08-0.99 (m, 1H), 0.57-0.46 (m, 2H), 0.24-0.12 (m, 2H) | ¹³C NMR (CDCl₃) δ 170.95, 155.21, 140.24, 129.24, 128.34, 126.03, 81.45, 79.99, 79.27, 75.26, 73.97, 54.42, 51.80, 35.53, 31.59, 28.29, 20.77, 10.70, 3.17 |
| 75 | — | — | ESIMS m/z 355.3 ([M − Cl]⁺) | — | — |
| 76 | — | — | HRMS-ESI (m/z) [M + H]⁺ calcd for C₂₆H₃₄N₂O₇, 486.2366; found, 486.2374 | ¹H NMR (CDCl₃) δ 11.99 (s, 1H), 8.73 (d, J = 8.0 Hz, 1H), 8.01 (d, J = 5.2 Hz, 1H), 7.44-7.08 (m, 5H), 6.87 (d, J = 5.2 Hz, 1H), 5.16 (dq, J = 9.5, 6.3 Hz, 1H), 5.04-4.97 (m, 1H), 4.17-3.95 (m, 3H), 3.94 (s, 3H), 3.72 (dd, J = 11.6, 5.6 Hz, 1H), 3.37 (dd, J = 8.8, 6.5 Hz, 1H), 3.16-3.07 (m, 2H), 3.03 (dd, J = 14.6, 3.9 Hz, 1H), 2.71 (dd, J = 14.6, 6.5 Hz, 1H), 2.25-2.15 (m, 1H), 1.84 (dp, J = 13.2, 6.6 Hz, 1H), 1.29 (d, J = 6.4 Hz, 3H), 0.90 (t, J = 6.8 Hz, 6H) | ¹³C NMR (CDCl₃) δ 169.90, 168.96, 155.32, 148.73, 140.63, 140.30, 130.32, 129.18, 128.37, 126.04, 109.53, 81.79, 79.11, 76.13, 74.59, 74.38, 56.08, 53.04, 51.86, 35.45, 28.85, 20.82, 19.54 |
| 77 | 49-54 | — | HRMS-ESI (m/z) [M + H]⁺ calcd for C₂₈H₃₀N₂O₇, 506.2053; found, 506.2062 | ¹H NMR (CDCl₃) δ 11.97 (s, 1H), 8.77 (d, J = 8.0 Hz, 1H), 8.03 (d, J = 5.2 Hz, 1H), 7.38-7.09 (m, 7H), 6.96 (t, J = 7.4 Hz, 1H), 6.87 (dd, J = 11.2, 6.5 Hz, 3H), 5.35-5.20 (m, 1H), 5.07 (dt, J = 9.0, | — |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 4.6 Hz, 1H), 4.14-4.01 (m, 4H), 3.95 (s, 3H), 3.78 (dd, J = 11.4, 6.1 Hz, 1H), 3.03-2.85 (m, 2H), 2.48 (tt, J = 9.8, 4.8 Hz, 1H), 1.49 (d, J = 6.3 Hz, 3H) | |
| 78 | — | — | ESIMS m/z 335.2 ([M − Cl]⁺) | — | — |
| 79 | 52-57 | — | HRMS-ESI (m/z) [M + H]⁺ calcd for C$_{28}$H$_{36}$N$_2$O$_8$, 528.2472; found, 528.2475 | ¹H NMR (CDCl$_3$) δ 8.76 (d, J = 7.3 Hz, 1H), 8.34 (d, J = 5.4 Hz, 1H), 7.33-7.13 (m, 5H), 7.00 (d, J = 5.5 Hz, 1H), 5.20-5.06 (m, 1H), 5.06-4.89 (m, 1H), 4.08-3.86 (m, 3H), 3.89 (s, 3H), 3.70 (dd, J = 11.4, 5.8 Hz, 1H), 3.37 (dd, J = 8.8, 6.5 Hz, 1H), 3.14-3.06 (m, 2H), 3.02 (dd, J = 14.6, 3.8 Hz, 1H), 2.69 (dd, J = 14.6, 6.4 Hz, 1H), 2.38 (s, 3H), 2.28-2.11 (m, 1H), 1.84 (dq, J = 13.3, 6.7 Hz, 1H), 1.27 (d, J = 6.4 Hz, 3H), 0.90 (t, J = 6.8 Hz, 6H) | — |
| 80 | — | — | HRMS-ESI (m/z) [M + H]⁺ calcd for C$_{29}$H$_{36}$N$_2$O$_9$, 556.2421; found, 556.2424 | ¹H NMR (CDCl$_3$) δ 8.59 (d, J = 7.4 Hz, 1H), 8.28 (d, J = 5.5 Hz, 1H), 7.37-7.14 (m, 5H), 6.95 (d, J = 5.0 Hz, 1H), 5.77-5.67 (m, 2H), 5.20-5.07 (m, 1H), 5.06-5.02 (m, 1H), 4.10-3.92 (m, 3H), 3.90 (s, 3H), 3.72 (dd, J = 11.4, 6.0 Hz, 1H), 3.35 (dd, J = 10.1, 7.1 Hz, 1H), 3.24 (dd, J = 10.1, 6.6 Hz, 1H), 3.12 (dd, J = 9.7, 5.0 Hz, 1H), 3.01 (dd, J = 14.6, 4.1 Hz, 1H), 2.75 (dd, J = 14.6, 6.2 Hz, 1H), 2.26-2.17 (m, 1H), 2.06 (s, 3H), 1.32 (d, J = 6.3 Hz, 3H), 1.10-0.96 (m, 1H), 0.57-0.46 (m, 2H), 0.23-0.13 (m, 2H) | ¹³C NMR (CDCl$_3$) δ 170.51, 170.25, 163.26, 160.22, 145.81, 143.96, 142.23, 140.26, 129.26, 128.35, 126.03, 109.67, 89.47, 81.42, 79.10, 77.25, 74.78, 73.99, 56.19, 53.22, 51.77, 35.53, 20.87, 10.72, 3.18, 3.05 |
| 81 | 75-81 | — | HRMS-ESI (m/z) [M + H]⁺ calcd for C$_{30}$H$_{32}$N$_2$O$_9$, 548.2159; found, 548.2159 | ¹H NMR (CDCl$_3$) δ 8.80 (d, J = 7.5 Hz, 1H), 8.36 (d, J = 5.4 Hz, 1H), 7.33-7.09 (m, 7H), 7.00 (d, J = 5.5 Hz, 1H), 6.95 (t, J = 7.4 Hz, 1H), 6.85 (d, J = 8.7 Hz, 2H), 5.30-5.16 (m, 1H), 5.10-5.03 (m, 1H), 4.10-3.92 (m, 4H), 3.89 (s, 3H), 3.76 (dd, J = 11.4, 6.3 Hz, 1H), 3.01-2.79 (m, 2H), 2.46 (tt, J = 9.8, 4.7 Hz, 1H), 2.38 (s, 3H), 1.47 (d, J = 6.3 Hz, 3H) | — |
| 82 | — | — | ESIMS m/z 435.4 ([M + H]⁺) | ¹H NMR (CDCl$_3$) δ 7.35-7.00 (m, 5H), 5.39 (d, J = 7.7 Hz, 1H), 5.09 (dq, J = 12.6, 6.3 Hz, 1H), 4.60 (t, J = 8.4 Hz, 1H), 4.04-3.90 (m, 2H), 3.82 (dd, J = 12.0, 3.3 Hz, 1H), 3.65 (dd, J = 11.5, 5.6 Hz, 1H), 3.36 (dd, J = 8.8, 6.5 Hz, 1H), 3.13-2.92 (m, 3H), 2.67 (dd, J = 14.6, 6.4 Hz, | ¹³C NMR (CDCl$_3$) δ 170.93, 155.22, 140.35, 129.17, 128.33, 126.00, 81.84, 79.95, 79.08, 76.07, 75.30, 74.04, 54.49, 51.86, 35.43, 28.84, 28.30, 20.78, 19.58 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 1H), 2.27-2.09 (m, 1H), 1.82 (hept, J = 6.6 Hz, 1H), 1.43 (s, 9H), 1.25 (d, J = 6.4 Hz, 3H), 0.89 (t, J = 6.8 Hz, 6H) | |
| 83 | — | — | HRMS-ESI (m/z) [M + H]⁺ calcd for C₂₆H₃₂N₂O₇, 484.221; found, 484.221 | ¹H NMR (CDCl₃) δ 11.98 (s, 1H), 8.72 (d, J = 8.0 Hz, 1H), 7.99 (d, J = 5.2 Hz, 1H), 7.37-7.11 (m, 5H), 6.86 (d, J = 5.2 Hz, 1H), 5.29-5.10 (m, 1H), 5.05-4.97 (m, 1H), 4.15-3.95 (m, 3H), 3.93 (s, 3H), 3.72 (dd, J = 11.5, 5.8 Hz, 1H), 3.36 (dd, J = 10.1, 7.1 Hz, 1H), 3.25 (dd, J = 10.1, 6.6 Hz, 1H), 3.13 (dd, J = 9.2, 5.2 Hz, 1H), 3.01 (dd, J = 14.5, 4.1 Hz, 1H), 2.76 (dd, J = 14.5, 6.2 Hz, 1H), 2.31-2.16 (m, 1H), 1.33 (d, J = 6.3 Hz, 3H), 1.11-0.94 (m, 1H), 0.59-0.45 (m, 2H), 0.27-0.10 (m, 2H) | ¹³C NMR (CDCl₃) δ 169.89, 168.95, 155.31, 148.72, 140.63, 140.17, 130.28, 129.25, 128.37, 126.07, 109.54, 81.38, 79.37, 74.55, 74.25, 74.00, 56.08, 52.99, 51.79, 35.54, 20.80, 10.72, 3.19 |
| 84 | — | — | HRMS-ESI (m/z) [M + H]⁺ calcd for C₃₁H₃₄N₂O₉, 578.2264; found, 578.2263 | ¹H NMR (CDCl₃) δ 8.63 (d, J = 7.6 Hz, 1H), 8.31 (d, J = 5.2 Hz, 1H), 7.36-7.08 (m, 7H), 6.96 (d, J = 7.2 Hz, 2H), 6.85 (d, J = 8.6 Hz, 2H), 5.73 (d, J = 2.7 Hz, 2H), 5.30-5.17 (m, 1H), 5.15-5.03 (m, 1H), 4.09-3.98 (m, 4H), 3.91 (s, 3H), 3.78 (dd, J = 11.5, 6.3 Hz, 1H), 3.00-2.83 (m, 2H), 2.47 (tt, J = 9.7, 4.7 Hz, 1H), 2.06 (s, 3H), 1.48 (d, J = 6.3 Hz, 3H) | ¹³C NMR (CDCl₃) δ 170.25, 163.32, 160.23, 156.58, 145.87, 139.10, 129.67, 129.40, 128.38, 126.23, 120.99, 115.28, 109.74, 89.43, 86.87, 79.14, 78.21, 77.27, 75.10, 73.20, 57.02, 56.22, 53.39, 51.59, 35.07, 20.86, 20.64 |
| 85 | — | — | HRMS-ESI (m/z) [M + H]⁺ calcd for C₂₉H₃₈N₂O₉, 558.2577; found, 558.2588 | ¹H NMR (CDCl₃) δ 8.60 (d, J = 7.7 Hz, 1H), 8.29 (d, J = 5.4 Hz, 1H), 7.33-7.13 (m, 5H), 6.95 (d, J = 5.4 Hz, 1H), 5.73 (d, J = 1.7 Hz, 2H), 5.17-5.11 (m, 1H), 5.07-4.90 (m, 1H), 4.16-3.91 (m, 3H), 3.91 (s, 3H), 3.72 (dd, J = 11.5, 5.8 Hz, 1H), 3.37 (dd, J = 8.8, 6.5 Hz, 1H), 3.12-3.07 (m, 2H), 3.06-2.98 (m, 1H), 2.70 (dd, J = 14.6, 6.4 Hz, 1H), 2.28-2.18 (m, 1H), 2.06 (s, 3H), 1.88-1.78 (m, 1H), 1.29 (d, J = 6.4 Hz, 3H), 0.90 (t, J = 6.8 Hz, 6H) | ¹³C NMR (CDCl₃) δ 170.52, 170.24, 163.27, 160.22, 145.81, 143.95, 142.24, 140.39, 129.18, 128.34, 125.99, 109.68, 89.46, 81.79, 78.82, 76.08, 74.79, 74.15, 60.38, 56.19, 53.26, 51.83, 35.43, 28.85, 20.87, 19.53 |
| 86 | — | — | ESIMS m/z 333.2 ([M − Cl]⁺) | — | — |
| 87 | 54-59 | — | HRMS-ESI (m/z) [M + H]⁺ calcd for C₂₈H₃₄N₂O₈, 526.2315; found, 526.2320 | ¹H NMR (CDCl₃) δ 8.75 (d, J = 7.4 Hz, 1H), 8.33 (d, J = 5.4 Hz, 1H), 7.32-7.14 (m, 5H), 6.99 (d, J = 5.5 Hz, 1H), 5.19-5.07 (m, 1H), 5.04-4.97 (m, 1H), 4.08-3.95 (m, 2H), 3.89 (s, 3H), 3.89-3.83 (m, 1H), 3.71 (dd, J = 11.3, 6.0 Hz, 1H), 3.35 (dd, J = 10.1, 7.1 Hz, 1H), 3.24 (dd, J = 10.1, 6.6 Hz, 1H), 3.12 (dd, J = 10.1, | — |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 5.4 Hz, 1H), 3.00 (dd, J = 14.6, 4.0 Hz, 1H), 2.75 (dd, J = 14.6, 6.2 Hz, 1H), 2.38 (s, 3H), 2.27-2.15 (m, 1H), 1.31 (d, J = 6.3 Hz, 3H), 1.11-0.97 (m, 1H), 0.56-0.48 (m, 2H), 0.26-0.13 (m, 2H) | |

*¹H NMR were run at 400 MHz unless noted otherwise
*¹³C NMR were run at 101 MHz unless noted otherwise
*¹⁹F NMR were run at 376 MHz unless noted otherwise

TABLE 3

Biological Testing Rating Scale
Rating Table for Fungal Pathogens

| % Control | Rating |
|---|---|
| >70 | A |
| ≤70 | B |
| Not Tested | C |

TABLE 4

Biological Activity - PUCCRT and SEPTTR Disease Control in High and Low Volume Applications

| | PUCCRT* | | | | SEPTTR* | | | |
|---|---|---|---|---|---|---|---|---|
| | 1DP* Rate | | 3DC* Rate | | 1DP* Rate | | 3DC* Rate | |
| Cmpd. No. | 121.5 g/H* | 100 ppm* | 121.5 g/H* | 100 ppm* | 121.5 g/H* | 100 ppm* | 121.5 g/H* | 100 ppm* |
| 3 | C | A | C | A | C | A | C | B |
| 6 | A | C | A | C | A | C | A | C |
| 8 | A | C | A | C | A | C | A | C |
| 9 | A | C | A | C | A | C | A | C |
| 10 | A | C | B | C | A | C | A | C |
| 14 | A | C | A | C | A | C | A | C |
| 17 | C | A | C | A | C | A | C | A |
| 18 | A | C | A | C | B | C | A | C |
| 20 | A | C | A | C | A | C | A | C |
| 23 | C | A | C | B | C | A | C | B |
| 24 | C | A | C | A | C | A | C | A |
| 25 | C | A | C | A | C | A | C | A |
| 26 | C | A | C | A | C | A | C | A |
| 28 | A | C | A | C | A | C | A | C |
| 30 | A | C | A | C | A | C | A | C |
| 32 | A | C | A | C | A | C | A | C |
| 36 | C | B | C | B | C | B | C | A |
| 37 | C | A | C | A | C | A | C | A |
| 38 | C | A | C | A | C | A | C | A |
| 40 | A | C | A | C | A | C | A | C |
| 43 | A | C | A | C | B | C | A | C |
| 44 | A | C | A | C | A | C | A | C |
| 45 | C | A | C | B | C | A | C | B |
| 46 | C | A | C | A | C | A | C | B |
| 47 | A | C | B | C | A | C | A | C |
| 48 | A | C | A | C | A | C | A | C |
| 53 | C | A | C | A | C | B | C | B |
| 57 | A | C | A | C | B | C | A | C |
| 58 | C | A | C | A | B | C | B | A |
| 59 | A | C | A | C | A | C | A | C |
| 60 | C | A | C | A | C | A | C | B |
| 62 | A | C | A | C | A | C | A | C |
| 64 | A | C | B | C | A | C | A | C |
| 65 | C | A | C | B | C | A | C | A |
| 67 | A | C | A | C | A | C | A | C |
| 68 | A | C | A | C | B | C | A | C |
| 71 | A | C | A | C | A | C | A | C |
| 72 | C | A | C | B | C | B | C | B |
| 73 | A | C | A | C | A | C | A | C |
| 76 | C | C | C | C | C | C | C | C |
| 77 | C | C | C | C | C | C | C | C |
| 79 | A | C | A | C | A | C | A | C |
| 80 | A | A | A | A | A | A | A | A |
| 81 | A | C | A | C | A | C | A | C |
| 83 | C | A | C | A | C | A | C | A |
| 84 | A | C | A | C | A | C | A | C |
| 85 | A | A | A | A | A | B | A | A |
| 87 | C | A | C | A | C | A | C | A |

*PUCCRT—Wheat Brown Rust (*Puccinia triticina*)
*SEPTTR—Wheat Leaf Blotch (*Septoria tritici*)
*1DP—1 Day Protectant
*3DC—3 Day Curative
*g/H—Grams Per Hectare
*ppm—Parts Per Million

TABLE 5

Biological Activity - Disease Control at 100 ppm

| Compound Number | ALTESO* | CERCBE* | COLLLA* 1 DP* | ERYSCI* | ERYSGH* |
|---|---|---|---|---|---|
| 6 | B | A | A | A | A |
| 9 | B | B | A | B | B |

*ALTESO—Tomato Early Blight (*Alternaria solani*)
*CERCBE—Leaf Spot of Sugar Beets (*Cercospora beticola*)
*COLLLA—Cucumber Anthracnose (*Glomerella lagenarium*; Anamorph: *Colletotricum lagenarium*)
*ERYSCI—Powdery Mildew of Cucumber (*Erysiphe cichoracearum*)
*ERYSGH—Barley Powdery Mildew (*Blumeria graminis* f.sp. *hordei*; Synonym: *Erysiphe graminis* f.sp. *hordei*)
*1 DP—1 Day Protectant

TABLE 6

| Biological Activity - Disease Control at 100 ppm | | | | |
|---|---|---|---|---|
| Compound. Number | LEPTNO* | PYRIOR* 1 DP* | RHYNSE* | UNCINE* |
| 6 | A | A | A | A |
| 9 | A | B | A | A |

*LEPTNO—Wheat Glume Blotch (*Leptosphaeria nodorum*)
*PYRIOR—Rice Blast (*Magnaporthe grisea*; Anamorph: *Pyricularia oryzae*)
*RHYNSE—Barley Scald (*Rhyncosporium secalis*)
*UNCINE—Grape Powdery Mildew (*Uncinula necator*)
*1 DP—1 Day Protectant

What is claimed is:

1. A composition for the control of a fungal pathogen including at least one compound of Formula I

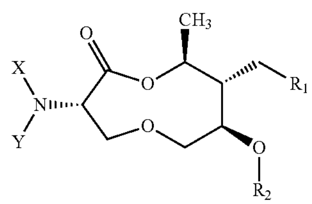

I wherein

X is hydrogen or $C(O)R_3$;

Y is hydrogen, $C(O)R_3$, or Q;

Q is $R_1$ is hydrogen, alkyl, alkenyl, aryl, alkoxy, or acyl, each optionally substituted with 0, 1 or multiple $R_6$;

$R_2$ is hydrogen, alkyl, aryl, $—Si(R_5)_3$, alkenyl, or acyl, each optionally substituted with 0, 1 or multiple $R_6$;

$R_3$ is alkoxy or benzyloxy, each optionally substituted with 0, 1, or multiple $R_6$;

$R_4$ is hydrogen, $—C(O)R_5$, or $—CH_2OC(O)R_5$;

$R_5$ is alkyl, alkoxy, or aryl, each optionally substituted with 0, 1, or multiple $R_6$;

$R_6$ is hydrogen, alkyl, aryl, acyl, halo, alkenyl, alkoxy, heteroaryl, heterocyclyl, or thioalkyl, each optionally substituted with 0, 1, or multiple $R_7$; and $R_7$ is hydrogen, alkyl, aryl, or halo, wherein when $R_1$ is an unsubstituted phenyl, $R_2$ is an alkyl substituted with 1 or multiple $R_6$, and at least one $R_6$ is an alkoxy substituted with 1 or multiple $R_7$ and at least one $R_7$ is an aryl.

2. A composition according to claim 1, wherein X is hydrogen and Y is Q.

3. A composition according to claim 2, wherein $R_4$ is hydrogen.

4. A composition according to claim 3, wherein $R_1$ is chosen from alkyl and aryl, each optionally substituted with 0, 1 or multiple $R_6$.

5. A composition according to claim 3, wherein $R_2$ is chosen from hydrogen, alkyl, aryl, and acyl, each optionally substituted with 0, 1 or multiple $R_6$.

6. A composition according to claim 3, wherein $R_1$ is chosen from alkyl and aryl, each optionally substituted with 0, 1 or multiple $R_6$, and $R_2$ is chosen from hydrogen, alkyl, aryl, and acyl, each optionally substituted with 0, 1 or multiple $R_6$.

7. A composition according to claim 2, wherein $R_4$ is $—C(O)R_5$ or $—CH_2OC(O)R_5$.

8. A composition according to claim 7, wherein $R_5$ is chosen from alkyl and alkoxy, each optionally substituted with 0, 1, or multiple $R_6$.

9. A composition according to claim 8, wherein $R_1$ is chosen from alkyl and aryl, each optionally substituted with 0, 1 or multiple $R_6$.

10. A composition according to claim 8, wherein $R_2$ is chosen from hydrogen, alkyl, aryl, and acyl, each optionally substituted with 0, 1 or multiple $R_6$.

11. A composition according to claim 8, wherein $R_1$ is chosen from alkyl and aryl, each optionally substituted with 0, 1 or multiple $R_6$, and $R_2$ is chosen from hydrogen, alkyl, aryl, and acyl, each optionally substituted with 0, 1 or multiple $R_6$.

12. A composition according to claim 11, wherein $R_5$ is chosen from $—CH_3$, $—CH_2OCH_2CH_3$, and $—CH_2CH_2OCH_3$.

13. A composition for the control of a fungal pathogen including at least one composition of claim 6 and a phytologically acceptable carrier material.

14. A composition for the control of a fungal pathogen including at least one composition of claim 11 and a phytologically acceptable carrier material.

15. A composition for the control of a fungal pathogen including at least one composition of claim 12 and a phytologically acceptable carrier material.

16. A composition for the control of a fungal pathogen including mixtures of at least one composition of claim 6 and another pesticide selected from the group consisting of: fungicides, insecticides, nematocides, miticides, arthropodicides, bactericides and combinations thereof.

17. A composition for the control of a fungal pathogen including mixtures of at least one composition of claim 11 and another pesticide selected from the group consisting of: fungicides, insecticides, nematocides, miticides, arthropodicides, bactericides and combinations thereof.

18. A composition for the control of a fungal pathogen including mixtures of at least one composition of claim 12 and another pesticide selected from the group consisting of: fungicides, insecticides, nematocides, miticides, arthropodicides, bactericides and combinations thereof.

19. A method for the control of fungal attack on a plant, the method including the step of: applying a fungicidally effective amount of at least one composition of claim 6 to at least one of the plant, an area adjacent to the plant, soil adapted to support growth of the plant, a root of the plant, and foliage of the plant.

20. A method for the control of fungal attack on a plant, the method including the step of: applying a fungicidally effective amount of at least one composition of claim 11 to at least one of the group consisting of: the plant, an area adjacent to the plant, soil adapted to support growth of the plant, a root of the plant, and foliage of the plant.

21. A method for the control of fungal attack on a plant, the method including the step of: applying a fungicidally effective amount of at least one composition of claim 12 to at least one of the group consisting of: the plant, an area adjacent to the plant, soil adapted to support growth of the plant, a root of the plant, and foliage of the plant.

22. A method for the control of fungal attack on a plant, the method including the step of: applying a fungicidally effective amount of at least one composition of claim 15 to at least one of the group consisting of: plant, an area adjacent to the plant, soil adapted to support growth of the plant, a root of the plant, and foliage of the plant.

23. A method for the control of fungal attack on a plant, the method including the step of: applying a fungicidally effective amount of at least one composition of claim 18 to at least one of the group consisting of: the plant, an area adjacent to the plant, soil adapted to support growth of the plant, a root of the plant, and foliage of the plant.

* * * * *